US011739317B2

(12) United States Patent
Barna et al.

(10) Patent No.: US 11,739,317 B2
(45) Date of Patent: *Aug. 29, 2023

(54) SYSTEMS AND METHODS TO ASSESS RNA STABILITY

(71) Applicant: The Board of Trustees of the Leland Stanford Junior University, Stanford, CA (US)

(72) Inventors: Maria Barna, Stanford, CA (US); Kathrin Leppek, Stanford, CA (US); Gun Woo Byeon, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/454,795

(22) Filed: Nov. 12, 2021

(65) Prior Publication Data

US 2022/0135964 A1 May 5, 2022

Related U.S. Application Data

(63) Continuation of application No. PCT/US2021/040027, filed on Jul. 1, 2021.

(60) Provisional application No. 63/165,662, filed on Mar. 24, 2021, provisional application No. 63/072,669, (Continued)

(51) Int. Cl.
*C12N 15/10* (2006.01)
*C12Q 1/6806* (2018.01)
*G01N 27/447* (2006.01)

(52) U.S. Cl.
CPC ..... *C12N 15/1065* (2013.01); *C12N 15/1089* (2013.01); *C12N 15/1096* (2013.01); *C12Q 1/6806* (2013.01); *G01N 27/44791* (2013.01)

(58) Field of Classification Search
CPC ............ C12N 15/1065; C12N 15/1089; C12N 15/1096; C12Q 1/6806; G01N 27/44791
See application file for complete search history.

(56) References Cited

U.S. PATENT DOCUMENTS

| 5,846,772 A | 12/1998 | Hodgson et al. |
| 8,278,036 B2 | 10/2012 | Kariko et al. |
| 9,885,034 B2 | 2/2018 | Saxonov |

(Continued)

FOREIGN PATENT DOCUMENTS

| CN | 103725773 B | 11/2015 |
| WO | 2012041802 A1 | 4/2012 |

(Continued)

OTHER PUBLICATIONS

Cottrell et al. Nature Communications (2018)9:301 p. 1-13 (Year: 2018).*

(Continued)

*Primary Examiner* — Jeremy C Flinders
(74) *Attorney, Agent, or Firm* — KPPB LLP

(57) ABSTRACT

Systems and methods for assessing mRNA in vivo and/or in vitro stability are disclosed. Some embodiments methods obtain RNA indexed or barcoded RNA molecules which are then tested against various conditions including stability inside of cells, stability in cell lysate, and stability in solution (e.g., for storage and/or transportation). Additional embodiments describe methods to determine degradation points with single base resolution.

19 Claims, 11 Drawing Sheets

Specification includes a Sequence Listing.

Related U.S. Application Data filed on Aug. 31, 2020, provisional application No. 63/051,269, filed on Jul. 13, 2020.

(56) References Cited

U.S. PATENT DOCUMENTS

| | | | |
|---|---|---|---|
| 10,022,435 | B2 | 7/2018 | Ciaramella et al. |
| 10,460,220 | B2* | 10/2019 | Church ............... G06K 19/022 |
| 2004/0248140 | A1 | 12/2004 | Endo et al. |
| 2006/0234965 | A1 | 10/2006 | Lee et al. |
| 2010/0047261 | A1 | 2/2010 | Hoerr et al. |
| 2014/0193460 | A1 | 7/2014 | Spector et al. |
| 2014/0206753 | A1 | 7/2014 | Guild et al. |
| 2019/0345513 | A1 | 11/2019 | Qureshi et al. |
| 2020/0017858 | A1 | 1/2020 | Volles et al. |
| 2020/0032274 | A1 | 1/2020 | Mauger et al. |
| 2020/0063190 | A1 | 2/2020 | Chenchik et al. |
| 2022/0010299 | A1 | 1/2022 | Das et al. |
| 2022/0064631 | A1 | 3/2022 | Barna et al. |
| 2022/0162588 | A1 | 5/2022 | Barna et al. |

FOREIGN PATENT DOCUMENTS

| | | |
|---|---|---|
| WO | 2017070626 A2 | 4/2017 |
| WO | 2019209079 A1 | 10/2019 |
| WO | 2021011433 A1 | 1/2021 |
| WO | 2022015513 A2 | 1/2022 |
| WO | 2022015514 A1 | 1/2022 |
| WO | 2022015513 A3 | 2/2022 |
| WO | 2022047427 A2 | 3/2022 |
| WO | 2022015513 A4 | 4/2022 |
| WO | 2022047427 A3 | 4/2022 |

OTHER PUBLICATIONS

Wreschner et al. Eur. J. Biochem. 172, 333-340 (1988) (Year: 1988).*
Wakida et al. (Biochemical and Biophysical Research Communications 527:4, Jul. 5, 2020, p. 993-999) (Year: 2020).*
Chen et al. (Mol Syst Biol. (2015) 11: 781, 1-10). (Year: 2015).*
GenBank Accession No. LS992084.1, Triticum aestivum genome assembly, chromosome: 2B, Aug. 19, 2018, Retrieved on Oct. 29, 2021 from: https://www.ncbi.nlm.nih.gov/nuccore/LS992084, 1 pg.
International Search Report and Written Opinion for International Application No. PCT/US2021/040028, Search completed Oct. 29, 2021, dated Dec. 23, 2021, 16 Pgs.
International Search Report and Written Opinion for International Application No. PCT/US2021/040027, Search completed Oct. 5, 2021, dated Jan. 6, 2022, 31 Pgs.
International Search Report and Written Opinion for International Application No. PCT/US2021/048561, Search completed Jan. 21, 2022, dated Feb. 16, 2022, 22 Pgs.
Brogna et al., "Nonsense-mediated mRNA decay (NMD) mechanisms", Nature Structural & Molecular Biology, vol. 16, Feb. 2009, pp. 107-113, doi: https://doi.org/10.1038/nsmb.1550.
Bunnik et al., "Polysome profiling reveals translational control of gene expression in the human malaria parasite Plasmodium falciparum", Genome Biology, vol. 14, No. R128, Nov. 22, 2013, 18 pgs.
Cataldo, "Ozone Degradation of Biological Macromolecules: Proteins, Hemoglobin, RNA, and DNA", Ozone: Science & Engineering, The Journal of the International Ozone Association, vol. 28, No. 5, Dec. 5, 2006, pp. 317-328.
Chan et al., "Non-Invasive Measurement of mRNA Decay Reveals Translation Initiation as the Major Determinant of mRNA Stability", eLife, vol. 7, e32536, Sep. 7, 2018 , 32 pgs. DOI: https://doi.org/10.7554/eLife.32536.
Chasse et al., "Analysis of translation using polysome profiling", Nucleic Acids Research, vol. 45, No. 3, Feb. 2017, Online Publication: Oct. 7, 2016, e15, 9 pgs., https://doi.org/10.1093/nar/gkw907.
Cohen et al., "Natural Selection and Algorithmic Design of mRNA", Journal of Computational Biology, vol. 10, No. 3-4, Jul. 5, 2004, pp. 419-432.
Daslab, "SuperFolder COVID-19 mRNA vaccine", GitHub, Inc., 2021, Retrieved from: https://github.com/DasLab/superfolder-covid-mrna-vaccines, 6 pgs.
Davis, "Stabilization of RNA stacking by pseudouridine", Nucleic Acids Research, vol. 23, No. 24, Dec. 25, 1995, pp. 5020-5026, doi: https://doi.org/10.1093/nar/23.24.5020.
Do et al., "CONTRAfold: RNA secondary structure prediction without physics-based models", Bioinformatics, vol. 22, No. 14, Jul. 15, 2006, pp. e90-e98, doi: https://doi.org/10.1093/bioinformatics/btl246.
Erasmus et al., "An Alphavirus-derived replicon RNA vaccine induces SARS-CoV-2 neutralizing antibody and T cell responses in mice and nonhuman primates", Science Translational Medicine, vol. 12, No. 555, Aug. 5, 2020, eabc9396, 11 pgs, doi: 10.1126/scitranslmed.abc9396.
Erasmus et al., "Preparing for Pandemics: RNA Vaccines at the Forefront", Molecular Therapy, vol. 28, No. 7, Jul. 8, 2020, Online Publication: Jun. 23, 2020, pp. 1559-1560.
Fischer et al., "Structure-Mediated RNA Decay by UPF1 and G3BP1", Molecular Cell, vol. 78, No. 1, Apr. 2, 2020, pp. 70-84.e6, doi: https://doi.org/10.1016/j.molcel.2020.01.021.
Geall et al., "Nonviral delivery of self-amplifying RNA vaccines", PNAS, vol. 109, No. 36, Sep. 4, 2012, pp. 14604-14609, doi: https://doi.org/10.1073/pnas.1209367109.
Hamada et al., "Prediction of RNA secondary structure by maximizing pseudo-expected accuracy", BMC Bioinformatics, vol. 11, No. 586, Nov. 30, 2010, 10 pgs.
Kaczmarek et al., "Advances in the delivery of RNA therapeutics: from concept to clinical reality", Genome Medicine, vol. 9, No. 60, Jun. 27, 2017, 16 pgs.
Kariko et al., "Incorporation of Pseudouridine Into mRNA Yields Superior Nonimmunogenic Vector With Increased Translational Capacity and Biological Stability", Molecular Therapy, vol. 16, No. 11, Nov. 1, 2008, pp. 1833-1840, doi: https://doi.org/10.1038/mt.2008.200.
Kaukinen et al., "The reactivity of phosphodiester bonds within linear singlestranded oligoribonucleotides is strongly dependent on the base sequence", Nucleic Acids Research, vol. 30, No. 2, Jan. 15, 2002, pp. 468-474, doi: 10.1093/nar/30.2.468.
Koh et al., "Tuning of mRNA stability through altering 3'-UTR sequences generates distinct output expression in a synthetic circuit driven by p53 oscillations", Scientific Reports, vol. 9, No. 5976, Apr. 12, 2019, 8 pgs.
Li et al., "Kinetics of RNA Degradation by Specific Base Catalysis of Transesterification Involving the 2'-Hydroxyl Group", Journal of the American Chemical Society, vol. 121, No. 23, May 25, 1999, pp. 5364-5372, doi: 10.1021/ja990592p.
Liang et al., "Polysome-profiling in small tissue samples", Nucleic Acids Research, vol. 46, No. 1, Jan. 9, 2018, e3, 13 pgs., https://doi.org/10.1093/nar/gkx940.
Lorenz et al., "ViennaRNA Package 2.0", Algorithms for Molecular Biology, vol. 6, No. 26, Nov. 24, 2011, 14 pgs.
Markham et al., "The Structure of Ribonucleic Acids. 1. Cyclic nucleotides produced by ribonuclease and by alkaline hydrolysis", Biochemical Journal, vol. 52, No. 4, Dec. 1, 1952, pp. 552-557, doi: https://doi.org/10.1042/bj0520552.
Mauger et al., "mRNA structure regulates protein expression through changes in functional half-life", PNAS, vol. 116, No. 48, Nov. 26, 2019, pp. 24075-24083, doi: https://doi.org/10.1073/pnas.1908052116.
McKay et al., "Self-amplifying RNA SARS-CoV-2 lipid nanoparticle vaccine candidate induces high neutralizing antibody titers in mice", Nature Communications, 2020, vol. 11, article 3523, published online Jul. 9, 2020, 7 pgs.
Mercier et al., "Translation-dependent and independent mRNA decay occur through mutually exclusive pathways that are defined by ribosome density during T Cell activation", bioRxiv, Oct. 17, 2020, 45 pgs, doi: https://doi.org/10.1101/2020.10.16.341222.

(56) References Cited

OTHER PUBLICATIONS

Mikkola et al., "The effect of secondary structure on cleavage of the phosphodiester bonds of RNA", Cell Biochemistry and Biophysics, vol. 34, Feb. 2001, pp. 95-119.
Oivanen et al., "Kinetics and Mechanisms for the Cleavage and Isomerization of the Phosphodiester Bonds of RNA by Brønsted Acids and Bases", Chemical Reviews, vol. 98, No. 3, May 7, 1998, pp. 961-990, doi: 10.1021/cr960425x.
Park et al., "Staufen-mediated mRNA decay", Wiley Interdisciplinary Reviews RNA, vol. 4, No. 4, Jul. 2013, pp. 423-435, doi: 10.1002/wrna.1168.
Pringle et al., "Polysome Profiling Analysis of mRNA and Associated Proteins Engaged in Translation", Current Protocols in Molecular Biology, vol. 125, No. 1, Jan. 2019, Electronic Publication: Oct. 29, 2018, e79, doi: 10.1002/cpmb.79.
Regulski et al., "In-Line Probing Analysis of Riboswitches", Part of the Methods In Molecular Biology™ book series, vol. 419, 2008, pp. 53-67, doi: 10.1007/978-1-59745-033-1_4.
Reuter et al., "RNAstructure: software for RNA secondary structure prediction and analysis", BMC Bioinformatics, vol. 11, No. 129, Mar. 15, 2010, 9 pgs.
Terai et al., "CDSfold: an algorithm for designing a protein-coding sequence with the most stable secondary structure", Bioinformatics, vol. 32, No. 6, Mar. 15, 2016, pp. 828-834, doi: https://doi.org/10.1093/bioinformatics/btv678.
Verbeke et al., "Three decades of messenger RNA vaccine development", Nano Today, vol. 28, Oct. 2019, 100766, 17 pgs.
Wayment-Steele et al., "Theoretical basis for Stabilizing Messenger RNA through Secondary Structure Design", (Version 2. bioRxiv. Preprint. Aug. 24, 2020, [online], [Retrieved on Sep. 27, 2021], Retrieved from the internet URL:https://www.ncbi.nlm.nih.gov/pmc/articles/PMC7457604/, 25 pgs.
World Health Organization, "WHO Preferred Product Characteristics for Next-Generation Influenza Vaccines", World Health Organization, Department of Immunization, Vaccines and Biologicals, ISBN 978-92-4-151246-6, 2017, 42 pgs.
Zadeh et al., "NUPACK: Analysis and Design of Nucleic Acid Systems", Journal of Computational Chemistry, Software News and Update, vol. 32, Jan. 15, 2011, pp. 170-173, doi: 10.1002/jcc.21596.
Zhang et al., "A Thermostable mRNA Vaccine against COVID-19", Cell, vol. 182, No. 5, Sep. 3, 2020, pp. 1271-1283.e16, doi: 10.1016/j.cell.2020.07.024.
Zhang et al., "LinearDesign: Efficient Algorithms for Optimized mRNA Sequence Design", arXiv:2004.10177v1 [q-bio.BM], Apr. 21, 2020, 9 pgs.
Zhao et al., "Long-term storage of lipid-like nanoparticles for mRNA delivery", Bioactive Materials, vol. 5, No. 2, Jun. 2020, pp. 358-363.
International Preliminary Report on Patentability for International Application PCT/US2021/040027, Report dated Jan. 17, 2023, dated Jan. 26, 2023, 7 Pgs.
International Preliminary Report on Patentability for International Application PCT/US2021/040028, Report dated Jan. 17, 2023, dated Jan. 26, 2023, 7 Pgs.
International Preliminary Report on Patentability for International Application PCT/US2021/048561, Report dated Feb. 28, 2023, dated Mar. 9, 2023, 13 Pgs.

\* cited by examiner

| Cap | 5'UTR | CDS | Profiling 1 | Barcode | Profiling 2 | 3'UTR | Tailing |

Fig. 2

SEQUENCE LISTING

<160> NUMBER OF SEQ ID NOS: 1270

<210> SEQ ID NO 1
<211> LENGTH: 621
<212> TYPE: DNA
<213> ORGANISM: artificial sequence
<220> FEATURE:
<223> OTHER INFORMATION: Modified luciferase - nanoluciferase

<400> SEQUENCE: 1

| | | | | | |
|---|---|---|---|---|---|
| atggccgttt | acccatacga | tgttcctgac | tatgcgggct | atccctatga | cgtcccggac | 60 |
| tatgcaggct | cctatccata | tgacgttcca | gattacgctg | gatctggcgt | cttcacactc | 120 |
| gaagatttcg | ttggggactg | gcgacagaca | gccggctaca | acctggacca | agtccttgaa | 180 |
| cagggaggtg | tgtccagttt | gtttcagaat | ctcggggtgt | ccgtaactcc | gatccaaagg | 240 |
| attgtcctga | gcggtgaaaa | tgggctgaag | atcgacatcc | atgtcatcat | cccgtatgaa | 300 |
| ggtctgagcg | gcgaccaaat | gggccagatc | gaaaaatttt | ttaaggtggt | gtaccctgtg | 360 |
| gatgatcatc | actttaaggt | gatcctgcac | tatggcacac | tggtaatcga | cggggttacg | 420 |
| ccgaacatga | tcgactattt | cggacggccg | tatgaaggca | tcgccgtgtt | cgacggcaaa | 480 |
| aagatcactg | taacagggac | cctgtggaac | ggcaacaaaa | ttatcgacga | gcgcctgatc | 540 |
| aaccccgacg | gctccctgct | gttccgagta | accatcaacg | gagtgaccgg | ctggcggctg | 600 |
| tgcgaacgca | ttctggcgta | a | | | | 621 |

<210> SEQ ID NO 2
<211> LENGTH: 6
<212> TYPE: DNA
<213> ORGANISM: Artificial Sequence
<220> FEATURE:
<223> OTHER INFORMATION: Barcoding sequence

<400> SEQUENCE: 2 gcttag                                                            6

<210> SEQ ID NO 3
<211> LENGTH: 6
<212> TYPE: DNA
<213> ORGANISM: Artificial Sequence
<220> FEATURE:
<223> OTHER INFORMATION: Barcoding sequence

<400> SEQUENCE: 3 acgaac                                                            6

<210> SEQ ID NO 4
<211> LENGTH: 6
<212> TYPE: DNA
<213> ORGANISM: Artificial Sequence

```
<220> FEATURE:
<223> OTHER INFORMATION: Barcoding sequence

<400> SEQUENCE: 4 ttcgga                                                                6

<210> SEQ ID NO 5
<211> LENGTH: 6
<212> TYPE: DNA
<213> ORGANISM: Artificial Sequence
<220> FEATURE:
<223> OTHER INFORMATION: Barcoding sequence

<400> SEQUENCE: 5 cactgt                                                                6

<210> SEQ ID NO 6
<211> LENGTH: 6
<212> TYPE: DNA
<213> ORGANISM: Artificial Sequence
<220> FEATURE:
<223> OTHER INFORMATION: Barcoding sequence

<400> SEQUENCE: 6 attccg                                                                6

<210> SEQ ID NO 7
<211> LENGTH: 6
<212> TYPE: DNA
<213> ORGANISM: Artificial Sequence
<220> FEATURE:
<223> OTHER INFORMATION: Barcoding sequence

<400> SEQUENCE: 7 ttgcac                                                                6

<210> SEQ ID NO 8
<211> LENGTH: 6
<212> TYPE: DNA
<213> ORGANISM: Artificial Sequence
<220> FEATURE:
<223> OTHER INFORMATION: Barcoding sequence

<400> SEQUENCE: 8 agtacg                                                                6

<210> SEQ ID NO 9
<211> LENGTH: 6
<212> TYPE: DNA
<213> ORGANISM: Artificial Sequence
<220> FEATURE:
<223> OTHER INFORMATION: Barcoding sequence

<400> SEQUENCE: 9 agaacc                                                                6

<210> SEQ ID NO 10
<211> LENGTH: 6
<212> TYPE: DNA
<213> ORGANISM: Artificial Sequence
<220> FEATURE:
<223> OTHER INFORMATION: Barcoding sequence

<400> SEQUENCE: 10 catacg                                                                6
```

```
<210> SEQ ID NO 11
<211> LENGTH: 6
<212> TYPE: DNA
<213> ORGANISM: Artificial Sequence
<220> FEATURE:
<223> OTHER INFORMATION: Barcoding sequence

<400> SEQUENCE: 11 tactgc                                                                  6

<210> SEQ ID NO 12
<211> LENGTH: 6
<212> TYPE: DNA
<213> ORGANISM: Artificial Sequence
<220> FEATURE:
<223> OTHER INFORMATION: Barcoding sequence

<400> SEQUENCE: 12 aggatc                                                                  6

<210> SEQ ID NO 13
<211> LENGTH: 6
<212> TYPE: DNA
<213> ORGANISM: Artificial Sequence
<220> FEATURE:
<223> OTHER INFORMATION: Barcoding sequence

<400> SEQUENCE: 13 acttgc                                                                  6

<210> SEQ ID NO 14
<211> LENGTH: 6
<212> TYPE: DNA
<213> ORGANISM: Artificial Sequence
<220> FEATURE:
<223> OTHER INFORMATION: Barcoding sequence

<400> SEQUENCE: 14 aacgtg                                                                  6

<210> SEQ ID NO 15
<211> LENGTH: 6
<212> TYPE: DNA
<213> ORGANISM: Artificial Sequence
<220> FEATURE:
<223> OTHER INFORMATION: Barcoding sequence

<400> SEQUENCE: 15 cagaca                                                                  6

<210> SEQ ID NO 16
<211> LENGTH: 6
<212> TYPE: DNA
<213> ORGANISM: Artificial Sequence
<220> FEATURE:
<223> OTHER INFORMATION: Barcoding sequence

<400> SEQUENCE: 16 atagcg                                                                  6

<210> SEQ ID NO 17
<211> LENGTH: 6
<212> TYPE: DNA
<213> ORGANISM: Artificial Sequence
<220> FEATURE:
<223> OTHER INFORMATION: Barcoding sequence
```

```
<400> SEQUENCE: 17 gctaac                                                                6

<210> SEQ ID NO 18
<211> LENGTH: 6
<212> TYPE: DNA
<213> ORGANISM: Artificial Sequence
<220> FEATURE:
<223> OTHER INFORMATION: Barcoding sequence

<400> SEQUENCE: 18 ttcacg                                                                6

<210> SEQ ID NO 19
<211> LENGTH: 6
<212> TYPE: DNA
<213> ORGANISM: Artificial Sequence
<220> FEATURE:
<223> OTHER INFORMATION: Barcoding sequence

<400> SEQUENCE: 19 tgctga                                                                6

<210> SEQ ID NO 20
<211> LENGTH: 6
<212> TYPE: DNA
<213> ORGANISM: Artificial Sequence
<220> FEATURE:
<223> OTHER INFORMATION: Barcoding sequence

<400> SEQUENCE: 20 cgttag                                                                6

<210> SEQ ID NO 21
<211> LENGTH: 6
<212> TYPE: DNA
<213> ORGANISM: Artificial Sequence
<220> FEATURE:
<223> OTHER INFORMATION: Barcoding sequence

<400> SEQUENCE: 21 cttgca                                                                6

<210> SEQ ID NO 22
<211> LENGTH: 6
<212> TYPE: DNA
<213> ORGANISM: Artificial Sequence
<220> FEATURE:
<223> OTHER INFORMATION: Barcoding sequence

<400> SEQUENCE: 22 tgcagt                                                                6

<210> SEQ ID NO 23
<211> LENGTH: 6
<212> TYPE: DNA
<213> ORGANISM: Artificial Sequence
<220> FEATURE:
<223> OTHER INFORMATION: Barcoding sequence

<400> SEQUENCE: 23 tcgtga                                                                6

<210> SEQ ID NO 24
```

```
<210> SEQ ID NO 24
<211> LENGTH: 6
<212> TYPE: DNA
<213> ORGANISM: Artificial Sequence
<220> FEATURE:
<223> OTHER INFORMATION: Barcoding sequence

<400> SEQUENCE: 24 tgcatc                                                                  6

<210> SEQ ID NO 25
<211> LENGTH: 9
<212> TYPE: DNA
<213> ORGANISM: Artificial Sequence
<220> FEATURE:
<223> OTHER INFORMATION: Barcoding sequence

<400> SEQUENCE: 25 cggaagaaa                                                               9

<210> SEQ ID NO 26
<211> LENGTH: 9
<212> TYPE: DNA
<213> ORGANISM: Artificial Sequence
<220> FEATURE:
<223> OTHER INFORMATION: Barcoding sequence

<400> SEQUENCE: 26 gcgaagaaa                                                               9

<210> SEQ ID NO 27
<211> LENGTH: 9
<212> TYPE: DNA
<213> ORGANISM: Artificial Sequence
<220> FEATURE:
<223> OTHER INFORMATION: Barcoding sequence

<400> SEQUENCE: 27 ggcaagaaa                                                               9

<210> SEQ ID NO 28
<211> LENGTH: 9
<212> TYPE: DNA
<213> ORGANISM: Artificial Sequence
<220> FEATURE:
<223> OTHER INFORMATION: Barcoding sequence

<400> SEQUENCE: 28 ggagagaaa                                                               9

<210> SEQ ID NO 29
<211> LENGTH: 9
<212> TYPE: DNA
<213> ORGANISM: Artificial Sequence
<220> FEATURE:
<223> OTHER INFORMATION: Barcoding sequence

<400> SEQUENCE: 29 ccagagaaa                                                               9

<210> SEQ ID NO 30
<211> LENGTH: 9
<212> TYPE: DNA
<213> ORGANISM: Artificial Sequence
<220> FEATURE:
<223> OTHER INFORMATION: Barcoding sequence

<400> SEQUENCE: 30
``` gaggagaaa 9

<210> SEQ ID NO 31
<211> LENGTH: 9
<212> TYPE: DNA
<213> ORGANISM: Artificial Sequence
<220> FEATURE:
<223> OTHER INFORMATION: Barcoding sequence

<400> SEQUENCE: 31 acggagaaa 9

<210> SEQ ID NO 32
<211> LENGTH: 9
<212> TYPE: DNA
<213> ORGANISM: Artificial Sequence
<220> FEATURE:
<223> OTHER INFORMATION: Barcoding sequence

<400> SEQUENCE: 32 ctggagaaa 9

<210> SEQ ID NO 33
<211> LENGTH: 9
<212> TYPE: DNA
<213> ORGANISM: Artificial Sequence
<220> FEATURE:
<223> OTHER INFORMATION: Barcoding sequence

<400> SEQUENCE: 33 cacgagaaa 9

<210> SEQ ID NO 34
<211> LENGTH: 9
<212> TYPE: DNA
<213> ORGANISM: Artificial Sequence
<220> FEATURE:
<223> OTHER INFORMATION: Barcoding sequence

<400> SEQUENCE: 34 agcgagaaa 9

<210> SEQ ID NO 35
<211> LENGTH: 9
<212> TYPE: DNA
<213> ORGANISM: Artificial Sequence
<220> FEATURE:
<223> OTHER INFORMATION: Barcoding sequence

<400> SEQUENCE: 35 tccgagaaa 9

<210> SEQ ID NO 36
<211> LENGTH: 9
<212> TYPE: DNA
<213> ORGANISM: Artificial Sequence
<220> FEATURE:
<223> OTHER INFORMATION: Barcoding sequence

<400> SEQUENCE: 36 gtcgagaaa 9

<210> SEQ ID NO 37
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 37 cgtgagaaa                                                            9

<210> SEQ ID NO 38
<211> LENGTH: 9
<212> TYPE: DNA
<213> ORGANISM: Artificial Sequence
<220> FEATURE:
<223> OTHER INFORMATION: Barcoding sequence

<400> SEQUENCE: 38 gctgagaaa                                                            9

<210> SEQ ID NO 39
<211> LENGTH: 9
<212> TYPE: DNA
<213> ORGANISM: Artificial Sequence
<220> FEATURE:
<223> OTHER INFORMATION: Barcoding sequence

<400> SEQUENCE: 39 cgacagaaa                                                            9

<210> SEQ ID NO 40
<211> LENGTH: 9
<212> TYPE: DNA
<213> ORGANISM: Artificial Sequence
<220> FEATURE:
<223> OTHER INFORMATION: Barcoding sequence

<400> SEQUENCE: 40 gcacagaaa                                                            9

<210> SEQ ID NO 41
<211> LENGTH: 9
<212> TYPE: DNA
<213> ORGANISM: Artificial Sequence
<220> FEATURE:
<223> OTHER INFORMATION: Barcoding sequence

<400> SEQUENCE: 41 cagcagaaa                                                            9

<210> SEQ ID NO 42
<211> LENGTH: 9
<212> TYPE: DNA
<213> ORGANISM: Artificial Sequence
<220> FEATURE:
<223> OTHER INFORMATION: Barcoding sequence

<400> SEQUENCE: 42 aggcagaaa                                                            9

<210> SEQ ID NO 43
<211> LENGTH: 9
<212> TYPE: DNA
<213> ORGANISM: Artificial Sequence
<220> FEATURE:
<223> OTHER INFORMATION: Barcoding sequence

<400> SEQUENCE: 43 tcgcagaaa                                                            9
```

<210> SEQ ID NO 44
<211> LENGTH: 9
<212> TYPE: DNA
<213> ORGANISM: Artificial Sequence
<220> FEATURE:
<223> OTHER INFORMATION: Barcoding sequence

<400> SEQUENCE: 44 gtgcagaaa                                                                 9

<210> SEQ ID NO 45
<211> LENGTH: 9
<212> TYPE: DNA
<213> ORGANISM: Artificial Sequence
<220> FEATURE:
<223> OTHER INFORMATION: Barcoding sequence

<400> SEQUENCE: 45 gaccagaaa                                                                 9

<210> SEQ ID NO 46
<211> LENGTH: 9
<212> TYPE: DNA
<213> ORGANISM: Artificial Sequence
<220> FEATURE:
<223> OTHER INFORMATION: Barcoding sequence

<400> SEQUENCE: 46 tgccagaaa                                                                 9

<210> SEQ ID NO 47
<211> LENGTH: 9
<212> TYPE: DNA
<213> ORGANISM: Artificial Sequence
<220> FEATURE:
<223> OTHER INFORMATION: Barcoding sequence

<400> SEQUENCE: 47 ctccagaaa                                                                 9

<210> SEQ ID NO 48
<211> LENGTH: 9
<212> TYPE: DNA
<213> ORGANISM: Artificial Sequence
<220> FEATURE:
<223> OTHER INFORMATION: Barcoding sequence

<400> SEQUENCE: 48 ggtcagaaa                                                                 9

<210> SEQ ID NO 49
<211> LENGTH: 9
<212> TYPE: DNA
<213> ORGANISM: Artificial Sequence
<220> FEATURE:
<223> OTHER INFORMATION: Barcoding sequence

<400> SEQUENCE: 49 cctcagaaa                                                                 9

<210> SEQ ID NO 50
<211> LENGTH: 9
<212> TYPE: DNA
<213> ORGANISM: Artificial Sequence
<220> FEATURE:

```
<223> OTHER INFORMATION: Barcoding sequence

<400> SEQUENCE: 50 ccgtagaaa                                                                          9

<210> SEQ ID NO 51
<211> LENGTH: 9
<212> TYPE: DNA
<213> ORGANISM: Artificial Sequence
<220> FEATURE:
<223> OTHER INFORMATION: Barcoding sequence

<400> SEQUENCE: 51 cgctagaaa                                                                          9

<210> SEQ ID NO 52
<211> LENGTH: 9
<212> TYPE: DNA
<213> ORGANISM: Artificial Sequence
<220> FEATURE:
<223> OTHER INFORMATION: Barcoding sequence

<400> SEQUENCE: 52 gcctagaaa                                                                          9

<210> SEQ ID NO 53
<211> LENGTH: 9
<212> TYPE: DNA
<213> ORGANISM: Artificial Sequence
<220> FEATURE:
<223> OTHER INFORMATION: Barcoding sequence

<400> SEQUENCE: 53 ggaaggaaa                                                                          9

<210> SEQ ID NO 54
<211> LENGTH: 9
<212> TYPE: DNA
<213> ORGANISM: Artificial Sequence
<220> FEATURE:
<223> OTHER INFORMATION: Barcoding sequence

<400> SEQUENCE: 54 ccaaggaaa                                                                          9

<210> SEQ ID NO 55
<211> LENGTH: 9
<212> TYPE: DNA
<213> ORGANISM: Artificial Sequence
<220> FEATURE:
<223> OTHER INFORMATION: Barcoding sequence

<400> SEQUENCE: 55 gagaggaaa                                                                          9

<210> SEQ ID NO 56
<211> LENGTH: 9
<212> TYPE: DNA
<213> ORGANISM: Artificial Sequence
<220> FEATURE:
<223> OTHER INFORMATION: Barcoding sequence

<400> SEQUENCE: 56 aggaggaaa                                                                          9
```

```
<210> SEQ ID NO 57
<211> LENGTH: 9
<212> TYPE: DNA
<213> ORGANISM: Artificial Sequence
<220> FEATURE:
<223> OTHER INFORMATION: Barcoding sequence

<400> SEQUENCE: 57 tcgaggaaa                                                                 9

<210> SEQ ID NO 58
<211> LENGTH: 9
<212> TYPE: DNA
<213> ORGANISM: Artificial Sequence
<220> FEATURE:
<223> OTHER INFORMATION: Barcoding sequence

<400> SEQUENCE: 58 ctgaggaaa                                                                 9

<210> SEQ ID NO 59
<211> LENGTH: 9
<212> TYPE: DNA
<213> ORGANISM: Artificial Sequence
<220> FEATURE:
<223> OTHER INFORMATION: Barcoding sequence

<400> SEQUENCE: 59 cacaggaaa                                                                 9

<210> SEQ ID NO 60
<211> LENGTH: 9
<212> TYPE: DNA
<213> ORGANISM: Artificial Sequence
<220> FEATURE:
<223> OTHER INFORMATION: Barcoding sequence

<400> SEQUENCE: 60 tgcaggaaa                                                                 9

<210> SEQ ID NO 61
<211> LENGTH: 9
<212> TYPE: DNA
<213> ORGANISM: Artificial Sequence
<220> FEATURE:
<223> OTHER INFORMATION: Barcoding sequence

<400> SEQUENCE: 61 accaggaaa                                                                 9

<210> SEQ ID NO 62
<211> LENGTH: 9
<212> TYPE: DNA
<213> ORGANISM: Artificial Sequence
<220> FEATURE:
<223> OTHER INFORMATION: Barcoding sequence

<400> SEQUENCE: 62 gtcaggaaa                                                                 9

<210> SEQ ID NO 63
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 63 cgtaggaaa                                                                9

<210> SEQ ID NO 64
<211> LENGTH: 9
<212> TYPE: DNA
<213> ORGANISM: Artificial Sequence
<220> FEATURE:
<223> OTHER INFORMATION: Barcoding sequence

<400> SEQUENCE: 64 gctaggaaa                                                                9

<210> SEQ ID NO 65
<211> LENGTH: 9
<212> TYPE: DNA
<213> ORGANISM: Artificial Sequence
<220> FEATURE:
<223> OTHER INFORMATION: Barcoding sequence

<400> SEQUENCE: 65 gaacggaaa                                                                9

<210> SEQ ID NO 66
<211> LENGTH: 9
<212> TYPE: DNA
<213> ORGANISM: Artificial Sequence
<220> FEATURE:
<223> OTHER INFORMATION: Barcoding sequence

<400> SEQUENCE: 66 agacggaaa                                                                9

<210> SEQ ID NO 67
<211> LENGTH: 9
<212> TYPE: DNA
<213> ORGANISM: Artificial Sequence
<220> FEATURE:
<223> OTHER INFORMATION: Barcoding sequence

<400> SEQUENCE: 67 tcacggaaa                                                                9

<210> SEQ ID NO 68
<211> LENGTH: 9
<212> TYPE: DNA
<213> ORGANISM: Artificial Sequence
<220> FEATURE:
<223> OTHER INFORMATION: Barcoding sequence

<400> SEQUENCE: 68 ctacggaaa                                                                9

<210> SEQ ID NO 69
<211> LENGTH: 9
<212> TYPE: DNA
<213> ORGANISM: Artificial Sequence
<220> FEATURE:
<223> OTHER INFORMATION: Barcoding sequence

<400> SEQUENCE: 69 aagcggaaa                                                                9

<210> SEQ ID NO 70
<211> LENGTH: 9
```

-continued

```
<212> TYPE: DNA
<213> ORGANISM: Artificial Sequence
<220> FEATURE:
<223> OTHER INFORMATION: Barcoding sequence

<400> SEQUENCE: 70 ttgcggaaa                                                                 9

<210> SEQ ID NO 71
<211> LENGTH: 9
<212> TYPE: DNA
<213> ORGANISM: Artificial Sequence
<220> FEATURE:
<223> OTHER INFORMATION: Barcoding sequence

<400> SEQUENCE: 71 taccggaaa                                                                 9

<210> SEQ ID NO 72
<211> LENGTH: 9
<212> TYPE: DNA
<213> ORGANISM: Artificial Sequence
<220> FEATURE:
<223> OTHER INFORMATION: Barcoding sequence

<400> SEQUENCE: 72 atccggaaa                                                                 9

<210> SEQ ID NO 73
<211> LENGTH: 9
<212> TYPE: DNA
<213> ORGANISM: Artificial Sequence
<220> FEATURE:
<223> OTHER INFORMATION: Barcoding sequence

<400> SEQUENCE: 73 catcggaaa                                                                 9

<210> SEQ ID NO 74
<211> LENGTH: 9
<212> TYPE: DNA
<213> ORGANISM: Artificial Sequence
<220> FEATURE:
<223> OTHER INFORMATION: Barcoding sequence

<400> SEQUENCE: 74 tgtcggaaa                                                                 9

<210> SEQ ID NO 75
<211> LENGTH: 9
<212> TYPE: DNA
<213> ORGANISM: Artificial Sequence
<220> FEATURE:
<223> OTHER INFORMATION: Barcoding sequence

<400> SEQUENCE: 75 actcggaaa                                                                 9

<210> SEQ ID NO 76
<211> LENGTH: 9
<212> TYPE: DNA
<213> ORGANISM: Artificial Sequence
<220> FEATURE:
<223> OTHER INFORMATION: Barcoding sequence

<400> SEQUENCE: 76
```

```
gttcggaaa                                                         9

<210> SEQ ID NO 77
<211> LENGTH: 9
<212> TYPE: DNA
<213> ORGANISM: Artificial Sequence
<220> FEATURE:
<223> OTHER INFORMATION: Barcoding sequence

<400> SEQUENCE: 77 cgatggaaa                                                         9

<210> SEQ ID NO 78
<211> LENGTH: 9
<212> TYPE: DNA
<213> ORGANISM: Artificial Sequence
<220> FEATURE:
<223> OTHER INFORMATION: Barcoding sequence

<400> SEQUENCE: 78 gcatggaaa                                                         9

<210> SEQ ID NO 79
<211> LENGTH: 9
<212> TYPE: DNA
<213> ORGANISM: Artificial Sequence
<220> FEATURE:
<223> OTHER INFORMATION: Barcoding sequence

<400> SEQUENCE: 79 cagtggaaa                                                         9

<210> SEQ ID NO 80
<211> LENGTH: 9
<212> TYPE: DNA
<213> ORGANISM: Artificial Sequence
<220> FEATURE:
<223> OTHER INFORMATION: Barcoding sequence

<400> SEQUENCE: 80 tggtggaaa                                                         9

<210> SEQ ID NO 81
<211> LENGTH: 9
<212> TYPE: DNA
<213> ORGANISM: Artificial Sequence
<220> FEATURE:
<223> OTHER INFORMATION: Barcoding sequence

<400> SEQUENCE: 81 acgtggaaa                                                         9

<210> SEQ ID NO 82
<211> LENGTH: 9
<212> TYPE: DNA
<213> ORGANISM: Artificial Sequence
<220> FEATURE:
<223> OTHER INFORMATION: Barcoding sequence

<400> SEQUENCE: 82 gtgtggaaa                                                         9

<210> SEQ ID NO 83
<211> LENGTH: 9
<212> TYPE: DNA
<213> ORGANISM: Artificial Sequence
```

```
<220> FEATURE:
<223> OTHER INFORMATION: Barcoding sequence

<400> SEQUENCE: 83 gactggaaa                                                                 9

<210> SEQ ID NO 84
<211> LENGTH: 9
<212> TYPE: DNA
<213> ORGANISM: Artificial Sequence
<220> FEATURE:
<223> OTHER INFORMATION: Barcoding sequence

<400> SEQUENCE: 84 agctggaaa                                                                 9

<210> SEQ ID NO 85
<211> LENGTH: 9
<212> TYPE: DNA
<213> ORGANISM: Artificial Sequence
<220> FEATURE:
<223> OTHER INFORMATION: Barcoding sequence

<400> SEQUENCE: 85 tcctggaaa                                                                 9

<210> SEQ ID NO 86
<211> LENGTH: 9
<212> TYPE: DNA
<213> ORGANISM: Artificial Sequence
<220> FEATURE:
<223> OTHER INFORMATION: Barcoding sequence

<400> SEQUENCE: 86 ctctggaaa                                                                 9

<210> SEQ ID NO 87
<211> LENGTH: 9
<212> TYPE: DNA
<213> ORGANISM: Artificial Sequence
<220> FEATURE:
<223> OTHER INFORMATION: Barcoding sequence

<400> SEQUENCE: 87 ggttggaaa                                                                 9

<210> SEQ ID NO 88
<211> LENGTH: 9
<212> TYPE: DNA
<213> ORGANISM: Artificial Sequence
<220> FEATURE:
<223> OTHER INFORMATION: Barcoding sequence

<400> SEQUENCE: 88 ccttggaaa                                                                 9

<210> SEQ ID NO 89
<211> LENGTH: 9
<212> TYPE: DNA
<213> ORGANISM: Artificial Sequence
<220> FEATURE:
<223> OTHER INFORMATION: Barcoding sequence

<400> SEQUENCE: 89 cgaacgaaa                                                                 9
```

```
<210> SEQ ID NO 90
<211> LENGTH: 9
<212> TYPE: DNA
<213> ORGANISM: Artificial Sequence
<220> FEATURE:
<223> OTHER INFORMATION: Barcoding sequence

<400> SEQUENCE: 90 gcaacgaaa                                                                9

<210> SEQ ID NO 91
<211> LENGTH: 9
<212> TYPE: DNA
<213> ORGANISM: Artificial Sequence
<220> FEATURE:
<223> OTHER INFORMATION: Barcoding sequence

<400> SEQUENCE: 91 cagacgaaa                                                                9

<210> SEQ ID NO 92
<211> LENGTH: 9
<212> TYPE: DNA
<213> ORGANISM: Artificial Sequence
<220> FEATURE:
<223> OTHER INFORMATION: Barcoding sequence

<400> SEQUENCE: 92 tggacgaaa                                                                9

<210> SEQ ID NO 93
<211> LENGTH: 9
<212> TYPE: DNA
<213> ORGANISM: Artificial Sequence
<220> FEATURE:
<223> OTHER INFORMATION: Barcoding sequence

<400> SEQUENCE: 93 acgacgaaa                                                                9

<210> SEQ ID NO 94
<211> LENGTH: 9
<212> TYPE: DNA
<213> ORGANISM: Artificial Sequence
<220> FEATURE:
<223> OTHER INFORMATION: Barcoding sequence

<400> SEQUENCE: 94 gtgacgaaa                                                                9

<210> SEQ ID NO 95
<211> LENGTH: 9
<212> TYPE: DNA
<213> ORGANISM: Artificial Sequence
<220> FEATURE:
<223> OTHER INFORMATION: Barcoding sequence

<400> SEQUENCE: 95 gacacgaaa                                                                9

<210> SEQ ID NO 96
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 96 agcacgaaa                                                                  9

<210> SEQ ID NO 97
<211> LENGTH: 9
<212> TYPE: DNA
<213> ORGANISM: Artificial Sequence
<220> FEATURE:
<223> OTHER INFORMATION: Barcoding sequence

<400> SEQUENCE: 97 tccacgaaa                                                                  9

<210> SEQ ID NO 98
<211> LENGTH: 9
<212> TYPE: DNA
<213> ORGANISM: Artificial Sequence
<220> FEATURE:
<223> OTHER INFORMATION: Barcoding sequence

<400> SEQUENCE: 98 ctcacgaaa                                                                  9

<210> SEQ ID NO 99
<211> LENGTH: 9
<212> TYPE: DNA
<213> ORGANISM: Artificial Sequence
<220> FEATURE:
<223> OTHER INFORMATION: Barcoding sequence

<400> SEQUENCE: 99 ggtacgaaa                                                                  9

<210> SEQ ID NO 100
<211> LENGTH: 9
<212> TYPE: DNA
<213> ORGANISM: Artificial Sequence
<220> FEATURE:
<223> OTHER INFORMATION: Barcoding sequence

<400> SEQUENCE: 100 cctacgaaa                                                                  9

<210> SEQ ID NO 101
<211> LENGTH: 9
<212> TYPE: DNA
<213> ORGANISM: Artificial Sequence
<220> FEATURE:
<223> OTHER INFORMATION: Barcoding sequence

<400> SEQUENCE: 101 gaagcgaaa                                                                  9

<210> SEQ ID NO 102
<211> LENGTH: 9
<212> TYPE: DNA
<213> ORGANISM: Artificial Sequence
<220> FEATURE:
<223> OTHER INFORMATION: Barcoding sequence

<400> SEQUENCE: 102 agagcgaaa                                                                  9

<210> SEQ ID NO 103
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 103 tcagcgaaa                                                                 9

<210> SEQ ID NO 104
<211> LENGTH: 9
<212> TYPE: DNA
<213> ORGANISM: Artificial Sequence
<220> FEATURE:
<223> OTHER INFORMATION: Barcoding sequence

<400> SEQUENCE: 104 ctagcgaaa                                                                 9

<210> SEQ ID NO 105
<211> LENGTH: 9
<212> TYPE: DNA
<213> ORGANISM: Artificial Sequence
<220> FEATURE:
<223> OTHER INFORMATION: Barcoding sequence

<400> SEQUENCE: 105 aaggcgaaa                                                                 9

<210> SEQ ID NO 106
<211> LENGTH: 9
<212> TYPE: DNA
<213> ORGANISM: Artificial Sequence
<220> FEATURE:
<223> OTHER INFORMATION: Barcoding sequence

<400> SEQUENCE: 106 ttggcgaaa                                                                 9

<210> SEQ ID NO 107
<211> LENGTH: 9
<212> TYPE: DNA
<213> ORGANISM: Artificial Sequence
<220> FEATURE:
<223> OTHER INFORMATION: Barcoding sequence

<400> SEQUENCE: 107 tacgcgaaa                                                                 9

<210> SEQ ID NO 108
<211> LENGTH: 9
<212> TYPE: DNA
<213> ORGANISM: Artificial Sequence
<220> FEATURE:
<223> OTHER INFORMATION: Barcoding sequence

<400> SEQUENCE: 108 atcgcgaaa                                                                 9

<210> SEQ ID NO 109
<211> LENGTH: 9
<212> TYPE: DNA
<213> ORGANISM: Artificial Sequence
<220> FEATURE:
<223> OTHER INFORMATION: Barcoding sequence

<400> SEQUENCE: 109
```

```
catgcgaaa                                                                    9

<210> SEQ ID NO 110
<211> LENGTH: 9
<212> TYPE: DNA
<213> ORGANISM: Artificial Sequence
<220> FEATURE:
<223> OTHER INFORMATION: Barcoding sequence

<400> SEQUENCE: 110 tgtgcgaaa                                                                    9

<210> SEQ ID NO 111
<211> LENGTH: 9
<212> TYPE: DNA
<213> ORGANISM: Artificial Sequence
<220> FEATURE:
<223> OTHER INFORMATION: Barcoding sequence

<400> SEQUENCE: 111 actgcgaaa                                                                    9

<210> SEQ ID NO 112
<211> LENGTH: 9
<212> TYPE: DNA
<213> ORGANISM: Artificial Sequence
<220> FEATURE:
<223> OTHER INFORMATION: Barcoding sequence

<400> SEQUENCE: 112 gttgcgaaa                                                                    9

<210> SEQ ID NO 113
<211> LENGTH: 9
<212> TYPE: DNA
<213> ORGANISM: Artificial Sequence
<220> FEATURE:
<223> OTHER INFORMATION: Barcoding sequence

<400> SEQUENCE: 113 caaccgaaa                                                                    9

<210> SEQ ID NO 114
<211> LENGTH: 9
<212> TYPE: DNA
<213> ORGANISM: Artificial Sequence
<220> FEATURE:
<223> OTHER INFORMATION: Barcoding sequence

<400> SEQUENCE: 114 tgaccgaaa                                                                    9

<210> SEQ ID NO 115
<211> LENGTH: 9
<212> TYPE: DNA
<213> ORGANISM: Artificial Sequence
<220> FEATURE:
<223> OTHER INFORMATION: Barcoding sequence

<400> SEQUENCE: 115 acaccgaaa                                                                    9

<210> SEQ ID NO 116
<211> LENGTH: 9
<212> TYPE: DNA
```

```
<213> ORGANISM: Artificial Sequence
<220> FEATURE:
<223> OTHER INFORMATION: Barcoding sequence

<400> SEQUENCE: 116 gtaccgaaa                                                                9

<210> SEQ ID NO 117
<211> LENGTH: 9
<212> TYPE: DNA
<213> ORGANISM: Artificial Sequence
<220> FEATURE:
<223> OTHER INFORMATION: Barcoding sequence

<400> SEQUENCE: 117 tagccgaaa                                                                9

<210> SEQ ID NO 118
<211> LENGTH: 9
<212> TYPE: DNA
<213> ORGANISM: Artificial Sequence
<220> FEATURE:
<223> OTHER INFORMATION: Barcoding sequence

<400> SEQUENCE: 118 atgccgaaa                                                                9

<210> SEQ ID NO 119
<211> LENGTH: 9
<212> TYPE: DNA
<213> ORGANISM: Artificial Sequence
<220> FEATURE:
<223> OTHER INFORMATION: Barcoding sequence

<400> SEQUENCE: 119 gatccgaaa                                                                9

<210> SEQ ID NO 120
<211> LENGTH: 9
<212> TYPE: DNA
<213> ORGANISM: Artificial Sequence
<220> FEATURE:
<223> OTHER INFORMATION: Barcoding sequence

<400> SEQUENCE: 120 agtccgaaa                                                                9

<210> SEQ ID NO 121
<211> LENGTH: 9
<212> TYPE: DNA
<213> ORGANISM: Artificial Sequence
<220> FEATURE:
<223> OTHER INFORMATION: Barcoding sequence

<400> SEQUENCE: 121 tctccgaaa                                                                9

<210> SEQ ID NO 122
<211> LENGTH: 9
<212> TYPE: DNA
<213> ORGANISM: Artificial Sequence
<220> FEATURE:
<223> OTHER INFORMATION: Barcoding sequence

<400> SEQUENCE: 122 cttccgaaa                                                                9
```

```
<210> SEQ ID NO 123
<211> LENGTH: 9
<212> TYPE: DNA
<213> ORGANISM: Artificial Sequence
<220> FEATURE:
<223> OTHER INFORMATION: Barcoding sequence

<400> SEQUENCE: 123 ggatcgaaa                                                                 9

<210> SEQ ID NO 124
<211> LENGTH: 9
<212> TYPE: DNA
<213> ORGANISM: Artificial Sequence
<220> FEATURE:
<223> OTHER INFORMATION: Barcoding sequence

<400> SEQUENCE: 124 ccatcgaaa                                                                 9

<210> SEQ ID NO 125
<211> LENGTH: 9
<212> TYPE: DNA
<213> ORGANISM: Artificial Sequence
<220> FEATURE:
<223> OTHER INFORMATION: Barcoding sequence

<400> SEQUENCE: 125 gagtcgaaa                                                                 9

<210> SEQ ID NO 126
<211> LENGTH: 9
<212> TYPE: DNA
<213> ORGANISM: Artificial Sequence
<220> FEATURE:
<223> OTHER INFORMATION: Barcoding sequence

<400> SEQUENCE: 126 aggtcgaaa                                                                 9

<210> SEQ ID NO 127
<211> LENGTH: 9
<212> TYPE: DNA
<213> ORGANISM: Artificial Sequence
<220> FEATURE:
<223> OTHER INFORMATION: Barcoding sequence

<400> SEQUENCE: 127 tcgtcgaaa                                                                 9

<210> SEQ ID NO 128
<211> LENGTH: 9
<212> TYPE: DNA
<213> ORGANISM: Artificial Sequence
<220> FEATURE:
<223> OTHER INFORMATION: Barcoding sequence

<400> SEQUENCE: 128 ctgtcgaaa                                                                 9

<210> SEQ ID NO 129
<211> LENGTH: 9
<212> TYPE: DNA
<213> ORGANISM: Artificial Sequence
<220> FEATURE:
```

```
<223> OTHER INFORMATION: Barcoding sequence

<400> SEQUENCE: 129 cactcgaaa                                                                9

<210> SEQ ID NO 130
<211> LENGTH: 9
<212> TYPE: DNA
<213> ORGANISM: Artificial Sequence
<220> FEATURE:
<223> OTHER INFORMATION: Barcoding sequence

<400> SEQUENCE: 130 tgctcgaaa                                                                9

<210> SEQ ID NO 131
<211> LENGTH: 9
<212> TYPE: DNA
<213> ORGANISM: Artificial Sequence
<220> FEATURE:
<223> OTHER INFORMATION: Barcoding sequence

<400> SEQUENCE: 131 acctcgaaa                                                                9

<210> SEQ ID NO 132
<211> LENGTH: 9
<212> TYPE: DNA
<213> ORGANISM: Artificial Sequence
<220> FEATURE:
<223> OTHER INFORMATION: Barcoding sequence

<400> SEQUENCE: 132 gtctcgaaa                                                                9

<210> SEQ ID NO 133
<211> LENGTH: 9
<212> TYPE: DNA
<213> ORGANISM: Artificial Sequence
<220> FEATURE:
<223> OTHER INFORMATION: Barcoding sequence

<400> SEQUENCE: 133 cgttcgaaa                                                                9

<210> SEQ ID NO 134
<211> LENGTH: 9
<212> TYPE: DNA
<213> ORGANISM: Artificial Sequence
<220> FEATURE:
<223> OTHER INFORMATION: Barcoding sequence

<400> SEQUENCE: 134 gcttcgaaa                                                                9

<210> SEQ ID NO 135
<211> LENGTH: 9
<212> TYPE: DNA
<213> ORGANISM: Artificial Sequence
<220> FEATURE:
<223> OTHER INFORMATION: Barcoding sequence

<400> SEQUENCE: 135 ccgatgaaa                                                                9
```

```
<210> SEQ ID NO 136
<211> LENGTH: 9
<212> TYPE: DNA
<213> ORGANISM: Artificial Sequence
<220> FEATURE:
<223> OTHER INFORMATION: Barcoding sequence

<400> SEQUENCE: 136 cgcatgaaa                                                                 9

<210> SEQ ID NO 137
<211> LENGTH: 9
<212> TYPE: DNA
<213> ORGANISM: Artificial Sequence
<220> FEATURE:
<223> OTHER INFORMATION: Barcoding sequence

<400> SEQUENCE: 137 gccatgaaa                                                                 9

<210> SEQ ID NO 138
<211> LENGTH: 9
<212> TYPE: DNA
<213> ORGANISM: Artificial Sequence
<220> FEATURE:
<223> OTHER INFORMATION: Barcoding sequence

<400> SEQUENCE: 138 cgagtgaaa                                                                 9

<210> SEQ ID NO 139
<211> LENGTH: 9
<212> TYPE: DNA
<213> ORGANISM: Artificial Sequence
<220> FEATURE:
<223> OTHER INFORMATION: Barcoding sequence

<400> SEQUENCE: 139 gcagtgaaa                                                                 9

<210> SEQ ID NO 140
<211> LENGTH: 9
<212> TYPE: DNA
<213> ORGANISM: Artificial Sequence
<220> FEATURE:
<223> OTHER INFORMATION: Barcoding sequence

<400> SEQUENCE: 140 caggtgaaa                                                                 9

<210> SEQ ID NO 141
<211> LENGTH: 9
<212> TYPE: DNA
<213> ORGANISM: Artificial Sequence
<220> FEATURE:
<223> OTHER INFORMATION: Barcoding sequence

<400> SEQUENCE: 141 tcggtgaaa                                                                 9

<210> SEQ ID NO 142
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 142 gtggtgaaa                                                                   9

<210> SEQ ID NO 143
<211> LENGTH: 9
<212> TYPE: DNA
<213> ORGANISM: Artificial Sequence
<220> FEATURE:
<223> OTHER INFORMATION: Barcoding sequence

<400> SEQUENCE: 143 gacgtgaaa                                                                   9

<210> SEQ ID NO 144
<211> LENGTH: 9
<212> TYPE: DNA
<213> ORGANISM: Artificial Sequence
<220> FEATURE:
<223> OTHER INFORMATION: Barcoding sequence

<400> SEQUENCE: 144 tgcgtgaaa                                                                   9

<210> SEQ ID NO 145
<211> LENGTH: 9
<212> TYPE: DNA
<213> ORGANISM: Artificial Sequence
<220> FEATURE:
<223> OTHER INFORMATION: Barcoding sequence

<400> SEQUENCE: 145 accgtgaaa                                                                   9

<210> SEQ ID NO 146
<211> LENGTH: 9
<212> TYPE: DNA
<213> ORGANISM: Artificial Sequence
<220> FEATURE:
<223> OTHER INFORMATION: Barcoding sequence

<400> SEQUENCE: 146 ctcgtgaaa                                                                   9

<210> SEQ ID NO 147
<211> LENGTH: 9
<212> TYPE: DNA
<213> ORGANISM: Artificial Sequence
<220> FEATURE:
<223> OTHER INFORMATION: Barcoding sequence

<400> SEQUENCE: 147 ggtgtgaaa                                                                   9

<210> SEQ ID NO 148
<211> LENGTH: 9
<212> TYPE: DNA
<213> ORGANISM: Artificial Sequence
<220> FEATURE:
<223> OTHER INFORMATION: Barcoding sequence

<400> SEQUENCE: 148 cctgtgaaa                                                                   9

<210> SEQ ID NO 149
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 149 ggactgaaa                                                                 9

<210> SEQ ID NO 150
<211> LENGTH: 9
<212> TYPE: DNA
<213> ORGANISM: Artificial Sequence
<220> FEATURE:
<223> OTHER INFORMATION: Barcoding sequence

<400> SEQUENCE: 150 ccactgaaa                                                                 9

<210> SEQ ID NO 151
<211> LENGTH: 9
<212> TYPE: DNA
<213> ORGANISM: Artificial Sequence
<220> FEATURE:
<223> OTHER INFORMATION: Barcoding sequence

<400> SEQUENCE: 151 gagctgaaa                                                                 9

<210> SEQ ID NO 152
<211> LENGTH: 9
<212> TYPE: DNA
<213> ORGANISM: Artificial Sequence
<220> FEATURE:
<223> OTHER INFORMATION: Barcoding sequence

<400> SEQUENCE: 152 tggctgaaa                                                                 9

<210> SEQ ID NO 153
<211> LENGTH: 9
<212> TYPE: DNA
<213> ORGANISM: Artificial Sequence
<220> FEATURE:
<223> OTHER INFORMATION: Barcoding sequence

<400> SEQUENCE: 153 acgctgaaa                                                                 9

<210> SEQ ID NO 154
<211> LENGTH: 9
<212> TYPE: DNA
<213> ORGANISM: Artificial Sequence
<220> FEATURE:
<223> OTHER INFORMATION: Barcoding sequence

<400> SEQUENCE: 154 ctgctgaaa                                                                 9

<210> SEQ ID NO 155
<211> LENGTH: 9
<212> TYPE: DNA
<213> ORGANISM: Artificial Sequence
<220> FEATURE:
<223> OTHER INFORMATION: Barcoding sequence

<400> SEQUENCE: 155
``` cacctgaaa 9

<210> SEQ ID NO 156
<211> LENGTH: 9
<212> TYPE: DNA
<213> ORGANISM: Artificial Sequence
<220> FEATURE:
<223> OTHER INFORMATION: Barcoding sequence

<400> SEQUENCE: 156 agcctgaaa 9

<210> SEQ ID NO 157
<211> LENGTH: 9
<212> TYPE: DNA
<213> ORGANISM: Artificial Sequence
<220> FEATURE:
<223> OTHER INFORMATION: Barcoding sequence

<400> SEQUENCE: 157 gtcctgaaa 9

<210> SEQ ID NO 158
<211> LENGTH: 9
<212> TYPE: DNA
<213> ORGANISM: Artificial Sequence
<220> FEATURE:
<223> OTHER INFORMATION: Barcoding sequence

<400> SEQUENCE: 158 cgtctgaaa 9

<210> SEQ ID NO 159
<211> LENGTH: 9
<212> TYPE: DNA
<213> ORGANISM: Artificial Sequence
<220> FEATURE:
<223> OTHER INFORMATION: Barcoding sequence

<400> SEQUENCE: 159 gctctgaaa 9

<210> SEQ ID NO 160
<211> LENGTH: 9
<212> TYPE: DNA
<213> ORGANISM: Artificial Sequence
<220> FEATURE:
<223> OTHER INFORMATION: Barcoding sequence

<400> SEQUENCE: 160 cggttgaaa 9

<210> SEQ ID NO 161
<211> LENGTH: 9
<212> TYPE: DNA
<213> ORGANISM: Artificial Sequence
<220> FEATURE:
<223> OTHER INFORMATION: Barcoding sequence

<400> SEQUENCE: 161 gcgttgaaa 9

<210> SEQ ID NO 162
<211> LENGTH: 9
<212> TYPE: DNA
<213> ORGANISM: Artificial Sequence -continued
<220> FEATURE:
<223> OTHER INFORMATION: Barcoding sequence

<400> SEQUENCE: 162 ggcttgaaa                                                                   9

<210> SEQ ID NO 163
<211> LENGTH: 9
<212> TYPE: DNA
<213> ORGANISM: Artificial Sequence
<220> FEATURE:
<223> OTHER INFORMATION: Barcoding sequence

<400> SEQUENCE: 163 ccgaacaaa                                                                   9

<210> SEQ ID NO 164
<211> LENGTH: 9
<212> TYPE: DNA
<213> ORGANISM: Artificial Sequence
<220> FEATURE:
<223> OTHER INFORMATION: Barcoding sequence

<400> SEQUENCE: 164 cgcaacaaa                                                                   9

<210> SEQ ID NO 165
<211> LENGTH: 9
<212> TYPE: DNA
<213> ORGANISM: Artificial Sequence
<220> FEATURE:
<223> OTHER INFORMATION: Barcoding sequence

<400> SEQUENCE: 165 gccaacaaa                                                                   9

<210> SEQ ID NO 166
<211> LENGTH: 9
<212> TYPE: DNA
<213> ORGANISM: Artificial Sequence
<220> FEATURE:
<223> OTHER INFORMATION: Barcoding sequence

<400> SEQUENCE: 166 cgagacaaa                                                                   9

<210> SEQ ID NO 167
<211> LENGTH: 9
<212> TYPE: DNA
<213> ORGANISM: Artificial Sequence
<220> FEATURE:
<223> OTHER INFORMATION: Barcoding sequence

<400> SEQUENCE: 167 gcagacaaa                                                                   9

<210> SEQ ID NO 168
<211> LENGTH: 9
<212> TYPE: DNA
<213> ORGANISM: Artificial Sequence
<220> FEATURE:
<223> OTHER INFORMATION: Barcoding sequence

<400> SEQUENCE: 168 caggacaaa                                                                   9

```
<210> SEQ ID NO 169
<211> LENGTH: 9
<212> TYPE: DNA
<213> ORGANISM: Artificial Sequence
<220> FEATURE:
<223> OTHER INFORMATION: Barcoding sequence

<400> SEQUENCE: 169 tcggacaaa                                                                9

<210> SEQ ID NO 170
<211> LENGTH: 9
<212> TYPE: DNA
<213> ORGANISM: Artificial Sequence
<220> FEATURE:
<223> OTHER INFORMATION: Barcoding sequence

<400> SEQUENCE: 170 gtggacaaa                                                                9

<210> SEQ ID NO 171
<211> LENGTH: 9
<212> TYPE: DNA
<213> ORGANISM: Artificial Sequence
<220> FEATURE:
<223> OTHER INFORMATION: Barcoding sequence

<400> SEQUENCE: 171 gacgacaaa                                                                9

<210> SEQ ID NO 172
<211> LENGTH: 9
<212> TYPE: DNA
<213> ORGANISM: Artificial Sequence
<220> FEATURE:
<223> OTHER INFORMATION: Barcoding sequence

<400> SEQUENCE: 172 tgcgacaaa                                                                9

<210> SEQ ID NO 173
<211> LENGTH: 9
<212> TYPE: DNA
<213> ORGANISM: Artificial Sequence
<220> FEATURE:
<223> OTHER INFORMATION: Barcoding sequence

<400> SEQUENCE: 173 accgacaaa                                                                9

<210> SEQ ID NO 174
<211> LENGTH: 9
<212> TYPE: DNA
<213> ORGANISM: Artificial Sequence
<220> FEATURE:
<223> OTHER INFORMATION: Barcoding sequence

<400> SEQUENCE: 174 ctcgacaaa                                                                9

<210> SEQ ID NO 175
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 175 ggtgacaaa                                                          9

<210> SEQ ID NO 176
<211> LENGTH: 9
<212> TYPE: DNA
<213> ORGANISM: Artificial Sequence
<220> FEATURE:
<223> OTHER INFORMATION: Barcoding sequence

<400> SEQUENCE: 176 cctgacaaa                                                          9

<210> SEQ ID NO 177
<211> LENGTH: 9
<212> TYPE: DNA
<213> ORGANISM: Artificial Sequence
<220> FEATURE:
<223> OTHER INFORMATION: Barcoding sequence

<400> SEQUENCE: 177 ggacacaaa                                                          9

<210> SEQ ID NO 178
<211> LENGTH: 9
<212> TYPE: DNA
<213> ORGANISM: Artificial Sequence
<220> FEATURE:
<223> OTHER INFORMATION: Barcoding sequence

<400> SEQUENCE: 178 ccacacaaa                                                          9

<210> SEQ ID NO 179
<211> LENGTH: 9
<212> TYPE: DNA
<213> ORGANISM: Artificial Sequence
<220> FEATURE:
<223> OTHER INFORMATION: Barcoding sequence

<400> SEQUENCE: 179 gagcacaaa                                                          9

<210> SEQ ID NO 180
<211> LENGTH: 9
<212> TYPE: DNA
<213> ORGANISM: Artificial Sequence
<220> FEATURE:
<223> OTHER INFORMATION: Barcoding sequence

<400> SEQUENCE: 180 tggcacaaa                                                          9

<210> SEQ ID NO 181
<211> LENGTH: 9
<212> TYPE: DNA
<213> ORGANISM: Artificial Sequence
<220> FEATURE:
<223> OTHER INFORMATION: Barcoding sequence

<400> SEQUENCE: 181 acgcacaaa                                                          9

<210> SEQ ID NO 182
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 182 ctgcacaaa                                                                    9

<210> SEQ ID NO 183
<211> LENGTH: 9
<212> TYPE: DNA
<213> ORGANISM: Artificial Sequence
<220> FEATURE:
<223> OTHER INFORMATION: Barcoding sequence

<400> SEQUENCE: 183 caccacaaa                                                                    9

<210> SEQ ID NO 184
<211> LENGTH: 9
<212> TYPE: DNA
<213> ORGANISM: Artificial Sequence
<220> FEATURE:
<223> OTHER INFORMATION: Barcoding sequence

<400> SEQUENCE: 184 agccacaaa                                                                    9

<210> SEQ ID NO 185
<211> LENGTH: 9
<212> TYPE: DNA
<213> ORGANISM: Artificial Sequence
<220> FEATURE:
<223> OTHER INFORMATION: Barcoding sequence

<400> SEQUENCE: 185 gtccacaaa                                                                    9

<210> SEQ ID NO 186
<211> LENGTH: 9
<212> TYPE: DNA
<213> ORGANISM: Artificial Sequence
<220> FEATURE:
<223> OTHER INFORMATION: Barcoding sequence

<400> SEQUENCE: 186 cgtcacaaa                                                                    9

<210> SEQ ID NO 187
<211> LENGTH: 9
<212> TYPE: DNA
<213> ORGANISM: Artificial Sequence
<220> FEATURE:
<223> OTHER INFORMATION: Barcoding sequence

<400> SEQUENCE: 187 gctcacaaa                                                                    9

<210> SEQ ID NO 188
<211> LENGTH: 9
<212> TYPE: DNA
<213> ORGANISM: Artificial Sequence
<220> FEATURE:
<223> OTHER INFORMATION: Barcoding sequence

<400> SEQUENCE: 188
```

```
cggtacaaa                                                        9

<210> SEQ ID NO 189
<211> LENGTH: 9
<212> TYPE: DNA
<213> ORGANISM: Artificial Sequence
<220> FEATURE:
<223> OTHER INFORMATION: Barcoding sequence

<400> SEQUENCE: 189 gcgtacaaa                                                        9

<210> SEQ ID NO 190
<211> LENGTH: 9
<212> TYPE: DNA
<213> ORGANISM: Artificial Sequence
<220> FEATURE:
<223> OTHER INFORMATION: Barcoding sequence

<400> SEQUENCE: 190 ggctacaaa                                                        9

<210> SEQ ID NO 191
<211> LENGTH: 9
<212> TYPE: DNA
<213> ORGANISM: Artificial Sequence
<220> FEATURE:
<223> OTHER INFORMATION: Barcoding sequence

<400> SEQUENCE: 191 cgaagcaaa                                                        9

<210> SEQ ID NO 192
<211> LENGTH: 9
<212> TYPE: DNA
<213> ORGANISM: Artificial Sequence
<220> FEATURE:
<223> OTHER INFORMATION: Barcoding sequence

<400> SEQUENCE: 192 gcaagcaaa                                                        9

<210> SEQ ID NO 193
<211> LENGTH: 9
<212> TYPE: DNA
<213> ORGANISM: Artificial Sequence
<220> FEATURE:
<223> OTHER INFORMATION: Barcoding sequence

<400> SEQUENCE: 193 cagagcaaa                                                        9

<210> SEQ ID NO 194
<211> LENGTH: 9
<212> TYPE: DNA
<213> ORGANISM: Artificial Sequence
<220> FEATURE:
<223> OTHER INFORMATION: Barcoding sequence

<400> SEQUENCE: 194 tggagcaaa                                                        9

<210> SEQ ID NO 195
<211> LENGTH: 9
<212> TYPE: DNA
```

<213> ORGANISM: Artificial Sequence
<220> FEATURE:
<223> OTHER INFORMATION: Barcoding sequence

<400> SEQUENCE: 195 acgagcaaa                                                                    9

<210> SEQ ID NO 196
<211> LENGTH: 9
<212> TYPE: DNA
<213> ORGANISM: Artificial Sequence
<220> FEATURE:
<223> OTHER INFORMATION: Barcoding sequence

<400> SEQUENCE: 196 gtgagcaaa                                                                    9

<210> SEQ ID NO 197
<211> LENGTH: 9
<212> TYPE: DNA
<213> ORGANISM: Artificial Sequence
<220> FEATURE:
<223> OTHER INFORMATION: Barcoding sequence

<400> SEQUENCE: 197 gacagcaaa                                                                    9

<210> SEQ ID NO 198
<211> LENGTH: 9
<212> TYPE: DNA
<213> ORGANISM: Artificial Sequence
<220> FEATURE:
<223> OTHER INFORMATION: Barcoding sequence

<400> SEQUENCE: 198 agcagcaaa                                                                    9

<210> SEQ ID NO 199
<211> LENGTH: 9
<212> TYPE: DNA
<213> ORGANISM: Artificial Sequence
<220> FEATURE:
<223> OTHER INFORMATION: Barcoding sequence

<400> SEQUENCE: 199 tccagcaaa                                                                    9

<210> SEQ ID NO 200
<211> LENGTH: 9
<212> TYPE: DNA
<213> ORGANISM: Artificial Sequence
<220> FEATURE:
<223> OTHER INFORMATION: Barcoding sequence

<400> SEQUENCE: 200 ctcagcaaa                                                                    9

<210> SEQ ID NO 201
<211> LENGTH: 9
<212> TYPE: DNA
<213> ORGANISM: Artificial Sequence
<220> FEATURE:
<223> OTHER INFORMATION: Barcoding sequence

<400> SEQUENCE: 201 ggtagcaaa                                                                    9

<210> SEQ ID NO 202
<211> LENGTH: 9
<212> TYPE: DNA
<213> ORGANISM: Artificial Sequence
<220> FEATURE:
<223> OTHER INFORMATION: Barcoding sequence

<400> SEQUENCE: 202 cctagcaaa                                                                9

<210> SEQ ID NO 203
<211> LENGTH: 9
<212> TYPE: DNA
<213> ORGANISM: Artificial Sequence
<220> FEATURE:
<223> OTHER INFORMATION: Barcoding sequence

<400> SEQUENCE: 203 gaaggcaaa                                                                9

<210> SEQ ID NO 204
<211> LENGTH: 9
<212> TYPE: DNA
<213> ORGANISM: Artificial Sequence
<220> FEATURE:
<223> OTHER INFORMATION: Barcoding sequence

<400> SEQUENCE: 204 agaggcaaa                                                                9

<210> SEQ ID NO 205
<211> LENGTH: 9
<212> TYPE: DNA
<213> ORGANISM: Artificial Sequence
<220> FEATURE:
<223> OTHER INFORMATION: Barcoding sequence

<400> SEQUENCE: 205 tcaggcaaa                                                                9

<210> SEQ ID NO 206
<211> LENGTH: 9
<212> TYPE: DNA
<213> ORGANISM: Artificial Sequence
<220> FEATURE:
<223> OTHER INFORMATION: Barcoding sequence

<400> SEQUENCE: 206 ctaggcaaa                                                                9

<210> SEQ ID NO 207
<211> LENGTH: 9
<212> TYPE: DNA
<213> ORGANISM: Artificial Sequence
<220> FEATURE:
<223> OTHER INFORMATION: Barcoding sequence

<400> SEQUENCE: 207 aacggcaaa                                                                9

<210> SEQ ID NO 208
<211> LENGTH: 9
<212> TYPE: DNA
<213> ORGANISM: Artificial Sequence
<220> FEATURE:

<223> OTHER INFORMATION: Barcoding sequence

<400> SEQUENCE: 208 ttcggcaaa                                                                              9

<210> SEQ ID NO 209
<211> LENGTH: 9
<212> TYPE: DNA
<213> ORGANISM: Artificial Sequence
<220> FEATURE:
<223> OTHER INFORMATION: Barcoding sequence

<400> SEQUENCE: 209 catggcaaa                                                                              9

<210> SEQ ID NO 210
<211> LENGTH: 9
<212> TYPE: DNA
<213> ORGANISM: Artificial Sequence
<220> FEATURE:
<223> OTHER INFORMATION: Barcoding sequence

<400> SEQUENCE: 210 tgtggcaaa                                                                              9

<210> SEQ ID NO 211
<211> LENGTH: 9
<212> TYPE: DNA
<213> ORGANISM: Artificial Sequence
<220> FEATURE:
<223> OTHER INFORMATION: Barcoding sequence

<400> SEQUENCE: 211 actggcaaa                                                                              9

<210> SEQ ID NO 212
<211> LENGTH: 9
<212> TYPE: DNA
<213> ORGANISM: Artificial Sequence
<220> FEATURE:
<223> OTHER INFORMATION: Barcoding sequence

<400> SEQUENCE: 212 gttggcaaa                                                                              9

<210> SEQ ID NO 213
<211> LENGTH: 9
<212> TYPE: DNA
<213> ORGANISM: Artificial Sequence
<220> FEATURE:
<223> OTHER INFORMATION: Barcoding sequence

<400> SEQUENCE: 213 caacgcaaa                                                                              9

<210> SEQ ID NO 214
<211> LENGTH: 9
<212> TYPE: DNA
<213> ORGANISM: Artificial Sequence
<220> FEATURE:
<223> OTHER INFORMATION: Barcoding sequence

<400> SEQUENCE: 214 tgacgcaaa                                                                              9

```
<210> SEQ ID NO 215
<211> LENGTH: 9
<212> TYPE: DNA
<213> ORGANISM: Artificial Sequence
<220> FEATURE:
<223> OTHER INFORMATION: Barcoding sequence

<400> SEQUENCE: 215 acacgcaaa                                                                  9

<210> SEQ ID NO 216
<211> LENGTH: 9
<212> TYPE: DNA
<213> ORGANISM: Artificial Sequence
<220> FEATURE:
<223> OTHER INFORMATION: Barcoding sequence

<400> SEQUENCE: 216 gtacgcaaa                                                                  9

<210> SEQ ID NO 217
<211> LENGTH: 9
<212> TYPE: DNA
<213> ORGANISM: Artificial Sequence
<220> FEATURE:
<223> OTHER INFORMATION: Barcoding sequence

<400> SEQUENCE: 217 tagcgcaaa                                                                  9

<210> SEQ ID NO 218
<211> LENGTH: 9
<212> TYPE: DNA
<213> ORGANISM: Artificial Sequence
<220> FEATURE:
<223> OTHER INFORMATION: Barcoding sequence

<400> SEQUENCE: 218 atgcgcaaa                                                                  9

<210> SEQ ID NO 219
<211> LENGTH: 9
<212> TYPE: DNA
<213> ORGANISM: Artificial Sequence
<220> FEATURE:
<223> OTHER INFORMATION: Barcoding sequence

<400> SEQUENCE: 219 gatcgcaaa                                                                  9

<210> SEQ ID NO 220
<211> LENGTH: 9
<212> TYPE: DNA
<213> ORGANISM: Artificial Sequence
<220> FEATURE:
<223> OTHER INFORMATION: Barcoding sequence

<400> SEQUENCE: 220 agtcgcaaa                                                                  9

<210> SEQ ID NO 221
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 221 tctcgcaaa                                                                 9

<210> SEQ ID NO 222
<211> LENGTH: 9
<212> TYPE: DNA
<213> ORGANISM: Artificial Sequence
<220> FEATURE:
<223> OTHER INFORMATION: Barcoding sequence

<400> SEQUENCE: 222 cttcgcaaa                                                                 9

<210> SEQ ID NO 223
<211> LENGTH: 9
<212> TYPE: DNA
<213> ORGANISM: Artificial Sequence
<220> FEATURE:
<223> OTHER INFORMATION: Barcoding sequence

<400> SEQUENCE: 223 ggatgcaaa                                                                 9

<210> SEQ ID NO 224
<211> LENGTH: 9
<212> TYPE: DNA
<213> ORGANISM: Artificial Sequence
<220> FEATURE:
<223> OTHER INFORMATION: Barcoding sequence

<400> SEQUENCE: 224 ccatgcaaa                                                                 9

<210> SEQ ID NO 225
<211> LENGTH: 9
<212> TYPE: DNA
<213> ORGANISM: Artificial Sequence
<220> FEATURE:
<223> OTHER INFORMATION: Barcoding sequence

<400> SEQUENCE: 225 gagtgcaaa                                                                 9

<210> SEQ ID NO 226
<211> LENGTH: 9
<212> TYPE: DNA
<213> ORGANISM: Artificial Sequence
<220> FEATURE:
<223> OTHER INFORMATION: Barcoding sequence

<400> SEQUENCE: 226 aggtgcaaa                                                                 9

<210> SEQ ID NO 227
<211> LENGTH: 9
<212> TYPE: DNA
<213> ORGANISM: Artificial Sequence
<220> FEATURE:
<223> OTHER INFORMATION: Barcoding sequence

<400> SEQUENCE: 227 tcgtgcaaa                                                                 9

<210> SEQ ID NO 228
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 228 ctgtgcaaa                                                                     9

<210> SEQ ID NO 229
<211> LENGTH: 9
<212> TYPE: DNA
<213> ORGANISM: Artificial Sequence
<220> FEATURE:
<223> OTHER INFORMATION: Barcoding sequence

<400> SEQUENCE: 229 cactgcaaa                                                                     9

<210> SEQ ID NO 230
<211> LENGTH: 9
<212> TYPE: DNA
<213> ORGANISM: Artificial Sequence
<220> FEATURE:
<223> OTHER INFORMATION: Barcoding sequence

<400> SEQUENCE: 230 tgctgcaaa                                                                     9

<210> SEQ ID NO 231
<211> LENGTH: 9
<212> TYPE: DNA
<213> ORGANISM: Artificial Sequence
<220> FEATURE:
<223> OTHER INFORMATION: Barcoding sequence

<400> SEQUENCE: 231 acctgcaaa                                                                     9

<210> SEQ ID NO 232
<211> LENGTH: 9
<212> TYPE: DNA
<213> ORGANISM: Artificial Sequence
<220> FEATURE:
<223> OTHER INFORMATION: Barcoding sequence

<400> SEQUENCE: 232 gtctgcaaa                                                                     9

<210> SEQ ID NO 233
<211> LENGTH: 9
<212> TYPE: DNA
<213> ORGANISM: Artificial Sequence
<220> FEATURE:
<223> OTHER INFORMATION: Barcoding sequence

<400> SEQUENCE: 233 cgttgcaaa                                                                     9

<210> SEQ ID NO 234
<211> LENGTH: 9
<212> TYPE: DNA
<213> ORGANISM: Artificial Sequence
<220> FEATURE:
<223> OTHER INFORMATION: Barcoding sequence

<400> SEQUENCE: 234
``` gcttgcaaa 9

<210> SEQ ID NO 235
<211> LENGTH: 9
<212> TYPE: DNA
<213> ORGANISM: Artificial Sequence
<220> FEATURE:
<223> OTHER INFORMATION: Barcoding sequence

<400> SEQUENCE: 235 ggaaccaaa 9

<210> SEQ ID NO 236
<211> LENGTH: 9
<212> TYPE: DNA
<213> ORGANISM: Artificial Sequence
<220> FEATURE:
<223> OTHER INFORMATION: Barcoding sequence

<400> SEQUENCE: 236 ccaaccaaa 9

<210> SEQ ID NO 237
<211> LENGTH: 9
<212> TYPE: DNA
<213> ORGANISM: Artificial Sequence
<220> FEATURE:
<223> OTHER INFORMATION: Barcoding sequence

<400> SEQUENCE: 237 gagaccaaa 9

<210> SEQ ID NO 238
<211> LENGTH: 9
<212> TYPE: DNA
<213> ORGANISM: Artificial Sequence
<220> FEATURE:
<223> OTHER INFORMATION: Barcoding sequence

<400> SEQUENCE: 238 aggaccaaa 9

<210> SEQ ID NO 239
<211> LENGTH: 9
<212> TYPE: DNA
<213> ORGANISM: Artificial Sequence
<220> FEATURE:
<223> OTHER INFORMATION: Barcoding sequence

<400> SEQUENCE: 239 tcgaccaaa 9

<210> SEQ ID NO 240
<211> LENGTH: 9
<212> TYPE: DNA
<213> ORGANISM: Artificial Sequence
<220> FEATURE:
<223> OTHER INFORMATION: Barcoding sequence

<400> SEQUENCE: 240 ctgaccaaa 9

<210> SEQ ID NO 241
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 241 cacaccaaa                                                                 9

<210> SEQ ID NO 242
<211> LENGTH: 9
<212> TYPE: DNA
<213> ORGANISM: Artificial Sequence
<220> FEATURE:
<223> OTHER INFORMATION: Barcoding sequence

<400> SEQUENCE: 242 tgcaccaaa                                                                 9

<210> SEQ ID NO 243
<211> LENGTH: 9
<212> TYPE: DNA
<213> ORGANISM: Artificial Sequence
<220> FEATURE:
<223> OTHER INFORMATION: Barcoding sequence

<400> SEQUENCE: 243 accaccaaa                                                                 9

<210> SEQ ID NO 244
<211> LENGTH: 9
<212> TYPE: DNA
<213> ORGANISM: Artificial Sequence
<220> FEATURE:
<223> OTHER INFORMATION: Barcoding sequence

<400> SEQUENCE: 244 gtcaccaaa                                                                 9

<210> SEQ ID NO 245
<211> LENGTH: 9
<212> TYPE: DNA
<213> ORGANISM: Artificial Sequence
<220> FEATURE:
<223> OTHER INFORMATION: Barcoding sequence

<400> SEQUENCE: 245 cgtaccaaa                                                                 9

<210> SEQ ID NO 246
<211> LENGTH: 9
<212> TYPE: DNA
<213> ORGANISM: Artificial Sequence
<220> FEATURE:
<223> OTHER INFORMATION: Barcoding sequence

<400> SEQUENCE: 246 gctaccaaa                                                                 9

<210> SEQ ID NO 247
<211> LENGTH: 9
<212> TYPE: DNA
<213> ORGANISM: Artificial Sequence
<220> FEATURE:
<223> OTHER INFORMATION: Barcoding sequence

<400> SEQUENCE: 247 caagccaaa                                                                 9
```

```
<210> SEQ ID NO 248
<211> LENGTH: 9
<212> TYPE: DNA
<213> ORGANISM: Artificial Sequence
<220> FEATURE:
<223> OTHER INFORMATION: Barcoding sequence

<400> SEQUENCE: 248 tgagccaaa                                                           9

<210> SEQ ID NO 249
<211> LENGTH: 9
<212> TYPE: DNA
<213> ORGANISM: Artificial Sequence
<220> FEATURE:
<223> OTHER INFORMATION: Barcoding sequence

<400> SEQUENCE: 249 acagccaaa                                                           9

<210> SEQ ID NO 250
<211> LENGTH: 9
<212> TYPE: DNA
<213> ORGANISM: Artificial Sequence
<220> FEATURE:
<223> OTHER INFORMATION: Barcoding sequence

<400> SEQUENCE: 250 gtagccaaa                                                           9

<210> SEQ ID NO 251
<211> LENGTH: 9
<212> TYPE: DNA
<213> ORGANISM: Artificial Sequence
<220> FEATURE:
<223> OTHER INFORMATION: Barcoding sequence

<400> SEQUENCE: 251 taggccaaa                                                           9

<210> SEQ ID NO 252
<211> LENGTH: 9
<212> TYPE: DNA
<213> ORGANISM: Artificial Sequence
<220> FEATURE:
<223> OTHER INFORMATION: Barcoding sequence

<400> SEQUENCE: 252 atggccaaa                                                           9

<210> SEQ ID NO 253
<211> LENGTH: 9
<212> TYPE: DNA
<213> ORGANISM: Artificial Sequence
<220> FEATURE:
<223> OTHER INFORMATION: Barcoding sequence

<400> SEQUENCE: 253 gatgccaaa                                                           9

<210> SEQ ID NO 254
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 254 agtgccaaa                                                              9

<210> SEQ ID NO 255
<211> LENGTH: 9
<212> TYPE: DNA
<213> ORGANISM: Artificial Sequence
<220> FEATURE:
<223> OTHER INFORMATION: Barcoding sequence

<400> SEQUENCE: 255 tctgccaaa                                                              9

<210> SEQ ID NO 256
<211> LENGTH: 9
<212> TYPE: DNA
<213> ORGANISM: Artificial Sequence
<220> FEATURE:
<223> OTHER INFORMATION: Barcoding sequence

<400> SEQUENCE: 256 cttgccaaa                                                              9

<210> SEQ ID NO 257
<211> LENGTH: 9
<212> TYPE: DNA
<213> ORGANISM: Artificial Sequence
<220> FEATURE:
<223> OTHER INFORMATION: Barcoding sequence

<400> SEQUENCE: 257 cgatccaaa                                                              9

<210> SEQ ID NO 258
<211> LENGTH: 9
<212> TYPE: DNA
<213> ORGANISM: Artificial Sequence
<220> FEATURE:
<223> OTHER INFORMATION: Barcoding sequence

<400> SEQUENCE: 258 gcatccaaa                                                              9

<210> SEQ ID NO 259
<211> LENGTH: 9
<212> TYPE: DNA
<213> ORGANISM: Artificial Sequence
<220> FEATURE:
<223> OTHER INFORMATION: Barcoding sequence

<400> SEQUENCE: 259 cagtccaaa                                                              9

<210> SEQ ID NO 260
<211> LENGTH: 9
<212> TYPE: DNA
<213> ORGANISM: Artificial Sequence
<220> FEATURE:
<223> OTHER INFORMATION: Barcoding sequence

<400> SEQUENCE: 260 tggtccaaa                                                              9

<210> SEQ ID NO 261
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 261 acgtccaaa                                                                9

<210> SEQ ID NO 262
<211> LENGTH: 9
<212> TYPE: DNA
<213> ORGANISM: Artificial Sequence
<220> FEATURE:
<223> OTHER INFORMATION: Barcoding sequence

<400> SEQUENCE: 262 gtgtccaaa                                                                9

<210> SEQ ID NO 263
<211> LENGTH: 9
<212> TYPE: DNA
<213> ORGANISM: Artificial Sequence
<220> FEATURE:
<223> OTHER INFORMATION: Barcoding sequence

<400> SEQUENCE: 263 gactccaaa                                                                9

<210> SEQ ID NO 264
<211> LENGTH: 9
<212> TYPE: DNA
<213> ORGANISM: Artificial Sequence
<220> FEATURE:
<223> OTHER INFORMATION: Barcoding sequence

<400> SEQUENCE: 264 agctccaaa                                                                9

<210> SEQ ID NO 265
<211> LENGTH: 9
<212> TYPE: DNA
<213> ORGANISM: Artificial Sequence
<220> FEATURE:
<223> OTHER INFORMATION: Barcoding sequence

<400> SEQUENCE: 265 tcctccaaa                                                                9

<210> SEQ ID NO 266
<211> LENGTH: 9
<212> TYPE: DNA
<213> ORGANISM: Artificial Sequence
<220> FEATURE:
<223> OTHER INFORMATION: Barcoding sequence

<400> SEQUENCE: 266 ctctccaaa                                                                9

<210> SEQ ID NO 267
<211> LENGTH: 9
<212> TYPE: DNA
<213> ORGANISM: Artificial Sequence
<220> FEATURE:
<223> OTHER INFORMATION: Barcoding sequence

<400> SEQUENCE: 267
``` ggttccaaa                                                                           9

<210> SEQ ID NO 268
<211> LENGTH: 9
<212> TYPE: DNA
<213> ORGANISM: Artificial Sequence
<220> FEATURE:
<223> OTHER INFORMATION: Barcoding sequence

<400> SEQUENCE: 268 ccttccaaa                                                                           9

<210> SEQ ID NO 269
<211> LENGTH: 9
<212> TYPE: DNA
<213> ORGANISM: Artificial Sequence
<220> FEATURE:
<223> OTHER INFORMATION: Barcoding sequence

<400> SEQUENCE: 269 cggatcaaa                                                                           9

<210> SEQ ID NO 270
<211> LENGTH: 9
<212> TYPE: DNA
<213> ORGANISM: Artificial Sequence
<220> FEATURE:
<223> OTHER INFORMATION: Barcoding sequence

<400> SEQUENCE: 270 gcgatcaaa                                                                           9

<210> SEQ ID NO 271
<211> LENGTH: 9
<212> TYPE: DNA
<213> ORGANISM: Artificial Sequence
<220> FEATURE:
<223> OTHER INFORMATION: Barcoding sequence

<400> SEQUENCE: 271 ggcatcaaa                                                                           9

<210> SEQ ID NO 272
<211> LENGTH: 9
<212> TYPE: DNA
<213> ORGANISM: Artificial Sequence
<220> FEATURE:
<223> OTHER INFORMATION: Barcoding sequence

<400> SEQUENCE: 272 ggagtcaaa                                                                           9

<210> SEQ ID NO 273
<211> LENGTH: 9
<212> TYPE: DNA
<213> ORGANISM: Artificial Sequence
<220> FEATURE:
<223> OTHER INFORMATION: Barcoding sequence

<400> SEQUENCE: 273 ccagtcaaa                                                                           9

<210> SEQ ID NO 274
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 274 gaggtcaaa                                                                    9

<210> SEQ ID NO 275
<211> LENGTH: 9
<212> TYPE: DNA
<213> ORGANISM: Artificial Sequence
<220> FEATURE:
<223> OTHER INFORMATION: Barcoding sequence

<400> SEQUENCE: 275 acggtcaaa                                                                    9

<210> SEQ ID NO 276
<211> LENGTH: 9
<212> TYPE: DNA
<213> ORGANISM: Artificial Sequence
<220> FEATURE:
<223> OTHER INFORMATION: Barcoding sequence

<400> SEQUENCE: 276 ctggtcaaa                                                                    9

<210> SEQ ID NO 277
<211> LENGTH: 9
<212> TYPE: DNA
<213> ORGANISM: Artificial Sequence
<220> FEATURE:
<223> OTHER INFORMATION: Barcoding sequence

<400> SEQUENCE: 277 cacgtcaaa                                                                    9

<210> SEQ ID NO 278
<211> LENGTH: 9
<212> TYPE: DNA
<213> ORGANISM: Artificial Sequence
<220> FEATURE:
<223> OTHER INFORMATION: Barcoding sequence

<400> SEQUENCE: 278 agcgtcaaa                                                                    9

<210> SEQ ID NO 279
<211> LENGTH: 9
<212> TYPE: DNA
<213> ORGANISM: Artificial Sequence
<220> FEATURE:
<223> OTHER INFORMATION: Barcoding sequence

<400> SEQUENCE: 279 tccgtcaaa                                                                    9

<210> SEQ ID NO 280
<211> LENGTH: 9
<212> TYPE: DNA
<213> ORGANISM: Artificial Sequence
<220> FEATURE:
<223> OTHER INFORMATION: Barcoding sequence

<400> SEQUENCE: 280 gtcgtcaaa                                                                    9
```

```
<210> SEQ ID NO 281
<211> LENGTH: 9
<212> TYPE: DNA
<213> ORGANISM: Artificial Sequence
<220> FEATURE:
<223> OTHER INFORMATION: Barcoding sequence

<400> SEQUENCE: 281 cgtgtcaaa                                                                   9

<210> SEQ ID NO 282
<211> LENGTH: 9
<212> TYPE: DNA
<213> ORGANISM: Artificial Sequence
<220> FEATURE:
<223> OTHER INFORMATION: Barcoding sequence

<400> SEQUENCE: 282 gctgtcaaa                                                                   9

<210> SEQ ID NO 283
<211> LENGTH: 9
<212> TYPE: DNA
<213> ORGANISM: Artificial Sequence
<220> FEATURE:
<223> OTHER INFORMATION: Barcoding sequence

<400> SEQUENCE: 283 cgactcaaa                                                                   9

<210> SEQ ID NO 284
<211> LENGTH: 9
<212> TYPE: DNA
<213> ORGANISM: Artificial Sequence
<220> FEATURE:
<223> OTHER INFORMATION: Barcoding sequence

<400> SEQUENCE: 284 gcactcaaa                                                                   9

<210> SEQ ID NO 285
<211> LENGTH: 9
<212> TYPE: DNA
<213> ORGANISM: Artificial Sequence
<220> FEATURE:
<223> OTHER INFORMATION: Barcoding sequence

<400> SEQUENCE: 285 cagctcaaa                                                                   9

<210> SEQ ID NO 286
<211> LENGTH: 9
<212> TYPE: DNA
<213> ORGANISM: Artificial Sequence
<220> FEATURE:
<223> OTHER INFORMATION: Barcoding sequence

<400> SEQUENCE: 286 aggctcaaa                                                                   9

<210> SEQ ID NO 287
<211> LENGTH: 9
<212> TYPE: DNA
<213> ORGANISM: Artificial Sequence
<220> FEATURE:
```

```
<223> OTHER INFORMATION: Barcoding sequence

<400> SEQUENCE: 287 tcgctcaaa                                                                 9

<210> SEQ ID NO 288
<211> LENGTH: 9
<212> TYPE: DNA
<213> ORGANISM: Artificial Sequence
<220> FEATURE:
<223> OTHER INFORMATION: Barcoding sequence

<400> SEQUENCE: 288 gtgctcaaa                                                                 9

<210> SEQ ID NO 289
<211> LENGTH: 9
<212> TYPE: DNA
<213> ORGANISM: Artificial Sequence
<220> FEATURE:
<223> OTHER INFORMATION: Barcoding sequence

<400> SEQUENCE: 289 gacctcaaa                                                                 9

<210> SEQ ID NO 290
<211> LENGTH: 9
<212> TYPE: DNA
<213> ORGANISM: Artificial Sequence
<220> FEATURE:
<223> OTHER INFORMATION: Barcoding sequence

<400> SEQUENCE: 290 tgcctcaaa                                                                 9

<210> SEQ ID NO 291
<211> LENGTH: 9
<212> TYPE: DNA
<213> ORGANISM: Artificial Sequence
<220> FEATURE:
<223> OTHER INFORMATION: Barcoding sequence

<400> SEQUENCE: 291 ctcctcaaa                                                                 9

<210> SEQ ID NO 292
<211> LENGTH: 9
<212> TYPE: DNA
<213> ORGANISM: Artificial Sequence
<220> FEATURE:
<223> OTHER INFORMATION: Barcoding sequence

<400> SEQUENCE: 292 ggtctcaaa                                                                 9

<210> SEQ ID NO 293
<211> LENGTH: 9
<212> TYPE: DNA
<213> ORGANISM: Artificial Sequence
<220> FEATURE:
<223> OTHER INFORMATION: Barcoding sequence

<400> SEQUENCE: 293 cctctcaaa                                                                 9
```

```
<210> SEQ ID NO 294
<211> LENGTH: 9
<212> TYPE: DNA
<213> ORGANISM: Artificial Sequence
<220> FEATURE:
<223> OTHER INFORMATION: Barcoding sequence

<400> SEQUENCE: 294 ccgttcaaa                                                                 9

<210> SEQ ID NO 295
<211> LENGTH: 9
<212> TYPE: DNA
<213> ORGANISM: Artificial Sequence
<220> FEATURE:
<223> OTHER INFORMATION: Barcoding sequence

<400> SEQUENCE: 295 cgcttcaaa                                                                 9

<210> SEQ ID NO 296
<211> LENGTH: 9
<212> TYPE: DNA
<213> ORGANISM: Artificial Sequence
<220> FEATURE:
<223> OTHER INFORMATION: Barcoding sequence

<400> SEQUENCE: 296 gccttcaaa                                                                 9

<210> SEQ ID NO 297
<211> LENGTH: 9
<212> TYPE: DNA
<213> ORGANISM: Artificial Sequence
<220> FEATURE:
<223> OTHER INFORMATION: Barcoding sequence

<400> SEQUENCE: 297 gcggataaa                                                                 9

<210> SEQ ID NO 298
<211> LENGTH: 9
<212> TYPE: DNA
<213> ORGANISM: Artificial Sequence
<220> FEATURE:
<223> OTHER INFORMATION: Barcoding sequence

<400> SEQUENCE: 298 ggcgataaa                                                                 9

<210> SEQ ID NO 299
<211> LENGTH: 9
<212> TYPE: DNA
<213> ORGANISM: Artificial Sequence
<220> FEATURE:
<223> OTHER INFORMATION: Barcoding sequence

<400> SEQUENCE: 299 cggcataaa                                                                 9

<210> SEQ ID NO 300
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 300 cggagtaaa                                                              9

<210> SEQ ID NO 301
<211> LENGTH: 9
<212> TYPE: DNA
<213> ORGANISM: Artificial Sequence
<220> FEATURE:
<223> OTHER INFORMATION: Barcoding sequence

<400> SEQUENCE: 301 gcgagtaaa                                                              9

<210> SEQ ID NO 302
<211> LENGTH: 9
<212> TYPE: DNA
<213> ORGANISM: Artificial Sequence
<220> FEATURE:
<223> OTHER INFORMATION: Barcoding sequence

<400> SEQUENCE: 302 ggcagtaaa                                                              9

<210> SEQ ID NO 303
<211> LENGTH: 9
<212> TYPE: DNA
<213> ORGANISM: Artificial Sequence
<220> FEATURE:
<223> OTHER INFORMATION: Barcoding sequence

<400> SEQUENCE: 303 ggaggtaaa                                                              9

<210> SEQ ID NO 304
<211> LENGTH: 9
<212> TYPE: DNA
<213> ORGANISM: Artificial Sequence
<220> FEATURE:
<223> OTHER INFORMATION: Barcoding sequence

<400> SEQUENCE: 304 ccaggtaaa                                                              9

<210> SEQ ID NO 305
<211> LENGTH: 9
<212> TYPE: DNA
<213> ORGANISM: Artificial Sequence
<220> FEATURE:
<223> OTHER INFORMATION: Barcoding sequence

<400> SEQUENCE: 305 gacggtaaa                                                              9

<210> SEQ ID NO 306
<211> LENGTH: 9
<212> TYPE: DNA
<213> ORGANISM: Artificial Sequence
<220> FEATURE:
<223> OTHER INFORMATION: Barcoding sequence

<400> SEQUENCE: 306 agcggtaaa                                                              9

<210> SEQ ID NO 307
<211> LENGTH: 9
```

-continued

<212> TYPE: DNA
<213> ORGANISM: Artificial Sequence
<220> FEATURE:
<223> OTHER INFORMATION: Barcoding sequence

<400> SEQUENCE: 307 tccggtaaa                                                                 9

<210> SEQ ID NO 308
<211> LENGTH: 9
<212> TYPE: DNA
<213> ORGANISM: Artificial Sequence
<220> FEATURE:
<223> OTHER INFORMATION: Barcoding sequence

<400> SEQUENCE: 308 ctcggtaaa                                                                 9

<210> SEQ ID NO 309
<211> LENGTH: 9
<212> TYPE: DNA
<213> ORGANISM: Artificial Sequence
<220> FEATURE:
<223> OTHER INFORMATION: Barcoding sequence

<400> SEQUENCE: 309 cgtggtaaa                                                                 9

<210> SEQ ID NO 310
<211> LENGTH: 9
<212> TYPE: DNA
<213> ORGANISM: Artificial Sequence
<220> FEATURE:
<223> OTHER INFORMATION: Barcoding sequence

<400> SEQUENCE: 310 gctggtaaa                                                                 9

<210> SEQ ID NO 311
<211> LENGTH: 9
<212> TYPE: DNA
<213> ORGANISM: Artificial Sequence
<220> FEATURE:
<223> OTHER INFORMATION: Barcoding sequence

<400> SEQUENCE: 311 cgacgtaaa                                                                 9

<210> SEQ ID NO 312
<211> LENGTH: 9
<212> TYPE: DNA
<213> ORGANISM: Artificial Sequence
<220> FEATURE:
<223> OTHER INFORMATION: Barcoding sequence

<400> SEQUENCE: 312 gcacgtaaa                                                                 9

<210> SEQ ID NO 313
<211> LENGTH: 9
<212> TYPE: DNA
<213> ORGANISM: Artificial Sequence
<220> FEATURE:
<223> OTHER INFORMATION: Barcoding sequence

<400> SEQUENCE: 313 gagcgtaaa                                                              9

<210> SEQ ID NO 314
<211> LENGTH: 9
<212> TYPE: DNA
<213> ORGANISM: Artificial Sequence
<220> FEATURE:
<223> OTHER INFORMATION: Barcoding sequence

<400> SEQUENCE: 314 aggcgtaaa                                                              9

<210> SEQ ID NO 315
<211> LENGTH: 9
<212> TYPE: DNA
<213> ORGANISM: Artificial Sequence
<220> FEATURE:
<223> OTHER INFORMATION: Barcoding sequence

<400> SEQUENCE: 315 tcgcgtaaa                                                              9

<210> SEQ ID NO 316
<211> LENGTH: 9
<212> TYPE: DNA
<213> ORGANISM: Artificial Sequence
<220> FEATURE:
<223> OTHER INFORMATION: Barcoding sequence

<400> SEQUENCE: 316 ctgcgtaaa                                                              9

<210> SEQ ID NO 317
<211> LENGTH: 9
<212> TYPE: DNA
<213> ORGANISM: Artificial Sequence
<220> FEATURE:
<223> OTHER INFORMATION: Barcoding sequence

<400> SEQUENCE: 317 caccgtaaa                                                              9

<210> SEQ ID NO 318
<211> LENGTH: 9
<212> TYPE: DNA
<213> ORGANISM: Artificial Sequence
<220> FEATURE:
<223> OTHER INFORMATION: Barcoding sequence

<400> SEQUENCE: 318 tgccgtaaa                                                              9

<210> SEQ ID NO 319
<211> LENGTH: 9
<212> TYPE: DNA
<213> ORGANISM: Artificial Sequence
<220> FEATURE:
<223> OTHER INFORMATION: Barcoding sequence

<400> SEQUENCE: 319 gtccgtaaa                                                              9

<210> SEQ ID NO 320
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 320 ggtcgtaaa                                                                9

<210> SEQ ID NO 321
<211> LENGTH: 9
<212> TYPE: DNA
<213> ORGANISM: Artificial Sequence
<220> FEATURE:
<223> OTHER INFORMATION: Barcoding sequence

<400> SEQUENCE: 321 cctcgtaaa                                                                9

<210> SEQ ID NO 322
<211> LENGTH: 9
<212> TYPE: DNA
<213> ORGANISM: Artificial Sequence
<220> FEATURE:
<223> OTHER INFORMATION: Barcoding sequence

<400> SEQUENCE: 322 ccgtgtaaa                                                                9

<210> SEQ ID NO 323
<211> LENGTH: 9
<212> TYPE: DNA
<213> ORGANISM: Artificial Sequence
<220> FEATURE:
<223> OTHER INFORMATION: Barcoding sequence

<400> SEQUENCE: 323 cgctgtaaa                                                                9

<210> SEQ ID NO 324
<211> LENGTH: 9
<212> TYPE: DNA
<213> ORGANISM: Artificial Sequence
<220> FEATURE:
<223> OTHER INFORMATION: Barcoding sequence

<400> SEQUENCE: 324 gcctgtaaa                                                                9

<210> SEQ ID NO 325
<211> LENGTH: 9
<212> TYPE: DNA
<213> ORGANISM: Artificial Sequence
<220> FEATURE:
<223> OTHER INFORMATION: Barcoding sequence

<400> SEQUENCE: 325 ccgactaaa                                                                9

<210> SEQ ID NO 326
<211> LENGTH: 9
<212> TYPE: DNA
<213> ORGANISM: Artificial Sequence
<220> FEATURE:
<223> OTHER INFORMATION: Barcoding sequence

<400> SEQUENCE: 326 cgcactaaa                                                                9
```

```
<210> SEQ ID NO 327
<211> LENGTH: 9
<212> TYPE: DNA
<213> ORGANISM: Artificial Sequence
<220> FEATURE:
<223> OTHER INFORMATION: Barcoding sequence

<400> SEQUENCE: 327 gccactaaa                                                                  9

<210> SEQ ID NO 328
<211> LENGTH: 9
<212> TYPE: DNA
<213> ORGANISM: Artificial Sequence
<220> FEATURE:
<223> OTHER INFORMATION: Barcoding sequence

<400> SEQUENCE: 328 cgagctaaa                                                                  9

<210> SEQ ID NO 329
<211> LENGTH: 9
<212> TYPE: DNA
<213> ORGANISM: Artificial Sequence
<220> FEATURE:
<223> OTHER INFORMATION: Barcoding sequence

<400> SEQUENCE: 329 gcagctaaa                                                                  9

<210> SEQ ID NO 330
<211> LENGTH: 9
<212> TYPE: DNA
<213> ORGANISM: Artificial Sequence
<220> FEATURE:
<223> OTHER INFORMATION: Barcoding sequence

<400> SEQUENCE: 330 gaggctaaa                                                                  9

<210> SEQ ID NO 331
<211> LENGTH: 9
<212> TYPE: DNA
<213> ORGANISM: Artificial Sequence
<220> FEATURE:
<223> OTHER INFORMATION: Barcoding sequence

<400> SEQUENCE: 331 acggctaaa                                                                  9

<210> SEQ ID NO 332
<211> LENGTH: 9
<212> TYPE: DNA
<213> ORGANISM: Artificial Sequence
<220> FEATURE:
<223> OTHER INFORMATION: Barcoding sequence

<400> SEQUENCE: 332 ctggctaaa                                                                  9

<210> SEQ ID NO 333
<211> LENGTH: 9
<212> TYPE: DNA
<213> ORGANISM: Artificial Sequence
<220> FEATURE:
<223> OTHER INFORMATION: Barcoding sequence
```

-continued

```
<400> SEQUENCE: 333 cacgctaaa                                                              9

<210> SEQ ID NO 334
<211> LENGTH: 9
<212> TYPE: DNA
<213> ORGANISM: Artificial Sequence
<220> FEATURE:
<223> OTHER INFORMATION: Barcoding sequence

<400> SEQUENCE: 334 tgcgctaaa                                                              9

<210> SEQ ID NO 335
<211> LENGTH: 9
<212> TYPE: DNA
<213> ORGANISM: Artificial Sequence
<220> FEATURE:
<223> OTHER INFORMATION: Barcoding sequence

<400> SEQUENCE: 335 gtcgctaaa                                                              9

<210> SEQ ID NO 336
<211> LENGTH: 9
<212> TYPE: DNA
<213> ORGANISM: Artificial Sequence
<220> FEATURE:
<223> OTHER INFORMATION: Barcoding sequence

<400> SEQUENCE: 336 ggtgctaaa                                                              9

<210> SEQ ID NO 337
<211> LENGTH: 9
<212> TYPE: DNA
<213> ORGANISM: Artificial Sequence
<220> FEATURE:
<223> OTHER INFORMATION: Barcoding sequence

<400> SEQUENCE: 337 cctgctaaa                                                              9

<210> SEQ ID NO 338
<211> LENGTH: 9
<212> TYPE: DNA
<213> ORGANISM: Artificial Sequence
<220> FEATURE:
<223> OTHER INFORMATION: Barcoding sequence

<400> SEQUENCE: 338 ggacctaaa                                                              9

<210> SEQ ID NO 339
<211> LENGTH: 9
<212> TYPE: DNA
<213> ORGANISM: Artificial Sequence
<220> FEATURE:
<223> OTHER INFORMATION: Barcoding sequence

<400> SEQUENCE: 339 ccacctaaa                                                              9

<210> SEQ ID NO 340
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 340 cagcctaaa                                                                 9

<210> SEQ ID NO 341
<211> LENGTH: 9
<212> TYPE: DNA
<213> ORGANISM: Artificial Sequence
<220> FEATURE:
<223> OTHER INFORMATION: Barcoding sequence

<400> SEQUENCE: 341 tggcctaaa                                                                 9

<210> SEQ ID NO 342
<211> LENGTH: 9
<212> TYPE: DNA
<213> ORGANISM: Artificial Sequence
<220> FEATURE:
<223> OTHER INFORMATION: Barcoding sequence

<400> SEQUENCE: 342 gtgcctaaa                                                                 9

<210> SEQ ID NO 343
<211> LENGTH: 9
<212> TYPE: DNA
<213> ORGANISM: Artificial Sequence
<220> FEATURE:
<223> OTHER INFORMATION: Barcoding sequence

<400> SEQUENCE: 343 cgtcctaaa                                                                 9

<210> SEQ ID NO 344
<211> LENGTH: 9
<212> TYPE: DNA
<213> ORGANISM: Artificial Sequence
<220> FEATURE:
<223> OTHER INFORMATION: Barcoding sequence

<400> SEQUENCE: 344 gctcctaaa                                                                 9

<210> SEQ ID NO 345
<211> LENGTH: 9
<212> TYPE: DNA
<213> ORGANISM: Artificial Sequence
<220> FEATURE:
<223> OTHER INFORMATION: Barcoding sequence

<400> SEQUENCE: 345 cggtctaaa                                                                 9

<210> SEQ ID NO 346
<211> LENGTH: 9
<212> TYPE: DNA
<213> ORGANISM: Artificial Sequence
<220> FEATURE:
<223> OTHER INFORMATION: Barcoding sequence

<400> SEQUENCE: 346
```

```
gcgtctaaa                                                           9

<210> SEQ ID NO 347
<211> LENGTH: 9
<212> TYPE: DNA
<213> ORGANISM: Artificial Sequence
<220> FEATURE:
<223> OTHER INFORMATION: Barcoding sequence

<400> SEQUENCE: 347 ggctctaaa                                                           9

<210> SEQ ID NO 348
<211> LENGTH: 9
<212> TYPE: DNA
<213> ORGANISM: Artificial Sequence
<220> FEATURE:
<223> OTHER INFORMATION: Barcoding sequence

<400> SEQUENCE: 348 ccggttaaa                                                           9

<210> SEQ ID NO 349
<211> LENGTH: 9
<212> TYPE: DNA
<213> ORGANISM: Artificial Sequence
<220> FEATURE:
<223> OTHER INFORMATION: Barcoding sequence

<400> SEQUENCE: 349 cgcgttaaa                                                           9

<210> SEQ ID NO 350
<211> LENGTH: 9
<212> TYPE: DNA
<213> ORGANISM: Artificial Sequence
<220> FEATURE:
<223> OTHER INFORMATION: Barcoding sequence

<400> SEQUENCE: 350 gccgttaaa                                                           9

<210> SEQ ID NO 351
<211> LENGTH: 9
<212> TYPE: DNA
<213> ORGANISM: Artificial Sequence
<220> FEATURE:
<223> OTHER INFORMATION: Barcoding sequence

<400> SEQUENCE: 351 gcgcttaaa                                                           9

<210> SEQ ID NO 352
<211> LENGTH: 9
<212> TYPE: DNA
<213> ORGANISM: Artificial Sequence
<220> FEATURE:
<223> OTHER INFORMATION: Barcoding sequence

<400> SEQUENCE: 352 ggccttaaa                                                           9

<210> SEQ ID NO 353
<211> LENGTH: 9
<212> TYPE: DNA
```

```
<213> ORGANISM: Artificial Sequence
<220> FEATURE:
<223> OTHER INFORMATION: Barcoding sequence

<400> SEQUENCE: 353 ggagaagaa                                                                 9

<210> SEQ ID NO 354
<211> LENGTH: 9
<212> TYPE: DNA
<213> ORGANISM: Artificial Sequence
<220> FEATURE:
<223> OTHER INFORMATION: Barcoding sequence

<400> SEQUENCE: 354 ccagaagaa                                                                 9

<210> SEQ ID NO 355
<211> LENGTH: 9
<212> TYPE: DNA
<213> ORGANISM: Artificial Sequence
<220> FEATURE:
<223> OTHER INFORMATION: Barcoding sequence

<400> SEQUENCE: 355 gaggaagaa                                                                 9

<210> SEQ ID NO 356
<211> LENGTH: 9
<212> TYPE: DNA
<213> ORGANISM: Artificial Sequence
<220> FEATURE:
<223> OTHER INFORMATION: Barcoding sequence

<400> SEQUENCE: 356 acggaagaa                                                                 9

<210> SEQ ID NO 357
<211> LENGTH: 9
<212> TYPE: DNA
<213> ORGANISM: Artificial Sequence
<220> FEATURE:
<223> OTHER INFORMATION: Barcoding sequence

<400> SEQUENCE: 357 ctggaagaa                                                                 9

<210> SEQ ID NO 358
<211> LENGTH: 9
<212> TYPE: DNA
<213> ORGANISM: Artificial Sequence
<220> FEATURE:
<223> OTHER INFORMATION: Barcoding sequence

<400> SEQUENCE: 358 cacgaagaa                                                                 9

<210> SEQ ID NO 359
<211> LENGTH: 9
<212> TYPE: DNA
<213> ORGANISM: Artificial Sequence
<220> FEATURE:
<223> OTHER INFORMATION: Barcoding sequence

<400> SEQUENCE: 359 agcgaagaa                                                                 9
```

<210> SEQ ID NO 360
<211> LENGTH: 9
<212> TYPE: DNA
<213> ORGANISM: Artificial Sequence
<220> FEATURE:
<223> OTHER INFORMATION: Barcoding sequence

<400> SEQUENCE: 360 tccgaagaa                                                                 9

<210> SEQ ID NO 361
<211> LENGTH: 9
<212> TYPE: DNA
<213> ORGANISM: Artificial Sequence
<220> FEATURE:
<223> OTHER INFORMATION: Barcoding sequence

<400> SEQUENCE: 361 gtcgaagaa                                                                 9

<210> SEQ ID NO 362
<211> LENGTH: 9
<212> TYPE: DNA
<213> ORGANISM: Artificial Sequence
<220> FEATURE:
<223> OTHER INFORMATION: Barcoding sequence

<400> SEQUENCE: 362 cgtgaagaa                                                                 9

<210> SEQ ID NO 363
<211> LENGTH: 9
<212> TYPE: DNA
<213> ORGANISM: Artificial Sequence
<220> FEATURE:
<223> OTHER INFORMATION: Barcoding sequence

<400> SEQUENCE: 363 gctgaagaa                                                                 9

<210> SEQ ID NO 364
<211> LENGTH: 9
<212> TYPE: DNA
<213> ORGANISM: Artificial Sequence
<220> FEATURE:
<223> OTHER INFORMATION: Barcoding sequence

<400> SEQUENCE: 364 cgacaagaa                                                                 9

<210> SEQ ID NO 365
<211> LENGTH: 9
<212> TYPE: DNA
<213> ORGANISM: Artificial Sequence
<220> FEATURE:
<223> OTHER INFORMATION: Barcoding sequence

<400> SEQUENCE: 365 gcacaagaa                                                                 9

<210> SEQ ID NO 366
<211> LENGTH: 9
<212> TYPE: DNA
<213> ORGANISM: Artificial Sequence
<220> FEATURE:

```
<223> OTHER INFORMATION: Barcoding sequence

<400> SEQUENCE: 366 cagcaagaa                                                                   9

<210> SEQ ID NO 367
<211> LENGTH: 9
<212> TYPE: DNA
<213> ORGANISM: Artificial Sequence
<220> FEATURE:
<223> OTHER INFORMATION: Barcoding sequence

<400> SEQUENCE: 367 aggcaagaa                                                                   9

<210> SEQ ID NO 368
<211> LENGTH: 9
<212> TYPE: DNA
<213> ORGANISM: Artificial Sequence
<220> FEATURE:
<223> OTHER INFORMATION: Barcoding sequence

<400> SEQUENCE: 368 tcgcaagaa                                                                   9

<210> SEQ ID NO 369
<211> LENGTH: 9
<212> TYPE: DNA
<213> ORGANISM: Artificial Sequence
<220> FEATURE:
<223> OTHER INFORMATION: Barcoding sequence

<400> SEQUENCE: 369 gtgcaagaa                                                                   9

<210> SEQ ID NO 370
<211> LENGTH: 9
<212> TYPE: DNA
<213> ORGANISM: Artificial Sequence
<220> FEATURE:
<223> OTHER INFORMATION: Barcoding sequence

<400> SEQUENCE: 370 gaccaagaa                                                                   9

<210> SEQ ID NO 371
<211> LENGTH: 9
<212> TYPE: DNA
<213> ORGANISM: Artificial Sequence
<220> FEATURE:
<223> OTHER INFORMATION: Barcoding sequence

<400> SEQUENCE: 371 tgccaagaa                                                                   9

<210> SEQ ID NO 372
<211> LENGTH: 9
<212> TYPE: DNA
<213> ORGANISM: Artificial Sequence
<220> FEATURE:
<223> OTHER INFORMATION: Barcoding sequence

<400> SEQUENCE: 372 ctccaagaa                                                                   9
```

```
<210> SEQ ID NO 373
<211> LENGTH: 9
<212> TYPE: DNA
<213> ORGANISM: Artificial Sequence
<220> FEATURE:
<223> OTHER INFORMATION: Barcoding sequence

<400> SEQUENCE: 373 ggtcaagaa                                                                 9

<210> SEQ ID NO 374
<211> LENGTH: 9
<212> TYPE: DNA
<213> ORGANISM: Artificial Sequence
<220> FEATURE:
<223> OTHER INFORMATION: Barcoding sequence

<400> SEQUENCE: 374 cctcaagaa                                                                 9

<210> SEQ ID NO 375
<211> LENGTH: 9
<212> TYPE: DNA
<213> ORGANISM: Artificial Sequence
<220> FEATURE:
<223> OTHER INFORMATION: Barcoding sequence

<400> SEQUENCE: 375 cggtaagaa                                                                 9

<210> SEQ ID NO 376
<211> LENGTH: 9
<212> TYPE: DNA
<213> ORGANISM: Artificial Sequence
<220> FEATURE:
<223> OTHER INFORMATION: Barcoding sequence

<400> SEQUENCE: 376 gcgtaagaa                                                                 9

<210> SEQ ID NO 377
<211> LENGTH: 9
<212> TYPE: DNA
<213> ORGANISM: Artificial Sequence
<220> FEATURE:
<223> OTHER INFORMATION: Barcoding sequence

<400> SEQUENCE: 377 ggctaagaa                                                                 9

<210> SEQ ID NO 378
<211> LENGTH: 9
<212> TYPE: DNA
<213> ORGANISM: Artificial Sequence
<220> FEATURE:
<223> OTHER INFORMATION: Barcoding sequence

<400> SEQUENCE: 378 ggaagagaa                                                                 9

<210> SEQ ID NO 379
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 379 ccaagagaa                                                                  9

<210> SEQ ID NO 380
<211> LENGTH: 9
<212> TYPE: DNA
<213> ORGANISM: Artificial Sequence
<220> FEATURE:
<223> OTHER INFORMATION: Barcoding sequence

<400> SEQUENCE: 380 gagagagaa                                                                  9

<210> SEQ ID NO 381
<211> LENGTH: 9
<212> TYPE: DNA
<213> ORGANISM: Artificial Sequence
<220> FEATURE:
<223> OTHER INFORMATION: Barcoding sequence

<400> SEQUENCE: 381 aggagagaa                                                                  9

<210> SEQ ID NO 382
<211> LENGTH: 9
<212> TYPE: DNA
<213> ORGANISM: Artificial Sequence
<220> FEATURE:
<223> OTHER INFORMATION: Barcoding sequence

<400> SEQUENCE: 382 tcgagagaa                                                                  9

<210> SEQ ID NO 383
<211> LENGTH: 9
<212> TYPE: DNA
<213> ORGANISM: Artificial Sequence
<220> FEATURE:
<223> OTHER INFORMATION: Barcoding sequence

<400> SEQUENCE: 383 ctgagagaa                                                                  9

<210> SEQ ID NO 384
<211> LENGTH: 9
<212> TYPE: DNA
<213> ORGANISM: Artificial Sequence
<220> FEATURE:
<223> OTHER INFORMATION: Barcoding sequence

<400> SEQUENCE: 384 cacagagaa                                                                  9

<210> SEQ ID NO 385
<211> LENGTH: 9
<212> TYPE: DNA
<213> ORGANISM: Artificial Sequence
<220> FEATURE:
<223> OTHER INFORMATION: Barcoding sequence

<400> SEQUENCE: 385 tgcagagaa                                                                  9

<210> SEQ ID NO 386
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 386 accagagaa                                                                 9

<210> SEQ ID NO 387
<211> LENGTH: 9
<212> TYPE: DNA
<213> ORGANISM: Artificial Sequence
<220> FEATURE:
<223> OTHER INFORMATION: Barcoding sequence

<400> SEQUENCE: 387 gtcagagaa                                                                 9

<210> SEQ ID NO 388
<211> LENGTH: 9
<212> TYPE: DNA
<213> ORGANISM: Artificial Sequence
<220> FEATURE:
<223> OTHER INFORMATION: Barcoding sequence

<400> SEQUENCE: 388 cgtagagaa                                                                 9

<210> SEQ ID NO 389
<211> LENGTH: 9
<212> TYPE: DNA
<213> ORGANISM: Artificial Sequence
<220> FEATURE:
<223> OTHER INFORMATION: Barcoding sequence

<400> SEQUENCE: 389 gctagagaa                                                                 9

<210> SEQ ID NO 390
<211> LENGTH: 9
<212> TYPE: DNA
<213> ORGANISM: Artificial Sequence
<220> FEATURE:
<223> OTHER INFORMATION: Barcoding sequence

<400> SEQUENCE: 390 gaaggagaa                                                                 9

<210> SEQ ID NO 391
<211> LENGTH: 9
<212> TYPE: DNA
<213> ORGANISM: Artificial Sequence
<220> FEATURE:
<223> OTHER INFORMATION: Barcoding sequence

<400> SEQUENCE: 391 agaggagaa                                                                 9

<210> SEQ ID NO 392
<211> LENGTH: 9
<212> TYPE: DNA
<213> ORGANISM: Artificial Sequence
<220> FEATURE:
<223> OTHER INFORMATION: Barcoding sequence

<400> SEQUENCE: 392
``` tcaggagaa					9

<210> SEQ ID NO 393
<211> LENGTH: 9
<212> TYPE: DNA
<213> ORGANISM: Artificial Sequence
<220> FEATURE:
<223> OTHER INFORMATION: Barcoding sequence

<400> SEQUENCE: 393 ctaggagaa					9

<210> SEQ ID NO 394
<211> LENGTH: 9
<212> TYPE: DNA
<213> ORGANISM: Artificial Sequence
<220> FEATURE:
<223> OTHER INFORMATION: Barcoding sequence

<400> SEQUENCE: 394 aacggagaa					9

<210> SEQ ID NO 395
<211> LENGTH: 9
<212> TYPE: DNA
<213> ORGANISM: Artificial Sequence
<220> FEATURE:
<223> OTHER INFORMATION: Barcoding sequence

<400> SEQUENCE: 395 ttcggagaa					9

<210> SEQ ID NO 396
<211> LENGTH: 9
<212> TYPE: DNA
<213> ORGANISM: Artificial Sequence
<220> FEATURE:
<223> OTHER INFORMATION: Barcoding sequence

<400> SEQUENCE: 396 catggagaa					9

<210> SEQ ID NO 397
<211> LENGTH: 9
<212> TYPE: DNA
<213> ORGANISM: Artificial Sequence
<220> FEATURE:
<223> OTHER INFORMATION: Barcoding sequence

<400> SEQUENCE: 397 tgtggagaa					9

<210> SEQ ID NO 398
<211> LENGTH: 9
<212> TYPE: DNA
<213> ORGANISM: Artificial Sequence
<220> FEATURE:
<223> OTHER INFORMATION: Barcoding sequence

<400> SEQUENCE: 398 actggagaa					9

<210> SEQ ID NO 399
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 399 gttggagaa                                                                        9

<210> SEQ ID NO 400
<211> LENGTH: 9
<212> TYPE: DNA
<213> ORGANISM: Artificial Sequence
<220> FEATURE:
<223> OTHER INFORMATION: Barcoding sequence

<400> SEQUENCE: 400 caacgagaa                                                                        9

<210> SEQ ID NO 401
<211> LENGTH: 9
<212> TYPE: DNA
<213> ORGANISM: Artificial Sequence
<220> FEATURE:
<223> OTHER INFORMATION: Barcoding sequence

<400> SEQUENCE: 401 tgacgagaa                                                                        9

<210> SEQ ID NO 402
<211> LENGTH: 9
<212> TYPE: DNA
<213> ORGANISM: Artificial Sequence
<220> FEATURE:
<223> OTHER INFORMATION: Barcoding sequence

<400> SEQUENCE: 402 acacgagaa                                                                        9

<210> SEQ ID NO 403
<211> LENGTH: 9
<212> TYPE: DNA
<213> ORGANISM: Artificial Sequence
<220> FEATURE:
<223> OTHER INFORMATION: Barcoding sequence

<400> SEQUENCE: 403 gtacgagaa                                                                        9

<210> SEQ ID NO 404
<211> LENGTH: 9
<212> TYPE: DNA
<213> ORGANISM: Artificial Sequence
<220> FEATURE:
<223> OTHER INFORMATION: Barcoding sequence

<400> SEQUENCE: 404 aagcgagaa                                                                        9

<210> SEQ ID NO 405
<211> LENGTH: 9
<212> TYPE: DNA
<213> ORGANISM: Artificial Sequence
<220> FEATURE:
<223> OTHER INFORMATION: Barcoding sequence

<400> SEQUENCE: 405 ttgcgagaa                                                                        9
```

```
<210> SEQ ID NO 406
<211> LENGTH: 9
<212> TYPE: DNA
<213> ORGANISM: Artificial Sequence
<220> FEATURE:
<223> OTHER INFORMATION: Barcoding sequence

<400> SEQUENCE: 406 taccgagaa                                                                9

<210> SEQ ID NO 407
<211> LENGTH: 9
<212> TYPE: DNA
<213> ORGANISM: Artificial Sequence
<220> FEATURE:
<223> OTHER INFORMATION: Barcoding sequence

<400> SEQUENCE: 407 atccgagaa                                                                9

<210> SEQ ID NO 408
<211> LENGTH: 9
<212> TYPE: DNA
<213> ORGANISM: Artificial Sequence
<220> FEATURE:
<223> OTHER INFORMATION: Barcoding sequence

<400> SEQUENCE: 408 gatcgagaa                                                                9

<210> SEQ ID NO 409
<211> LENGTH: 9
<212> TYPE: DNA
<213> ORGANISM: Artificial Sequence
<220> FEATURE:
<223> OTHER INFORMATION: Barcoding sequence

<400> SEQUENCE: 409 agtcgagaa                                                                9

<210> SEQ ID NO 410
<211> LENGTH: 9
<212> TYPE: DNA
<213> ORGANISM: Artificial Sequence
<220> FEATURE:
<223> OTHER INFORMATION: Barcoding sequence

<400> SEQUENCE: 410 cttcgagaa                                                                9

<210> SEQ ID NO 411
<211> LENGTH: 9
<212> TYPE: DNA
<213> ORGANISM: Artificial Sequence
<220> FEATURE:
<223> OTHER INFORMATION: Barcoding sequence

<400> SEQUENCE: 411 cgatgagaa                                                                9

<210> SEQ ID NO 412
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 412 gcatgagaa                                                              9

<210> SEQ ID NO 413
<211> LENGTH: 9
<212> TYPE: DNA
<213> ORGANISM: Artificial Sequence
<220> FEATURE:
<223> OTHER INFORMATION: Barcoding sequence

<400> SEQUENCE: 413 cagtgagaa                                                              9

<210> SEQ ID NO 414
<211> LENGTH: 9
<212> TYPE: DNA
<213> ORGANISM: Artificial Sequence
<220> FEATURE:
<223> OTHER INFORMATION: Barcoding sequence

<400> SEQUENCE: 414 tggtgagaa                                                              9

<210> SEQ ID NO 415
<211> LENGTH: 9
<212> TYPE: DNA
<213> ORGANISM: Artificial Sequence
<220> FEATURE:
<223> OTHER INFORMATION: Barcoding sequence

<400> SEQUENCE: 415 acgtgagaa                                                              9

<210> SEQ ID NO 416
<211> LENGTH: 9
<212> TYPE: DNA
<213> ORGANISM: Artificial Sequence
<220> FEATURE:
<223> OTHER INFORMATION: Barcoding sequence

<400> SEQUENCE: 416 gtgtgagaa                                                              9

<210> SEQ ID NO 417
<211> LENGTH: 9
<212> TYPE: DNA
<213> ORGANISM: Artificial Sequence
<220> FEATURE:
<223> OTHER INFORMATION: Barcoding sequence

<400> SEQUENCE: 417 gactgagaa                                                              9

<210> SEQ ID NO 418
<211> LENGTH: 9
<212> TYPE: DNA
<213> ORGANISM: Artificial Sequence
<220> FEATURE:
<223> OTHER INFORMATION: Barcoding sequence

<400> SEQUENCE: 418 agctgagaa                                                              9

<210> SEQ ID NO 419
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 419 tcctgagaa                                                                  9

<210> SEQ ID NO 420
<211> LENGTH: 9
<212> TYPE: DNA
<213> ORGANISM: Artificial Sequence
<220> FEATURE:
<223> OTHER INFORMATION: Barcoding sequence

<400> SEQUENCE: 420 ctctgagaa                                                                  9

<210> SEQ ID NO 421
<211> LENGTH: 9
<212> TYPE: DNA
<213> ORGANISM: Artificial Sequence
<220> FEATURE:
<223> OTHER INFORMATION: Barcoding sequence

<400> SEQUENCE: 421 ggttgagaa                                                                  9

<210> SEQ ID NO 422
<211> LENGTH: 9
<212> TYPE: DNA
<213> ORGANISM: Artificial Sequence
<220> FEATURE:
<223> OTHER INFORMATION: Barcoding sequence

<400> SEQUENCE: 422 ccttgagaa                                                                  9

<210> SEQ ID NO 423
<211> LENGTH: 9
<212> TYPE: DNA
<213> ORGANISM: Artificial Sequence
<220> FEATURE:
<223> OTHER INFORMATION: Barcoding sequence

<400> SEQUENCE: 423 cgaacagaa                                                                  9

<210> SEQ ID NO 424
<211> LENGTH: 9
<212> TYPE: DNA
<213> ORGANISM: Artificial Sequence
<220> FEATURE:
<223> OTHER INFORMATION: Barcoding sequence

<400> SEQUENCE: 424 gcaacagaa                                                                  9

<210> SEQ ID NO 425
<211> LENGTH: 9
<212> TYPE: DNA
<213> ORGANISM: Artificial Sequence
<220> FEATURE:
<223> OTHER INFORMATION: Barcoding sequence

<400> SEQUENCE: 425
``` cagacagaa                                                                      9

<210> SEQ ID NO 426
<211> LENGTH: 9
<212> TYPE: DNA
<213> ORGANISM: Artificial Sequence
<220> FEATURE:
<223> OTHER INFORMATION: Barcoding sequence

<400> SEQUENCE: 426 tggacagaa                                                                      9

<210> SEQ ID NO 427
<211> LENGTH: 9
<212> TYPE: DNA
<213> ORGANISM: Artificial Sequence
<220> FEATURE:
<223> OTHER INFORMATION: Barcoding sequence

<400> SEQUENCE: 427 acgacagaa                                                                      9

<210> SEQ ID NO 428
<211> LENGTH: 9
<212> TYPE: DNA
<213> ORGANISM: Artificial Sequence
<220> FEATURE:
<223> OTHER INFORMATION: Barcoding sequence

<400> SEQUENCE: 428 gtgacagaa                                                                      9

<210> SEQ ID NO 429
<211> LENGTH: 9
<212> TYPE: DNA
<213> ORGANISM: Artificial Sequence
<220> FEATURE:
<223> OTHER INFORMATION: Barcoding sequence

<400> SEQUENCE: 429 gacacagaa                                                                      9

<210> SEQ ID NO 430
<211> LENGTH: 9
<212> TYPE: DNA
<213> ORGANISM: Artificial Sequence
<220> FEATURE:
<223> OTHER INFORMATION: Barcoding sequence

<400> SEQUENCE: 430 agcacagaa                                                                      9

<210> SEQ ID NO 431
<211> LENGTH: 9
<212> TYPE: DNA
<213> ORGANISM: Artificial Sequence
<220> FEATURE:
<223> OTHER INFORMATION: Barcoding sequence

<400> SEQUENCE: 431 tccacagaa                                                                      9

<210> SEQ ID NO 432
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 432 ctcacagaa                                                                 9

<210> SEQ ID NO 433
<211> LENGTH: 9
<212> TYPE: DNA
<213> ORGANISM: Artificial Sequence
<220> FEATURE:
<223> OTHER INFORMATION: Barcoding sequence

<400> SEQUENCE: 433 ggtacagaa                                                                 9

<210> SEQ ID NO 434
<211> LENGTH: 9
<212> TYPE: DNA
<213> ORGANISM: Artificial Sequence
<220> FEATURE:
<223> OTHER INFORMATION: Barcoding sequence

<400> SEQUENCE: 434 cctacagaa                                                                 9

<210> SEQ ID NO 435
<211> LENGTH: 9
<212> TYPE: DNA
<213> ORGANISM: Artificial Sequence
<220> FEATURE:
<223> OTHER INFORMATION: Barcoding sequence

<400> SEQUENCE: 435 caagcagaa                                                                 9

<210> SEQ ID NO 436
<211> LENGTH: 9
<212> TYPE: DNA
<213> ORGANISM: Artificial Sequence
<220> FEATURE:
<223> OTHER INFORMATION: Barcoding sequence

<400> SEQUENCE: 436 tgagcagaa                                                                 9

<210> SEQ ID NO 437
<211> LENGTH: 9
<212> TYPE: DNA
<213> ORGANISM: Artificial Sequence
<220> FEATURE:
<223> OTHER INFORMATION: Barcoding sequence

<400> SEQUENCE: 437 acagcagaa                                                                 9

<210> SEQ ID NO 438
<211> LENGTH: 9
<212> TYPE: DNA
<213> ORGANISM: Artificial Sequence
<220> FEATURE:
<223> OTHER INFORMATION: Barcoding sequence

<400> SEQUENCE: 438 gtagcagaa                                                                 9
```

<210> SEQ ID NO 439
<211> LENGTH: 9
<212> TYPE: DNA
<213> ORGANISM: Artificial Sequence
<220> FEATURE:
<223> OTHER INFORMATION: Barcoding sequence

<400> SEQUENCE: 439 aaggcagaa                                                                9

<210> SEQ ID NO 440
<211> LENGTH: 9
<212> TYPE: DNA
<213> ORGANISM: Artificial Sequence
<220> FEATURE:
<223> OTHER INFORMATION: Barcoding sequence

<400> SEQUENCE: 440 ttggcagaa                                                                9

<210> SEQ ID NO 441
<211> LENGTH: 9
<212> TYPE: DNA
<213> ORGANISM: Artificial Sequence
<220> FEATURE:
<223> OTHER INFORMATION: Barcoding sequence

<400> SEQUENCE: 441 tacgcagaa                                                                9

<210> SEQ ID NO 442
<211> LENGTH: 9
<212> TYPE: DNA
<213> ORGANISM: Artificial Sequence
<220> FEATURE:
<223> OTHER INFORMATION: Barcoding sequence

<400> SEQUENCE: 442 atcgcagaa                                                                9

<210> SEQ ID NO 443
<211> LENGTH: 9
<212> TYPE: DNA
<213> ORGANISM: Artificial Sequence
<220> FEATURE:
<223> OTHER INFORMATION: Barcoding sequence

<400> SEQUENCE: 443 gatgcagaa                                                                9

<210> SEQ ID NO 444
<211> LENGTH: 9
<212> TYPE: DNA
<213> ORGANISM: Artificial Sequence
<220> FEATURE:
<223> OTHER INFORMATION: Barcoding sequence

<400> SEQUENCE: 444 agtgcagaa                                                                9

<210> SEQ ID NO 445
<211> LENGTH: 9
<212> TYPE: DNA
<213> ORGANISM: Artificial Sequence
<220> FEATURE:

-continued

<223> OTHER INFORMATION: Barcoding sequence

<400> SEQUENCE: 445 cttgcagaa                                                                  9

<210> SEQ ID NO 446
<211> LENGTH: 9
<212> TYPE: DNA
<213> ORGANISM: Artificial Sequence
<220> FEATURE:
<223> OTHER INFORMATION: Barcoding sequence

<400> SEQUENCE: 446 gaaccagaa                                                                  9

<210> SEQ ID NO 447
<211> LENGTH: 9
<212> TYPE: DNA
<213> ORGANISM: Artificial Sequence
<220> FEATURE:
<223> OTHER INFORMATION: Barcoding sequence

<400> SEQUENCE: 447 agaccagaa                                                                  9

<210> SEQ ID NO 448
<211> LENGTH: 9
<212> TYPE: DNA
<213> ORGANISM: Artificial Sequence
<220> FEATURE:
<223> OTHER INFORMATION: Barcoding sequence

<400> SEQUENCE: 448 tcaccagaa                                                                  9

<210> SEQ ID NO 449
<211> LENGTH: 9
<212> TYPE: DNA
<213> ORGANISM: Artificial Sequence
<220> FEATURE:
<223> OTHER INFORMATION: Barcoding sequence

<400> SEQUENCE: 449 ctaccagaa                                                                  9

<210> SEQ ID NO 450
<211> LENGTH: 9
<212> TYPE: DNA
<213> ORGANISM: Artificial Sequence
<220> FEATURE:
<223> OTHER INFORMATION: Barcoding sequence

<400> SEQUENCE: 450 tagccagaa                                                                  9

<210> SEQ ID NO 451
<211> LENGTH: 9
<212> TYPE: DNA
<213> ORGANISM: Artificial Sequence
<220> FEATURE:
<223> OTHER INFORMATION: Barcoding sequence

<400> SEQUENCE: 451 atgccagaa                                                                  9

```
<210> SEQ ID NO 452
<211> LENGTH: 9
<212> TYPE: DNA
<213> ORGANISM: Artificial Sequence
<220> FEATURE:
<223> OTHER INFORMATION: Barcoding sequence

<400> SEQUENCE: 452 catccagaa                                                                 9

<210> SEQ ID NO 453
<211> LENGTH: 9
<212> TYPE: DNA
<213> ORGANISM: Artificial Sequence
<220> FEATURE:
<223> OTHER INFORMATION: Barcoding sequence

<400> SEQUENCE: 453 tgtccagaa                                                                 9

<210> SEQ ID NO 454
<211> LENGTH: 9
<212> TYPE: DNA
<213> ORGANISM: Artificial Sequence
<220> FEATURE:
<223> OTHER INFORMATION: Barcoding sequence

<400> SEQUENCE: 454 actccagaa                                                                 9

<210> SEQ ID NO 455
<211> LENGTH: 9
<212> TYPE: DNA
<213> ORGANISM: Artificial Sequence
<220> FEATURE:
<223> OTHER INFORMATION: Barcoding sequence

<400> SEQUENCE: 455 gttccagaa                                                                 9

<210> SEQ ID NO 456
<211> LENGTH: 9
<212> TYPE: DNA
<213> ORGANISM: Artificial Sequence
<220> FEATURE:
<223> OTHER INFORMATION: Barcoding sequence

<400> SEQUENCE: 456 ggatcagaa                                                                 9

<210> SEQ ID NO 457
<211> LENGTH: 9
<212> TYPE: DNA
<213> ORGANISM: Artificial Sequence
<220> FEATURE:
<223> OTHER INFORMATION: Barcoding sequence

<400> SEQUENCE: 457 ccatcagaa                                                                 9

<210> SEQ ID NO 458
<211> LENGTH: 9
<212> TYPE: DNA
<213> ORGANISM: Artificial Sequence
<220> FEATURE:
<223> OTHER INFORMATION: Barcoding sequence
```

<400> SEQUENCE: 458 gagtcagaa                                                                9

<210> SEQ ID NO 459
<211> LENGTH: 9
<212> TYPE: DNA
<213> ORGANISM: Artificial Sequence
<220> FEATURE:
<223> OTHER INFORMATION: Barcoding sequence

<400> SEQUENCE: 459 aggtcagaa                                                                9

<210> SEQ ID NO 460
<211> LENGTH: 9
<212> TYPE: DNA
<213> ORGANISM: Artificial Sequence
<220> FEATURE:
<223> OTHER INFORMATION: Barcoding sequence

<400> SEQUENCE: 460 tcgtcagaa                                                                9

<210> SEQ ID NO 461
<211> LENGTH: 9
<212> TYPE: DNA
<213> ORGANISM: Artificial Sequence
<220> FEATURE:
<223> OTHER INFORMATION: Barcoding sequence

<400> SEQUENCE: 461 ctgtcagaa                                                                9

<210> SEQ ID NO 462
<211> LENGTH: 9
<212> TYPE: DNA
<213> ORGANISM: Artificial Sequence
<220> FEATURE:
<223> OTHER INFORMATION: Barcoding sequence

<400> SEQUENCE: 462 cactcagaa                                                                9

<210> SEQ ID NO 463
<211> LENGTH: 9
<212> TYPE: DNA
<213> ORGANISM: Artificial Sequence
<220> FEATURE:
<223> OTHER INFORMATION: Barcoding sequence

<400> SEQUENCE: 463 tgctcagaa                                                                9

<210> SEQ ID NO 464
<211> LENGTH: 9
<212> TYPE: DNA
<213> ORGANISM: Artificial Sequence
<220> FEATURE:
<223> OTHER INFORMATION: Barcoding sequence

<400> SEQUENCE: 464 acctcagaa                                                                9

<210> SEQ ID NO 465
<211> LENGTH: 9

```
<212> TYPE: DNA
<213> ORGANISM: Artificial Sequence
<220> FEATURE:
<223> OTHER INFORMATION: Barcoding sequence

<400> SEQUENCE: 465 gtctcagaa                                                                9

<210> SEQ ID NO 466
<211> LENGTH: 9
<212> TYPE: DNA
<213> ORGANISM: Artificial Sequence
<220> FEATURE:
<223> OTHER INFORMATION: Barcoding sequence

<400> SEQUENCE: 466 cgttcagaa                                                                9

<210> SEQ ID NO 467
<211> LENGTH: 9
<212> TYPE: DNA
<213> ORGANISM: Artificial Sequence
<220> FEATURE:
<223> OTHER INFORMATION: Barcoding sequence

<400> SEQUENCE: 467 gcttcagaa                                                                9

<210> SEQ ID NO 468
<211> LENGTH: 9
<212> TYPE: DNA
<213> ORGANISM: Artificial Sequence
<220> FEATURE:
<223> OTHER INFORMATION: Barcoding sequence

<400> SEQUENCE: 468 cggatagaa                                                                9

<210> SEQ ID NO 469
<211> LENGTH: 9
<212> TYPE: DNA
<213> ORGANISM: Artificial Sequence
<220> FEATURE:
<223> OTHER INFORMATION: Barcoding sequence

<400> SEQUENCE: 469 gcgatagaa                                                                9

<210> SEQ ID NO 470
<211> LENGTH: 9
<212> TYPE: DNA
<213> ORGANISM: Artificial Sequence
<220> FEATURE:
<223> OTHER INFORMATION: Barcoding sequence

<400> SEQUENCE: 470 ggcatagaa                                                                9

<210> SEQ ID NO 471
<211> LENGTH: 9
<212> TYPE: DNA
<213> ORGANISM: Artificial Sequence
<220> FEATURE:
<223> OTHER INFORMATION: Barcoding sequence

<400> SEQUENCE: 471
``` cgagtagaa 9

<210> SEQ ID NO 472
<211> LENGTH: 9
<212> TYPE: DNA
<213> ORGANISM: Artificial Sequence
<220> FEATURE:
<223> OTHER INFORMATION: Barcoding sequence

<400> SEQUENCE: 472 gcagtagaa 9

<210> SEQ ID NO 473
<211> LENGTH: 9
<212> TYPE: DNA
<213> ORGANISM: Artificial Sequence
<220> FEATURE:
<223> OTHER INFORMATION: Barcoding sequence

<400> SEQUENCE: 473 caggtagaa 9

<210> SEQ ID NO 474
<211> LENGTH: 9
<212> TYPE: DNA
<213> ORGANISM: Artificial Sequence
<220> FEATURE:
<223> OTHER INFORMATION: Barcoding sequence

<400> SEQUENCE: 474 tcggtagaa 9

<210> SEQ ID NO 475
<211> LENGTH: 9
<212> TYPE: DNA
<213> ORGANISM: Artificial Sequence
<220> FEATURE:
<223> OTHER INFORMATION: Barcoding sequence

<400> SEQUENCE: 475 gtggtagaa 9

<210> SEQ ID NO 476
<211> LENGTH: 9
<212> TYPE: DNA
<213> ORGANISM: Artificial Sequence
<220> FEATURE:
<223> OTHER INFORMATION: Barcoding sequence

<400> SEQUENCE: 476 gacgtagaa 9

<210> SEQ ID NO 477
<211> LENGTH: 9
<212> TYPE: DNA
<213> ORGANISM: Artificial Sequence
<220> FEATURE:
<223> OTHER INFORMATION: Barcoding sequence

<400> SEQUENCE: 477 tgcgtagaa 9

<210> SEQ ID NO 478
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 478 accgtagaa                                                                  9

<210> SEQ ID NO 479
<211> LENGTH: 9
<212> TYPE: DNA
<213> ORGANISM: Artificial Sequence
<220> FEATURE:
<223> OTHER INFORMATION: Barcoding sequence

<400> SEQUENCE: 479 ctcgtagaa                                                                  9

<210> SEQ ID NO 480
<211> LENGTH: 9
<212> TYPE: DNA
<213> ORGANISM: Artificial Sequence
<220> FEATURE:
<223> OTHER INFORMATION: Barcoding sequence

<400> SEQUENCE: 480 ggtgtagaa                                                                  9

<210> SEQ ID NO 481
<211> LENGTH: 9
<212> TYPE: DNA
<213> ORGANISM: Artificial Sequence
<220> FEATURE:
<223> OTHER INFORMATION: Barcoding sequence

<400> SEQUENCE: 481 cctgtagaa                                                                  9

<210> SEQ ID NO 482
<211> LENGTH: 9
<212> TYPE: DNA
<213> ORGANISM: Artificial Sequence
<220> FEATURE:
<223> OTHER INFORMATION: Barcoding sequence

<400> SEQUENCE: 482 ggactagaa                                                                  9

<210> SEQ ID NO 483
<211> LENGTH: 9
<212> TYPE: DNA
<213> ORGANISM: Artificial Sequence
<220> FEATURE:
<223> OTHER INFORMATION: Barcoding sequence

<400> SEQUENCE: 483 ccactagaa                                                                  9

<210> SEQ ID NO 484
<211> LENGTH: 9
<212> TYPE: DNA
<213> ORGANISM: Artificial Sequence
<220> FEATURE:
<223> OTHER INFORMATION: Barcoding sequence

<400> SEQUENCE: 484 gagctagaa                                                                  9
```

<210> SEQ ID NO 485
<211> LENGTH: 9
<212> TYPE: DNA
<213> ORGANISM: Artificial Sequence
<220> FEATURE:
<223> OTHER INFORMATION: Barcoding sequence

<400> SEQUENCE: 485 tggctagaa                                                                 9

<210> SEQ ID NO 486
<211> LENGTH: 9
<212> TYPE: DNA
<213> ORGANISM: Artificial Sequence
<220> FEATURE:
<223> OTHER INFORMATION: Barcoding sequence

<400> SEQUENCE: 486 acgctagaa                                                                 9

<210> SEQ ID NO 487
<211> LENGTH: 9
<212> TYPE: DNA
<213> ORGANISM: Artificial Sequence
<220> FEATURE:
<223> OTHER INFORMATION: Barcoding sequence

<400> SEQUENCE: 487 ctgctagaa                                                                 9

<210> SEQ ID NO 488
<211> LENGTH: 9
<212> TYPE: DNA
<213> ORGANISM: Artificial Sequence
<220> FEATURE:
<223> OTHER INFORMATION: Barcoding sequence

<400> SEQUENCE: 488 cacctagaa                                                                 9

<210> SEQ ID NO 489
<211> LENGTH: 9
<212> TYPE: DNA
<213> ORGANISM: Artificial Sequence
<220> FEATURE:
<223> OTHER INFORMATION: Barcoding sequence

<400> SEQUENCE: 489 agcctagaa                                                                 9

<210> SEQ ID NO 490
<211> LENGTH: 9
<212> TYPE: DNA
<213> ORGANISM: Artificial Sequence
<220> FEATURE:
<223> OTHER INFORMATION: Barcoding sequence

<400> SEQUENCE: 490 gtcctagaa                                                                 9

<210> SEQ ID NO 491
<211> LENGTH: 9
<212> TYPE: DNA
<213> ORGANISM: Artificial Sequence
<220> FEATURE:
<223> OTHER INFORMATION: Barcoding sequence

```
<400> SEQUENCE: 491 cgtctagaa                                                                9

<210> SEQ ID NO 492
<211> LENGTH: 9
<212> TYPE: DNA
<213> ORGANISM: Artificial Sequence
<220> FEATURE:
<223> OTHER INFORMATION: Barcoding sequence

<400> SEQUENCE: 492 gctctagaa                                                                9

<210> SEQ ID NO 493
<211> LENGTH: 9
<212> TYPE: DNA
<213> ORGANISM: Artificial Sequence
<220> FEATURE:
<223> OTHER INFORMATION: Barcoding sequence

<400> SEQUENCE: 493 ccgttagaa                                                                9

<210> SEQ ID NO 494
<211> LENGTH: 9
<212> TYPE: DNA
<213> ORGANISM: Artificial Sequence
<220> FEATURE:
<223> OTHER INFORMATION: Barcoding sequence

<400> SEQUENCE: 494 cgcttagaa                                                                9

<210> SEQ ID NO 495
<211> LENGTH: 9
<212> TYPE: DNA
<213> ORGANISM: Artificial Sequence
<220> FEATURE:
<223> OTHER INFORMATION: Barcoding sequence

<400> SEQUENCE: 495 gccttagaa                                                                9

<210> SEQ ID NO 496
<211> LENGTH: 9
<212> TYPE: DNA
<213> ORGANISM: Artificial Sequence
<220> FEATURE:
<223> OTHER INFORMATION: Barcoding sequence

<400> SEQUENCE: 496 gagaaggaa                                                                9

<210> SEQ ID NO 497
<211> LENGTH: 9
<212> TYPE: DNA
<213> ORGANISM: Artificial Sequence
<220> FEATURE:
<223> OTHER INFORMATION: Barcoding sequence

<400> SEQUENCE: 497 aggaaggaa                                                                9

<210> SEQ ID NO 498
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 498 tcgaaggaa                                                                 9

<210> SEQ ID NO 499
<211> LENGTH: 9
<212> TYPE: DNA
<213> ORGANISM: Artificial Sequence
<220> FEATURE:
<223> OTHER INFORMATION: Barcoding sequence

<400> SEQUENCE: 499 ctgaaggaa                                                                 9

<210> SEQ ID NO 500
<211> LENGTH: 9
<212> TYPE: DNA
<213> ORGANISM: Artificial Sequence
<220> FEATURE:
<223> OTHER INFORMATION: Barcoding sequence

<400> SEQUENCE: 500 cacaaggaa                                                                 9

<210> SEQ ID NO 501
<211> LENGTH: 9
<212> TYPE: DNA
<213> ORGANISM: Artificial Sequence
<220> FEATURE:
<223> OTHER INFORMATION: Barcoding sequence

<400> SEQUENCE: 501 tgcaaggaa                                                                 9

<210> SEQ ID NO 502
<211> LENGTH: 9
<212> TYPE: DNA
<213> ORGANISM: Artificial Sequence
<220> FEATURE:
<223> OTHER INFORMATION: Barcoding sequence

<400> SEQUENCE: 502 accaaggaa                                                                 9

<210> SEQ ID NO 503
<211> LENGTH: 9
<212> TYPE: DNA
<213> ORGANISM: Artificial Sequence
<220> FEATURE:
<223> OTHER INFORMATION: Barcoding sequence

<400> SEQUENCE: 503 gtcaaggaa                                                                 9

<210> SEQ ID NO 504
<211> LENGTH: 9
<212> TYPE: DNA
<213> ORGANISM: Artificial Sequence
<220> FEATURE:
<223> OTHER INFORMATION: Barcoding sequence

<400> SEQUENCE: 504
```

-continued

```
ggtaaggaa                                                           9

<210> SEQ ID NO 505
<211> LENGTH: 9
<212> TYPE: DNA
<213> ORGANISM: Artificial Sequence
<220> FEATURE:
<223> OTHER INFORMATION: Barcoding sequence

<400> SEQUENCE: 505 cctaaggaa                                                           9

<210> SEQ ID NO 506
<211> LENGTH: 9
<212> TYPE: DNA
<213> ORGANISM: Artificial Sequence
<220> FEATURE:
<223> OTHER INFORMATION: Barcoding sequence

<400> SEQUENCE: 506 gaagaggaa                                                           9

<210> SEQ ID NO 507
<211> LENGTH: 9
<212> TYPE: DNA
<213> ORGANISM: Artificial Sequence
<220> FEATURE:
<223> OTHER INFORMATION: Barcoding sequence

<400> SEQUENCE: 507 agagaggaa                                                           9

<210> SEQ ID NO 508
<211> LENGTH: 9
<212> TYPE: DNA
<213> ORGANISM: Artificial Sequence
<220> FEATURE:
<223> OTHER INFORMATION: Barcoding sequence

<400> SEQUENCE: 508 tcagaggaa                                                           9

<210> SEQ ID NO 509
<211> LENGTH: 9
<212> TYPE: DNA
<213> ORGANISM: Artificial Sequence
<220> FEATURE:
<223> OTHER INFORMATION: Barcoding sequence

<400> SEQUENCE: 509 ctagaggaa                                                           9

<210> SEQ ID NO 510
<211> LENGTH: 9
<212> TYPE: DNA
<213> ORGANISM: Artificial Sequence
<220> FEATURE:
<223> OTHER INFORMATION: Barcoding sequence

<400> SEQUENCE: 510 aaggaggaa                                                           9

<210> SEQ ID NO 511
<211> LENGTH: 9
<212> TYPE: DNA
```

```
<213> ORGANISM: Artificial Sequence
<220> FEATURE:
<223> OTHER INFORMATION: Barcoding sequence

<400> SEQUENCE: 511 ttggaggaa                                                                9

<210> SEQ ID NO 512
<211> LENGTH: 9
<212> TYPE: DNA
<213> ORGANISM: Artificial Sequence
<220> FEATURE:
<223> OTHER INFORMATION: Barcoding sequence

<400> SEQUENCE: 512 tacgaggaa                                                                9

<210> SEQ ID NO 513
<211> LENGTH: 9
<212> TYPE: DNA
<213> ORGANISM: Artificial Sequence
<220> FEATURE:
<223> OTHER INFORMATION: Barcoding sequence

<400> SEQUENCE: 513 atcgaggaa                                                                9

<210> SEQ ID NO 514
<211> LENGTH: 9
<212> TYPE: DNA
<213> ORGANISM: Artificial Sequence
<220> FEATURE:
<223> OTHER INFORMATION: Barcoding sequence

<400> SEQUENCE: 514 catgaggaa                                                                9

<210> SEQ ID NO 515
<211> LENGTH: 9
<212> TYPE: DNA
<213> ORGANISM: Artificial Sequence
<220> FEATURE:
<223> OTHER INFORMATION: Barcoding sequence

<400> SEQUENCE: 515 tgtgaggaa                                                                9

<210> SEQ ID NO 516
<211> LENGTH: 9
<212> TYPE: DNA
<213> ORGANISM: Artificial Sequence
<220> FEATURE:
<223> OTHER INFORMATION: Barcoding sequence

<400> SEQUENCE: 516 actgaggaa                                                                9

<210> SEQ ID NO 517
<211> LENGTH: 9
<212> TYPE: DNA
<213> ORGANISM: Artificial Sequence
<220> FEATURE:
<223> OTHER INFORMATION: Barcoding sequence

<400> SEQUENCE: 517 gttgaggaa                                                                9
```

```
<210> SEQ ID NO 518
<211> LENGTH: 9
<212> TYPE: DNA
<213> ORGANISM: Artificial Sequence
<220> FEATURE:
<223> OTHER INFORMATION: Barcoding sequence

<400> SEQUENCE: 518 caacaggaa                                                                 9

<210> SEQ ID NO 519
<211> LENGTH: 9
<212> TYPE: DNA
<213> ORGANISM: Artificial Sequence
<220> FEATURE:
<223> OTHER INFORMATION: Barcoding sequence

<400> SEQUENCE: 519 tgacaggaa                                                                 9

<210> SEQ ID NO 520
<211> LENGTH: 9
<212> TYPE: DNA
<213> ORGANISM: Artificial Sequence
<220> FEATURE:
<223> OTHER INFORMATION: Barcoding sequence

<400> SEQUENCE: 520 acacaggaa                                                                 9

<210> SEQ ID NO 521
<211> LENGTH: 9
<212> TYPE: DNA
<213> ORGANISM: Artificial Sequence
<220> FEATURE:
<223> OTHER INFORMATION: Barcoding sequence

<400> SEQUENCE: 521 gtacaggaa                                                                 9

<210> SEQ ID NO 522
<211> LENGTH: 9
<212> TYPE: DNA
<213> ORGANISM: Artificial Sequence
<220> FEATURE:
<223> OTHER INFORMATION: Barcoding sequence

<400> SEQUENCE: 522 tagcaggaa                                                                 9

<210> SEQ ID NO 523
<211> LENGTH: 9
<212> TYPE: DNA
<213> ORGANISM: Artificial Sequence
<220> FEATURE:
<223> OTHER INFORMATION: Barcoding sequence

<400> SEQUENCE: 523 atgcaggaa                                                                 9

<210> SEQ ID NO 524
<211> LENGTH: 9
<212> TYPE: DNA
<213> ORGANISM: Artificial Sequence
<220> FEATURE:
```

```
<223> OTHER INFORMATION: Barcoding sequence

<400> SEQUENCE: 524 aaccaggaa                                                                9

<210> SEQ ID NO 525
<211> LENGTH: 9
<212> TYPE: DNA
<213> ORGANISM: Artificial Sequence
<220> FEATURE:
<223> OTHER INFORMATION: Barcoding sequence

<400> SEQUENCE: 525 ttccaggaa                                                                9

<210> SEQ ID NO 526
<211> LENGTH: 9
<212> TYPE: DNA
<213> ORGANISM: Artificial Sequence
<220> FEATURE:
<223> OTHER INFORMATION: Barcoding sequence

<400> SEQUENCE: 526 gatcaggaa                                                                9

<210> SEQ ID NO 527
<211> LENGTH: 9
<212> TYPE: DNA
<213> ORGANISM: Artificial Sequence
<220> FEATURE:
<223> OTHER INFORMATION: Barcoding sequence

<400> SEQUENCE: 527 agtcaggaa                                                                9

<210> SEQ ID NO 528
<211> LENGTH: 9
<212> TYPE: DNA
<213> ORGANISM: Artificial Sequence
<220> FEATURE:
<223> OTHER INFORMATION: Barcoding sequence

<400> SEQUENCE: 528 tctcaggaa                                                                9

<210> SEQ ID NO 529
<211> LENGTH: 9
<212> TYPE: DNA
<213> ORGANISM: Artificial Sequence
<220> FEATURE:
<223> OTHER INFORMATION: Barcoding sequence

<400> SEQUENCE: 529 cttcaggaa                                                                9

<210> SEQ ID NO 530
<211> LENGTH: 9
<212> TYPE: DNA
<213> ORGANISM: Artificial Sequence
<220> FEATURE:
<223> OTHER INFORMATION: Barcoding sequence

<400> SEQUENCE: 530 ggataggaa                                                                9
```

```
<210> SEQ ID NO 531
<211> LENGTH: 9
<212> TYPE: DNA
<213> ORGANISM: Artificial Sequence
<220> FEATURE:
<223> OTHER INFORMATION: Barcoding sequence

<400> SEQUENCE: 531 ccataggaa                                                                  9

<210> SEQ ID NO 532
<211> LENGTH: 9
<212> TYPE: DNA
<213> ORGANISM: Artificial Sequence
<220> FEATURE:
<223> OTHER INFORMATION: Barcoding sequence

<400> SEQUENCE: 532 cagtaggaa                                                                  9

<210> SEQ ID NO 533
<211> LENGTH: 9
<212> TYPE: DNA
<213> ORGANISM: Artificial Sequence
<220> FEATURE:
<223> OTHER INFORMATION: Barcoding sequence

<400> SEQUENCE: 533 tggtaggaa                                                                  9

<210> SEQ ID NO 534
<211> LENGTH: 9
<212> TYPE: DNA
<213> ORGANISM: Artificial Sequence
<220> FEATURE:
<223> OTHER INFORMATION: Barcoding sequence

<400> SEQUENCE: 534 acgtaggaa                                                                  9

<210> SEQ ID NO 535
<211> LENGTH: 9
<212> TYPE: DNA
<213> ORGANISM: Artificial Sequence
<220> FEATURE:
<223> OTHER INFORMATION: Barcoding sequence

<400> SEQUENCE: 535 gtgtaggaa                                                                  9

<210> SEQ ID NO 536
<211> LENGTH: 9
<212> TYPE: DNA
<213> ORGANISM: Artificial Sequence
<220> FEATURE:
<223> OTHER INFORMATION: Barcoding sequence

<400> SEQUENCE: 536 gactaggaa                                                                  9

<210> SEQ ID NO 537
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 537 agctaggaa                                                                   9

<210> SEQ ID NO 538
<211> LENGTH: 9
<212> TYPE: DNA
<213> ORGANISM: Artificial Sequence
<220> FEATURE:
<223> OTHER INFORMATION: Barcoding sequence

<400> SEQUENCE: 538 ctctaggaa                                                                   9

<210> SEQ ID NO 539
<211> LENGTH: 9
<212> TYPE: DNA
<213> ORGANISM: Artificial Sequence
<220> FEATURE:
<223> OTHER INFORMATION: Barcoding sequence

<400> SEQUENCE: 539 cgttaggaa                                                                   9

<210> SEQ ID NO 540
<211> LENGTH: 9
<212> TYPE: DNA
<213> ORGANISM: Artificial Sequence
<220> FEATURE:
<223> OTHER INFORMATION: Barcoding sequence

<400> SEQUENCE: 540 gcttaggaa                                                                   9

<210> SEQ ID NO 541
<211> LENGTH: 9
<212> TYPE: DNA
<213> ORGANISM: Artificial Sequence
<220> FEATURE:
<223> OTHER INFORMATION: Barcoding sequence

<400> SEQUENCE: 541 agaacggaa                                                                   9

<210> SEQ ID NO 542
<211> LENGTH: 9
<212> TYPE: DNA
<213> ORGANISM: Artificial Sequence
<220> FEATURE:
<223> OTHER INFORMATION: Barcoding sequence

<400> SEQUENCE: 542 tcaacggaa                                                                   9

<210> SEQ ID NO 543
<211> LENGTH: 9
<212> TYPE: DNA
<213> ORGANISM: Artificial Sequence
<220> FEATURE:
<223> OTHER INFORMATION: Barcoding sequence

<400> SEQUENCE: 543 gtaacggaa                                                                   9

<210> SEQ ID NO 544
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 544 aagacggaa                                                              9

<210> SEQ ID NO 545
<211> LENGTH: 9
<212> TYPE: DNA
<213> ORGANISM: Artificial Sequence
<220> FEATURE:
<223> OTHER INFORMATION: Barcoding sequence

<400> SEQUENCE: 545 ttgacggaa                                                              9

<210> SEQ ID NO 546
<211> LENGTH: 9
<212> TYPE: DNA
<213> ORGANISM: Artificial Sequence
<220> FEATURE:
<223> OTHER INFORMATION: Barcoding sequence

<400> SEQUENCE: 546 tacacggaa                                                              9

<210> SEQ ID NO 547
<211> LENGTH: 9
<212> TYPE: DNA
<213> ORGANISM: Artificial Sequence
<220> FEATURE:
<223> OTHER INFORMATION: Barcoding sequence

<400> SEQUENCE: 547 atcacggaa                                                              9

<210> SEQ ID NO 548
<211> LENGTH: 9
<212> TYPE: DNA
<213> ORGANISM: Artificial Sequence
<220> FEATURE:
<223> OTHER INFORMATION: Barcoding sequence

<400> SEQUENCE: 548 gatacggaa                                                              9

<210> SEQ ID NO 549
<211> LENGTH: 9
<212> TYPE: DNA
<213> ORGANISM: Artificial Sequence
<220> FEATURE:
<223> OTHER INFORMATION: Barcoding sequence

<400> SEQUENCE: 549 tgtacggaa                                                              9

<210> SEQ ID NO 550
<211> LENGTH: 9
<212> TYPE: DNA
<213> ORGANISM: Artificial Sequence
<220> FEATURE:
<223> OTHER INFORMATION: Barcoding sequence

<400> SEQUENCE: 550
``` actacggaa                                                                        9

<210> SEQ ID NO 551
<211> LENGTH: 9
<212> TYPE: DNA
<213> ORGANISM: Artificial Sequence
<220> FEATURE:
<223> OTHER INFORMATION: Barcoding sequence

<400> SEQUENCE: 551 cttacggaa                                                                        9

<210> SEQ ID NO 552
<211> LENGTH: 9
<212> TYPE: DNA
<213> ORGANISM: Artificial Sequence
<220> FEATURE:
<223> OTHER INFORMATION: Barcoding sequence

<400> SEQUENCE: 552 taagcggaa                                                                        9

<210> SEQ ID NO 553
<211> LENGTH: 9
<212> TYPE: DNA
<213> ORGANISM: Artificial Sequence
<220> FEATURE:
<223> OTHER INFORMATION: Barcoding sequence

<400> SEQUENCE: 553 atagcggaa                                                                        9

<210> SEQ ID NO 554
<211> LENGTH: 9
<212> TYPE: DNA
<213> ORGANISM: Artificial Sequence
<220> FEATURE:
<223> OTHER INFORMATION: Barcoding sequence

<400> SEQUENCE: 554 aatgcggaa                                                                        9

<210> SEQ ID NO 555
<211> LENGTH: 9
<212> TYPE: DNA
<213> ORGANISM: Artificial Sequence
<220> FEATURE:
<223> OTHER INFORMATION: Barcoding sequence

<400> SEQUENCE: 555 ttaccggaa                                                                        9

<210> SEQ ID NO 556
<211> LENGTH: 9
<212> TYPE: DNA
<213> ORGANISM: Artificial Sequence
<220> FEATURE:
<223> OTHER INFORMATION: Barcoding sequence

<400> SEQUENCE: 556 tatccggaa                                                                        9

<210> SEQ ID NO 557
<211> LENGTH: 9
<212> TYPE: DNA
<213> ORGANISM: Artificial Sequence
<220> FEATURE:
<223> OTHER INFORMATION: Barcoding sequence

<400> SEQUENCE: 557 attccggaa                                                                                              9

<210> SEQ ID NO 558
<211> LENGTH: 9
<212> TYPE: DNA
<213> ORGANISM: Artificial Sequence
<220> FEATURE:
<223> OTHER INFORMATION: Barcoding sequence

<400> SEQUENCE: 558 gaatcggaa                                                                                              9

<210> SEQ ID NO 559
<211> LENGTH: 9
<212> TYPE: DNA
<213> ORGANISM: Artificial Sequence
<220> FEATURE:
<223> OTHER INFORMATION: Barcoding sequence

<400> SEQUENCE: 559 tgatcggaa                                                                                              9

<210> SEQ ID NO 560
<211> LENGTH: 9
<212> TYPE: DNA
<213> ORGANISM: Artificial Sequence
<220> FEATURE:
<223> OTHER INFORMATION: Barcoding sequence

<400> SEQUENCE: 560 acatcggaa                                                                                              9

<210> SEQ ID NO 561
<211> LENGTH: 9
<212> TYPE: DNA
<213> ORGANISM: Artificial Sequence
<220> FEATURE:
<223> OTHER INFORMATION: Barcoding sequence

<400> SEQUENCE: 561 ctatcggaa                                                                                              9

<210> SEQ ID NO 562
<211> LENGTH: 9
<212> TYPE: DNA
<213> ORGANISM: Artificial Sequence
<220> FEATURE:
<223> OTHER INFORMATION: Barcoding sequence

<400> SEQUENCE: 562 tagtcggaa                                                                                              9

<210> SEQ ID NO 563
<211> LENGTH: 9
<212> TYPE: DNA
<213> ORGANISM: Artificial Sequence
<220> FEATURE:
<223> OTHER INFORMATION: Barcoding sequence

<400> SEQUENCE: 563 atgtcggaa                                                                                              9

```
<210> SEQ ID NO 564
<211> LENGTH: 9
<212> TYPE: DNA
<213> ORGANISM: Artificial Sequence
<220> FEATURE:
<223> OTHER INFORMATION: Barcoding sequence

<400> SEQUENCE: 564 aactcggaa                                                                 9

<210> SEQ ID NO 565
<211> LENGTH: 9
<212> TYPE: DNA
<213> ORGANISM: Artificial Sequence
<220> FEATURE:
<223> OTHER INFORMATION: Barcoding sequence

<400> SEQUENCE: 565 ttctcggaa                                                                 9

<210> SEQ ID NO 566
<211> LENGTH: 9
<212> TYPE: DNA
<213> ORGANISM: Artificial Sequence
<220> FEATURE:
<223> OTHER INFORMATION: Barcoding sequence

<400> SEQUENCE: 566 cattcggaa                                                                 9

<210> SEQ ID NO 567
<211> LENGTH: 9
<212> TYPE: DNA
<213> ORGANISM: Artificial Sequence
<220> FEATURE:
<223> OTHER INFORMATION: Barcoding sequence

<400> SEQUENCE: 567 agttcggaa                                                                 9

<210> SEQ ID NO 568
<211> LENGTH: 9
<212> TYPE: DNA
<213> ORGANISM: Artificial Sequence
<220> FEATURE:
<223> OTHER INFORMATION: Barcoding sequence

<400> SEQUENCE: 568 tcttcggaa                                                                 9

<210> SEQ ID NO 569
<211> LENGTH: 9
<212> TYPE: DNA
<213> ORGANISM: Artificial Sequence
<220> FEATURE:
<223> OTHER INFORMATION: Barcoding sequence

<400> SEQUENCE: 569 ggaatggaa                                                                 9

<210> SEQ ID NO 570
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 570 ccaatggaa                                                         9

<210> SEQ ID NO 571
<211> LENGTH: 9
<212> TYPE: DNA
<213> ORGANISM: Artificial Sequence
<220> FEATURE:
<223> OTHER INFORMATION: Barcoding sequence

<400> SEQUENCE: 571 cagatggaa                                                         9

<210> SEQ ID NO 572
<211> LENGTH: 9
<212> TYPE: DNA
<213> ORGANISM: Artificial Sequence
<220> FEATURE:
<223> OTHER INFORMATION: Barcoding sequence

<400> SEQUENCE: 572 tggatggaa                                                         9

<210> SEQ ID NO 573
<211> LENGTH: 9
<212> TYPE: DNA
<213> ORGANISM: Artificial Sequence
<220> FEATURE:
<223> OTHER INFORMATION: Barcoding sequence

<400> SEQUENCE: 573 acgatggaa                                                         9

<210> SEQ ID NO 574
<211> LENGTH: 9
<212> TYPE: DNA
<213> ORGANISM: Artificial Sequence
<220> FEATURE:
<223> OTHER INFORMATION: Barcoding sequence

<400> SEQUENCE: 574 gtgatggaa                                                         9

<210> SEQ ID NO 575
<211> LENGTH: 9
<212> TYPE: DNA
<213> ORGANISM: Artificial Sequence
<220> FEATURE:
<223> OTHER INFORMATION: Barcoding sequence

<400> SEQUENCE: 575 gacatggaa                                                         9

<210> SEQ ID NO 576
<211> LENGTH: 9
<212> TYPE: DNA
<213> ORGANISM: Artificial Sequence
<220> FEATURE:
<223> OTHER INFORMATION: Barcoding sequence

<400> SEQUENCE: 576 agcatggaa                                                         9

<210> SEQ ID NO 577
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 577 ctcatggaa                                                                 9

<210> SEQ ID NO 578
<211> LENGTH: 9
<212> TYPE: DNA
<213> ORGANISM: Artificial Sequence
<220> FEATURE:
<223> OTHER INFORMATION: Barcoding sequence

<400> SEQUENCE: 578 cgtatggaa                                                                 9

<210> SEQ ID NO 579
<211> LENGTH: 9
<212> TYPE: DNA
<213> ORGANISM: Artificial Sequence
<220> FEATURE:
<223> OTHER INFORMATION: Barcoding sequence

<400> SEQUENCE: 579 gctatggaa                                                                 9

<210> SEQ ID NO 580
<211> LENGTH: 9
<212> TYPE: DNA
<213> ORGANISM: Artificial Sequence
<220> FEATURE:
<223> OTHER INFORMATION: Barcoding sequence

<400> SEQUENCE: 580 caagtggaa                                                                 9

<210> SEQ ID NO 581
<211> LENGTH: 9
<212> TYPE: DNA
<213> ORGANISM: Artificial Sequence
<220> FEATURE:
<223> OTHER INFORMATION: Barcoding sequence

<400> SEQUENCE: 581 tgagtggaa                                                                 9

<210> SEQ ID NO 582
<211> LENGTH: 9
<212> TYPE: DNA
<213> ORGANISM: Artificial Sequence
<220> FEATURE:
<223> OTHER INFORMATION: Barcoding sequence

<400> SEQUENCE: 582 acagtggaa                                                                 9

<210> SEQ ID NO 583
<211> LENGTH: 9
<212> TYPE: DNA
<213> ORGANISM: Artificial Sequence
<220> FEATURE:
<223> OTHER INFORMATION: Barcoding sequence

<400> SEQUENCE: 583
``` gtagtggaa 9

<210> SEQ ID NO 584
<211> LENGTH: 9
<212> TYPE: DNA
<213> ORGANISM: Artificial Sequence
<220> FEATURE:
<223> OTHER INFORMATION: Barcoding sequence

<400> SEQUENCE: 584 taggtggaa 9

<210> SEQ ID NO 585
<211> LENGTH: 9
<212> TYPE: DNA
<213> ORGANISM: Artificial Sequence
<220> FEATURE:
<223> OTHER INFORMATION: Barcoding sequence

<400> SEQUENCE: 585 atggtggaa 9

<210> SEQ ID NO 586
<211> LENGTH: 9
<212> TYPE: DNA
<213> ORGANISM: Artificial Sequence
<220> FEATURE:
<223> OTHER INFORMATION: Barcoding sequence

<400> SEQUENCE: 586 aacgtggaa 9

<210> SEQ ID NO 587
<211> LENGTH: 9
<212> TYPE: DNA
<213> ORGANISM: Artificial Sequence
<220> FEATURE:
<223> OTHER INFORMATION: Barcoding sequence

<400> SEQUENCE: 587 ttcgtggaa 9

<210> SEQ ID NO 588
<211> LENGTH: 9
<212> TYPE: DNA
<213> ORGANISM: Artificial Sequence
<220> FEATURE:
<223> OTHER INFORMATION: Barcoding sequence

<400> SEQUENCE: 588 gatgtggaa 9

<210> SEQ ID NO 589
<211> LENGTH: 9
<212> TYPE: DNA
<213> ORGANISM: Artificial Sequence
<220> FEATURE:
<223> OTHER INFORMATION: Barcoding sequence

<400> SEQUENCE: 589 agtgtggaa 9

<210> SEQ ID NO 590
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 590 tctgtggaa                                                                  9

<210> SEQ ID NO 591
<211> LENGTH: 9
<212> TYPE: DNA
<213> ORGANISM: Artificial Sequence
<220> FEATURE:
<223> OTHER INFORMATION: Barcoding sequence

<400> SEQUENCE: 591 cttgtggaa                                                                  9

<210> SEQ ID NO 592
<211> LENGTH: 9
<212> TYPE: DNA
<213> ORGANISM: Artificial Sequence
<220> FEATURE:
<223> OTHER INFORMATION: Barcoding sequence

<400> SEQUENCE: 592 gaactggaa                                                                  9

<210> SEQ ID NO 593
<211> LENGTH: 9
<212> TYPE: DNA
<213> ORGANISM: Artificial Sequence
<220> FEATURE:
<223> OTHER INFORMATION: Barcoding sequence

<400> SEQUENCE: 593 agactggaa                                                                  9

<210> SEQ ID NO 594
<211> LENGTH: 9
<212> TYPE: DNA
<213> ORGANISM: Artificial Sequence
<220> FEATURE:
<223> OTHER INFORMATION: Barcoding sequence

<400> SEQUENCE: 594 tcactggaa                                                                  9

<210> SEQ ID NO 595
<211> LENGTH: 9
<212> TYPE: DNA
<213> ORGANISM: Artificial Sequence
<220> FEATURE:
<223> OTHER INFORMATION: Barcoding sequence

<400> SEQUENCE: 595 ctactggaa                                                                  9

<210> SEQ ID NO 596
<211> LENGTH: 9
<212> TYPE: DNA
<213> ORGANISM: Artificial Sequence
<220> FEATURE:
<223> OTHER INFORMATION: Barcoding sequence

<400> SEQUENCE: 596 aagctggaa                                                                  9
```

```
<210> SEQ ID NO 597
<211> LENGTH: 9
<212> TYPE: DNA
<213> ORGANISM: Artificial Sequence
<220> FEATURE:
<223> OTHER INFORMATION: Barcoding sequence

<400> SEQUENCE: 597 ttgctggaa                                                                  9

<210> SEQ ID NO 598
<211> LENGTH: 9
<212> TYPE: DNA
<213> ORGANISM: Artificial Sequence
<220> FEATURE:
<223> OTHER INFORMATION: Barcoding sequence

<400> SEQUENCE: 598 tacctggaa                                                                  9

<210> SEQ ID NO 599
<211> LENGTH: 9
<212> TYPE: DNA
<213> ORGANISM: Artificial Sequence
<220> FEATURE:
<223> OTHER INFORMATION: Barcoding sequence

<400> SEQUENCE: 599 atcctggaa                                                                  9

<210> SEQ ID NO 600
<211> LENGTH: 9
<212> TYPE: DNA
<213> ORGANISM: Artificial Sequence
<220> FEATURE:
<223> OTHER INFORMATION: Barcoding sequence

<400> SEQUENCE: 600 catctggaa                                                                  9

<210> SEQ ID NO 601
<211> LENGTH: 9
<212> TYPE: DNA
<213> ORGANISM: Artificial Sequence
<220> FEATURE:
<223> OTHER INFORMATION: Barcoding sequence

<400> SEQUENCE: 601 tgtctggaa                                                                  9

<210> SEQ ID NO 602
<211> LENGTH: 9
<212> TYPE: DNA
<213> ORGANISM: Artificial Sequence
<220> FEATURE:
<223> OTHER INFORMATION: Barcoding sequence

<400> SEQUENCE: 602 actctggaa                                                                  9

<210> SEQ ID NO 603
<211> LENGTH: 9
<212> TYPE: DNA
<213> ORGANISM: Artificial Sequence
<220> FEATURE:
```

-continued

<223> OTHER INFORMATION: Barcoding sequence

<400> SEQUENCE: 603 gttctggaa                                                              9

<210> SEQ ID NO 604
<211> LENGTH: 9
<212> TYPE: DNA
<213> ORGANISM: Artificial Sequence
<220> FEATURE:
<223> OTHER INFORMATION: Barcoding sequence

<400> SEQUENCE: 604 cgattggaa                                                              9

<210> SEQ ID NO 605
<211> LENGTH: 9
<212> TYPE: DNA
<213> ORGANISM: Artificial Sequence
<220> FEATURE:
<223> OTHER INFORMATION: Barcoding sequence

<400> SEQUENCE: 605 gcattggaa                                                              9

<210> SEQ ID NO 606
<211> LENGTH: 9
<212> TYPE: DNA
<213> ORGANISM: Artificial Sequence
<220> FEATURE:
<223> OTHER INFORMATION: Barcoding sequence

<400> SEQUENCE: 606 gagttggaa                                                              9

<210> SEQ ID NO 607
<211> LENGTH: 9
<212> TYPE: DNA
<213> ORGANISM: Artificial Sequence
<220> FEATURE:
<223> OTHER INFORMATION: Barcoding sequence

<400> SEQUENCE: 607 aggttggaa                                                              9

<210> SEQ ID NO 608
<211> LENGTH: 9
<212> TYPE: DNA
<213> ORGANISM: Artificial Sequence
<220> FEATURE:
<223> OTHER INFORMATION: Barcoding sequence

<400> SEQUENCE: 608 tcgttggaa                                                              9

<210> SEQ ID NO 609
<211> LENGTH: 9
<212> TYPE: DNA
<213> ORGANISM: Artificial Sequence
<220> FEATURE:
<223> OTHER INFORMATION: Barcoding sequence

<400> SEQUENCE: 609 ctgttggaa                                                              9

-continued

```
<210> SEQ ID NO 610
<211> LENGTH: 9
<212> TYPE: DNA
<213> ORGANISM: Artificial Sequence
<220> FEATURE:
<223> OTHER INFORMATION: Barcoding sequence

<400> SEQUENCE: 610 cacttggaa                                                                 9

<210> SEQ ID NO 611
<211> LENGTH: 9
<212> TYPE: DNA
<213> ORGANISM: Artificial Sequence
<220> FEATURE:
<223> OTHER INFORMATION: Barcoding sequence

<400> SEQUENCE: 611 tgcttggaa                                                                 9

<210> SEQ ID NO 612
<211> LENGTH: 9
<212> TYPE: DNA
<213> ORGANISM: Artificial Sequence
<220> FEATURE:
<223> OTHER INFORMATION: Barcoding sequence

<400> SEQUENCE: 612 accttggaa                                                                 9

<210> SEQ ID NO 613
<211> LENGTH: 9
<212> TYPE: DNA
<213> ORGANISM: Artificial Sequence
<220> FEATURE:
<223> OTHER INFORMATION: Barcoding sequence

<400> SEQUENCE: 613 gtcttggaa                                                                 9

<210> SEQ ID NO 614
<211> LENGTH: 9
<212> TYPE: DNA
<213> ORGANISM: Artificial Sequence
<220> FEATURE:
<223> OTHER INFORMATION: Barcoding sequence

<400> SEQUENCE: 614 cagaacgaa                                                                 9

<210> SEQ ID NO 615
<211> LENGTH: 9
<212> TYPE: DNA
<213> ORGANISM: Artificial Sequence
<220> FEATURE:
<223> OTHER INFORMATION: Barcoding sequence

<400> SEQUENCE: 615 tggaacgaa                                                                 9

<210> SEQ ID NO 616
<211> LENGTH: 9
<212> TYPE: DNA
<213> ORGANISM: Artificial Sequence
<220> FEATURE:
<223> OTHER INFORMATION: Barcoding sequence
```

<400> SEQUENCE: 616 acgaacgaa                                                                9

<210> SEQ ID NO 617
<211> LENGTH: 9
<212> TYPE: DNA
<213> ORGANISM: Artificial Sequence
<220> FEATURE:
<223> OTHER INFORMATION: Barcoding sequence

<400> SEQUENCE: 617 gtgaacgaa                                                                9

<210> SEQ ID NO 618
<211> LENGTH: 9
<212> TYPE: DNA
<213> ORGANISM: Artificial Sequence
<220> FEATURE:
<223> OTHER INFORMATION: Barcoding sequence

<400> SEQUENCE: 618 gacaacgaa                                                                9

<210> SEQ ID NO 619
<211> LENGTH: 9
<212> TYPE: DNA
<213> ORGANISM: Artificial Sequence
<220> FEATURE:
<223> OTHER INFORMATION: Barcoding sequence

<400> SEQUENCE: 619 agcaacgaa                                                                9

<210> SEQ ID NO 620
<211> LENGTH: 9
<212> TYPE: DNA
<213> ORGANISM: Artificial Sequence
<220> FEATURE:
<223> OTHER INFORMATION: Barcoding sequence

<400> SEQUENCE: 620 tccaacgaa                                                                9

<210> SEQ ID NO 621
<211> LENGTH: 9
<212> TYPE: DNA
<213> ORGANISM: Artificial Sequence
<220> FEATURE:
<223> OTHER INFORMATION: Barcoding sequence

<400> SEQUENCE: 621 ctcaacgaa                                                                9

<210> SEQ ID NO 622
<211> LENGTH: 9
<212> TYPE: DNA
<213> ORGANISM: Artificial Sequence
<220> FEATURE:
<223> OTHER INFORMATION: Barcoding sequence

<400> SEQUENCE: 622 cgtaacgaa                                                                9

<210> SEQ ID NO 623
<211> LENGTH: 9

```
<212> TYPE: DNA
<213> ORGANISM: Artificial Sequence
<220> FEATURE:
<223> OTHER INFORMATION: Barcoding sequence

<400> SEQUENCE: 623 gctaacgaa                                                                    9

<210> SEQ ID NO 624
<211> LENGTH: 9
<212> TYPE: DNA
<213> ORGANISM: Artificial Sequence
<220> FEATURE:
<223> OTHER INFORMATION: Barcoding sequence

<400> SEQUENCE: 624 caagacgaa                                                                    9

<210> SEQ ID NO 625
<211> LENGTH: 9
<212> TYPE: DNA
<213> ORGANISM: Artificial Sequence
<220> FEATURE:
<223> OTHER INFORMATION: Barcoding sequence

<400> SEQUENCE: 625 tgagacgaa                                                                    9

<210> SEQ ID NO 626
<211> LENGTH: 9
<212> TYPE: DNA
<213> ORGANISM: Artificial Sequence
<220> FEATURE:
<223> OTHER INFORMATION: Barcoding sequence

<400> SEQUENCE: 626 acagacgaa                                                                    9

<210> SEQ ID NO 627
<211> LENGTH: 9
<212> TYPE: DNA
<213> ORGANISM: Artificial Sequence
<220> FEATURE:
<223> OTHER INFORMATION: Barcoding sequence

<400> SEQUENCE: 627 gtagacgaa                                                                    9

<210> SEQ ID NO 628
<211> LENGTH: 9
<212> TYPE: DNA
<213> ORGANISM: Artificial Sequence
<220> FEATURE:
<223> OTHER INFORMATION: Barcoding sequence

<400> SEQUENCE: 628 taggacgaa                                                                    9

<210> SEQ ID NO 629
<211> LENGTH: 9
<212> TYPE: DNA
<213> ORGANISM: Artificial Sequence
<220> FEATURE:
<223> OTHER INFORMATION: Barcoding sequence

<400> SEQUENCE: 629
``` atggacgaa                                                                    9

<210> SEQ ID NO 630
<211> LENGTH: 9
<212> TYPE: DNA
<213> ORGANISM: Artificial Sequence
<220> FEATURE:
<223> OTHER INFORMATION: Barcoding sequence

<400> SEQUENCE: 630 aacgacgaa                                                                    9

<210> SEQ ID NO 631
<211> LENGTH: 9
<212> TYPE: DNA
<213> ORGANISM: Artificial Sequence
<220> FEATURE:
<223> OTHER INFORMATION: Barcoding sequence

<400> SEQUENCE: 631 ttcgacgaa                                                                    9

<210> SEQ ID NO 632
<211> LENGTH: 9
<212> TYPE: DNA
<213> ORGANISM: Artificial Sequence
<220> FEATURE:
<223> OTHER INFORMATION: Barcoding sequence

<400> SEQUENCE: 632 gatgacgaa                                                                    9

<210> SEQ ID NO 633
<211> LENGTH: 9
<212> TYPE: DNA
<213> ORGANISM: Artificial Sequence
<220> FEATURE:
<223> OTHER INFORMATION: Barcoding sequence

<400> SEQUENCE: 633 agtgacgaa                                                                    9

<210> SEQ ID NO 634
<211> LENGTH: 9
<212> TYPE: DNA
<213> ORGANISM: Artificial Sequence
<220> FEATURE:
<223> OTHER INFORMATION: Barcoding sequence

<400> SEQUENCE: 634 tctgacgaa                                                                    9

<210> SEQ ID NO 635
<211> LENGTH: 9
<212> TYPE: DNA
<213> ORGANISM: Artificial Sequence
<220> FEATURE:
<223> OTHER INFORMATION: Barcoding sequence

<400> SEQUENCE: 635 cttgacgaa                                                                    9

<210> SEQ ID NO 636
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 636 gaacacgaa                                                                9

<210> SEQ ID NO 637
<211> LENGTH: 9
<212> TYPE: DNA
<213> ORGANISM: Artificial Sequence
<220> FEATURE:
<223> OTHER INFORMATION: Barcoding sequence

<400> SEQUENCE: 637 agacacgaa                                                                9

<210> SEQ ID NO 638
<211> LENGTH: 9
<212> TYPE: DNA
<213> ORGANISM: Artificial Sequence
<220> FEATURE:
<223> OTHER INFORMATION: Barcoding sequence

<400> SEQUENCE: 638 tcacacgaa                                                                9

<210> SEQ ID NO 639
<211> LENGTH: 9
<212> TYPE: DNA
<213> ORGANISM: Artificial Sequence
<220> FEATURE:
<223> OTHER INFORMATION: Barcoding sequence

<400> SEQUENCE: 639 ctacacgaa                                                                9

<210> SEQ ID NO 640
<211> LENGTH: 9
<212> TYPE: DNA
<213> ORGANISM: Artificial Sequence
<220> FEATURE:
<223> OTHER INFORMATION: Barcoding sequence

<400> SEQUENCE: 640 aagcacgaa                                                                9

<210> SEQ ID NO 641
<211> LENGTH: 9
<212> TYPE: DNA
<213> ORGANISM: Artificial Sequence
<220> FEATURE:
<223> OTHER INFORMATION: Barcoding sequence

<400> SEQUENCE: 641 ttgcacgaa                                                                9

<210> SEQ ID NO 642
<211> LENGTH: 9
<212> TYPE: DNA
<213> ORGANISM: Artificial Sequence
<220> FEATURE:
<223> OTHER INFORMATION: Barcoding sequence

<400> SEQUENCE: 642 taccacgaa                                                                9
```

```
<210> SEQ ID NO 643
<211> LENGTH: 9
<212> TYPE: DNA
<213> ORGANISM: Artificial Sequence
<220> FEATURE:
<223> OTHER INFORMATION: Barcoding sequence

<400> SEQUENCE: 643 atccacgaa                                                                9

<210> SEQ ID NO 644
<211> LENGTH: 9
<212> TYPE: DNA
<213> ORGANISM: Artificial Sequence
<220> FEATURE:
<223> OTHER INFORMATION: Barcoding sequence

<400> SEQUENCE: 644 catcacgaa                                                                9

<210> SEQ ID NO 645
<211> LENGTH: 9
<212> TYPE: DNA
<213> ORGANISM: Artificial Sequence
<220> FEATURE:
<223> OTHER INFORMATION: Barcoding sequence

<400> SEQUENCE: 645 tgtcacgaa                                                                9

<210> SEQ ID NO 646
<211> LENGTH: 9
<212> TYPE: DNA
<213> ORGANISM: Artificial Sequence
<220> FEATURE:
<223> OTHER INFORMATION: Barcoding sequence

<400> SEQUENCE: 646 actcacgaa                                                                9

<210> SEQ ID NO 647
<211> LENGTH: 9
<212> TYPE: DNA
<213> ORGANISM: Artificial Sequence
<220> FEATURE:
<223> OTHER INFORMATION: Barcoding sequence

<400> SEQUENCE: 647 gttcacgaa                                                                9

<210> SEQ ID NO 648
<211> LENGTH: 9
<212> TYPE: DNA
<213> ORGANISM: Artificial Sequence
<220> FEATURE:
<223> OTHER INFORMATION: Barcoding sequence

<400> SEQUENCE: 648 cgatacgaa                                                                9

<210> SEQ ID NO 649
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 649 gcatacgaa                                                          9

<210> SEQ ID NO 650
<211> LENGTH: 9
<212> TYPE: DNA
<213> ORGANISM: Artificial Sequence
<220> FEATURE:
<223> OTHER INFORMATION: Barcoding sequence

<400> SEQUENCE: 650 gagtacgaa                                                          9

<210> SEQ ID NO 651
<211> LENGTH: 9
<212> TYPE: DNA
<213> ORGANISM: Artificial Sequence
<220> FEATURE:
<223> OTHER INFORMATION: Barcoding sequence

<400> SEQUENCE: 651 aggtacgaa                                                          9

<210> SEQ ID NO 652
<211> LENGTH: 9
<212> TYPE: DNA
<213> ORGANISM: Artificial Sequence
<220> FEATURE:
<223> OTHER INFORMATION: Barcoding sequence

<400> SEQUENCE: 652 ctgtacgaa                                                          9

<210> SEQ ID NO 653
<211> LENGTH: 9
<212> TYPE: DNA
<213> ORGANISM: Artificial Sequence
<220> FEATURE:
<223> OTHER INFORMATION: Barcoding sequence

<400> SEQUENCE: 653 cactacgaa                                                          9

<210> SEQ ID NO 654
<211> LENGTH: 9
<212> TYPE: DNA
<213> ORGANISM: Artificial Sequence
<220> FEATURE:
<223> OTHER INFORMATION: Barcoding sequence

<400> SEQUENCE: 654 tgctacgaa                                                          9

<210> SEQ ID NO 655
<211> LENGTH: 9
<212> TYPE: DNA
<213> ORGANISM: Artificial Sequence
<220> FEATURE:
<223> OTHER INFORMATION: Barcoding sequence

<400> SEQUENCE: 655 acctacgaa                                                          9

<210> SEQ ID NO 656
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 656 gtctacgaa                                                                9

<210> SEQ ID NO 657
<211> LENGTH: 9
<212> TYPE: DNA
<213> ORGANISM: Artificial Sequence
<220> FEATURE:
<223> OTHER INFORMATION: Barcoding sequence

<400> SEQUENCE: 657 ggttacgaa                                                                9

<210> SEQ ID NO 658
<211> LENGTH: 9
<212> TYPE: DNA
<213> ORGANISM: Artificial Sequence
<220> FEATURE:
<223> OTHER INFORMATION: Barcoding sequence

<400> SEQUENCE: 658 ccttacgaa                                                                9

<210> SEQ ID NO 659
<211> LENGTH: 9
<212> TYPE: DNA
<213> ORGANISM: Artificial Sequence
<220> FEATURE:
<223> OTHER INFORMATION: Barcoding sequence

<400> SEQUENCE: 659 agaagcgaa                                                                9

<210> SEQ ID NO 660
<211> LENGTH: 9
<212> TYPE: DNA
<213> ORGANISM: Artificial Sequence
<220> FEATURE:
<223> OTHER INFORMATION: Barcoding sequence

<400> SEQUENCE: 660 tcaagcgaa                                                                9

<210> SEQ ID NO 661
<211> LENGTH: 9
<212> TYPE: DNA
<213> ORGANISM: Artificial Sequence
<220> FEATURE:
<223> OTHER INFORMATION: Barcoding sequence

<400> SEQUENCE: 661 gtaagcgaa                                                                9

<210> SEQ ID NO 662
<211> LENGTH: 9
<212> TYPE: DNA
<213> ORGANISM: Artificial Sequence
<220> FEATURE:
<223> OTHER INFORMATION: Barcoding sequence

<400> SEQUENCE: 662
``` aagagcgaa                                                                9

<210> SEQ ID NO 663
<211> LENGTH: 9
<212> TYPE: DNA
<213> ORGANISM: Artificial Sequence
<220> FEATURE:
<223> OTHER INFORMATION: Barcoding sequence

<400> SEQUENCE: 663 ttgagcgaa                                                                9

<210> SEQ ID NO 664
<211> LENGTH: 9
<212> TYPE: DNA
<213> ORGANISM: Artificial Sequence
<220> FEATURE:
<223> OTHER INFORMATION: Barcoding sequence

<400> SEQUENCE: 664 tacagcgaa                                                                9

<210> SEQ ID NO 665
<211> LENGTH: 9
<212> TYPE: DNA
<213> ORGANISM: Artificial Sequence
<220> FEATURE:
<223> OTHER INFORMATION: Barcoding sequence

<400> SEQUENCE: 665 atcagcgaa                                                                9

<210> SEQ ID NO 666
<211> LENGTH: 9
<212> TYPE: DNA
<213> ORGANISM: Artificial Sequence
<220> FEATURE:
<223> OTHER INFORMATION: Barcoding sequence

<400> SEQUENCE: 666 gatagcgaa                                                                9

<210> SEQ ID NO 667
<211> LENGTH: 9
<212> TYPE: DNA
<213> ORGANISM: Artificial Sequence
<220> FEATURE:
<223> OTHER INFORMATION: Barcoding sequence

<400> SEQUENCE: 667 tgtagcgaa                                                                9

<210> SEQ ID NO 668
<211> LENGTH: 9
<212> TYPE: DNA
<213> ORGANISM: Artificial Sequence
<220> FEATURE:
<223> OTHER INFORMATION: Barcoding sequence

<400> SEQUENCE: 668 actagcgaa                                                                9

<210> SEQ ID NO 669
<211> LENGTH: 9
<212> TYPE: DNA

<213> ORGANISM: Artificial Sequence
<220> FEATURE:
<223> OTHER INFORMATION: Barcoding sequence

<400> SEQUENCE: 669 cttagcgaa                                                                9

<210> SEQ ID NO 670
<211> LENGTH: 9
<212> TYPE: DNA
<213> ORGANISM: Artificial Sequence
<220> FEATURE:
<223> OTHER INFORMATION: Barcoding sequence

<400> SEQUENCE: 670 taaggcgaa                                                                9

<210> SEQ ID NO 671
<211> LENGTH: 9
<212> TYPE: DNA
<213> ORGANISM: Artificial Sequence
<220> FEATURE:
<223> OTHER INFORMATION: Barcoding sequence

<400> SEQUENCE: 671 ataggcgaa                                                                9

<210> SEQ ID NO 672
<211> LENGTH: 9
<212> TYPE: DNA
<213> ORGANISM: Artificial Sequence
<220> FEATURE:
<223> OTHER INFORMATION: Barcoding sequence

<400> SEQUENCE: 672 aatggcgaa                                                                9

<210> SEQ ID NO 673
<211> LENGTH: 9
<212> TYPE: DNA
<213> ORGANISM: Artificial Sequence
<220> FEATURE:
<223> OTHER INFORMATION: Barcoding sequence

<400> SEQUENCE: 673 ttacgcgaa                                                                9

<210> SEQ ID NO 674
<211> LENGTH: 9
<212> TYPE: DNA
<213> ORGANISM: Artificial Sequence
<220> FEATURE:
<223> OTHER INFORMATION: Barcoding sequence

<400> SEQUENCE: 674 tatcgcgaa                                                                9

<210> SEQ ID NO 675
<211> LENGTH: 9
<212> TYPE: DNA
<213> ORGANISM: Artificial Sequence
<220> FEATURE:
<223> OTHER INFORMATION: Barcoding sequence

<400> SEQUENCE: 675 attcgcgaa                                                                9

```
<210> SEQ ID NO 676
<211> LENGTH: 9
<212> TYPE: DNA
<213> ORGANISM: Artificial Sequence
<220> FEATURE:
<223> OTHER INFORMATION: Barcoding sequence

<400> SEQUENCE: 676 gaatgcgaa                                                                 9

<210> SEQ ID NO 677
<211> LENGTH: 9
<212> TYPE: DNA
<213> ORGANISM: Artificial Sequence
<220> FEATURE:
<223> OTHER INFORMATION: Barcoding sequence

<400> SEQUENCE: 677 tgatgcgaa                                                                 9

<210> SEQ ID NO 678
<211> LENGTH: 9
<212> TYPE: DNA
<213> ORGANISM: Artificial Sequence
<220> FEATURE:
<223> OTHER INFORMATION: Barcoding sequence

<400> SEQUENCE: 678 acatgcgaa                                                                 9

<210> SEQ ID NO 679
<211> LENGTH: 9
<212> TYPE: DNA
<213> ORGANISM: Artificial Sequence
<220> FEATURE:
<223> OTHER INFORMATION: Barcoding sequence

<400> SEQUENCE: 679 ctatgcgaa                                                                 9

<210> SEQ ID NO 680
<211> LENGTH: 9
<212> TYPE: DNA
<213> ORGANISM: Artificial Sequence
<220> FEATURE:
<223> OTHER INFORMATION: Barcoding sequence

<400> SEQUENCE: 680 tagtgcgaa                                                                 9

<210> SEQ ID NO 681
<211> LENGTH: 9
<212> TYPE: DNA
<213> ORGANISM: Artificial Sequence
<220> FEATURE:
<223> OTHER INFORMATION: Barcoding sequence

<400> SEQUENCE: 681 atgtgcgaa                                                                 9

<210> SEQ ID NO 682
<211> LENGTH: 9
<212> TYPE: DNA
<213> ORGANISM: Artificial Sequence
<220> FEATURE:
```

-continued

```
<223> OTHER INFORMATION: Barcoding sequence

<400> SEQUENCE: 682 aactgcgaa                                                              9

<210> SEQ ID NO 683
<211> LENGTH: 9
<212> TYPE: DNA
<213> ORGANISM: Artificial Sequence
<220> FEATURE:
<223> OTHER INFORMATION: Barcoding sequence

<400> SEQUENCE: 683 ttctgcgaa                                                              9

<210> SEQ ID NO 684
<211> LENGTH: 9
<212> TYPE: DNA
<213> ORGANISM: Artificial Sequence
<220> FEATURE:
<223> OTHER INFORMATION: Barcoding sequence

<400> SEQUENCE: 684 cattgcgaa                                                              9

<210> SEQ ID NO 685
<211> LENGTH: 9
<212> TYPE: DNA
<213> ORGANISM: Artificial Sequence
<220> FEATURE:
<223> OTHER INFORMATION: Barcoding sequence

<400> SEQUENCE: 685 agttgcgaa                                                              9

<210> SEQ ID NO 686
<211> LENGTH: 9
<212> TYPE: DNA
<213> ORGANISM: Artificial Sequence
<220> FEATURE:
<223> OTHER INFORMATION: Barcoding sequence

<400> SEQUENCE: 686 tcttgcgaa                                                              9

<210> SEQ ID NO 687
<211> LENGTH: 9
<212> TYPE: DNA
<213> ORGANISM: Artificial Sequence
<220> FEATURE:
<223> OTHER INFORMATION: Barcoding sequence

<400> SEQUENCE: 687 tgaaccgaa                                                              9

<210> SEQ ID NO 688
<211> LENGTH: 9
<212> TYPE: DNA
<213> ORGANISM: Artificial Sequence
<220> FEATURE:
<223> OTHER INFORMATION: Barcoding sequence

<400> SEQUENCE: 688 acaaccgaa                                                              9
```

```
<210> SEQ ID NO 689
<211> LENGTH: 9
<212> TYPE: DNA
<213> ORGANISM: Artificial Sequence
<220> FEATURE:
<223> OTHER INFORMATION: Barcoding sequence

<400> SEQUENCE: 689 ctaaccgaa                                                                 9

<210> SEQ ID NO 690
<211> LENGTH: 9
<212> TYPE: DNA
<213> ORGANISM: Artificial Sequence
<220> FEATURE:
<223> OTHER INFORMATION: Barcoding sequence

<400> SEQUENCE: 690 tagaccgaa                                                                 9

<210> SEQ ID NO 691
<211> LENGTH: 9
<212> TYPE: DNA
<213> ORGANISM: Artificial Sequence
<220> FEATURE:
<223> OTHER INFORMATION: Barcoding sequence

<400> SEQUENCE: 691 atgaccgaa                                                                 9

<210> SEQ ID NO 692
<211> LENGTH: 9
<212> TYPE: DNA
<213> ORGANISM: Artificial Sequence
<220> FEATURE:
<223> OTHER INFORMATION: Barcoding sequence

<400> SEQUENCE: 692 aacaccgaa                                                                 9

<210> SEQ ID NO 693
<211> LENGTH: 9
<212> TYPE: DNA
<213> ORGANISM: Artificial Sequence
<220> FEATURE:
<223> OTHER INFORMATION: Barcoding sequence

<400> SEQUENCE: 693 ttcaccgaa                                                                 9

<210> SEQ ID NO 694
<211> LENGTH: 9
<212> TYPE: DNA
<213> ORGANISM: Artificial Sequence
<220> FEATURE:
<223> OTHER INFORMATION: Barcoding sequence

<400> SEQUENCE: 694 cataccgaa                                                                 9

<210> SEQ ID NO 695
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 695 agtaccgaa                                                                9

<210> SEQ ID NO 696
<211> LENGTH: 9
<212> TYPE: DNA
<213> ORGANISM: Artificial Sequence
<220> FEATURE:
<223> OTHER INFORMATION: Barcoding sequence

<400> SEQUENCE: 696 tctaccgaa                                                                9

<210> SEQ ID NO 697
<211> LENGTH: 9
<212> TYPE: DNA
<213> ORGANISM: Artificial Sequence
<220> FEATURE:
<223> OTHER INFORMATION: Barcoding sequence

<400> SEQUENCE: 697 gttaccgaa                                                                9

<210> SEQ ID NO 698
<211> LENGTH: 9
<212> TYPE: DNA
<213> ORGANISM: Artificial Sequence
<220> FEATURE:
<223> OTHER INFORMATION: Barcoding sequence

<400> SEQUENCE: 698 ttagccgaa                                                                9

<210> SEQ ID NO 699
<211> LENGTH: 9
<212> TYPE: DNA
<213> ORGANISM: Artificial Sequence
<220> FEATURE:
<223> OTHER INFORMATION: Barcoding sequence

<400> SEQUENCE: 699 tatgccgaa                                                                9

<210> SEQ ID NO 700
<211> LENGTH: 9
<212> TYPE: DNA
<213> ORGANISM: Artificial Sequence
<220> FEATURE:
<223> OTHER INFORMATION: Barcoding sequence

<400> SEQUENCE: 700 attgccgaa                                                                9

<210> SEQ ID NO 701
<211> LENGTH: 9
<212> TYPE: DNA
<213> ORGANISM: Artificial Sequence
<220> FEATURE:
<223> OTHER INFORMATION: Barcoding sequence

<400> SEQUENCE: 701 caatccgaa                                                                9

<210> SEQ ID NO 702
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 702 agatccgaa                                                                9

<210> SEQ ID NO 703
<211> LENGTH: 9
<212> TYPE: DNA
<213> ORGANISM: Artificial Sequence
<220> FEATURE:
<223> OTHER INFORMATION: Barcoding sequence

<400> SEQUENCE: 703 tcatccgaa                                                                9

<210> SEQ ID NO 704
<211> LENGTH: 9
<212> TYPE: DNA
<213> ORGANISM: Artificial Sequence
<220> FEATURE:
<223> OTHER INFORMATION: Barcoding sequence

<400> SEQUENCE: 704 gtatccgaa                                                                9

<210> SEQ ID NO 705
<211> LENGTH: 9
<212> TYPE: DNA
<213> ORGANISM: Artificial Sequence
<220> FEATURE:
<223> OTHER INFORMATION: Barcoding sequence

<400> SEQUENCE: 705 aagtccgaa                                                                9

<210> SEQ ID NO 706
<211> LENGTH: 9
<212> TYPE: DNA
<213> ORGANISM: Artificial Sequence
<220> FEATURE:
<223> OTHER INFORMATION: Barcoding sequence

<400> SEQUENCE: 706 ttgtccgaa                                                                9

<210> SEQ ID NO 707
<211> LENGTH: 9
<212> TYPE: DNA
<213> ORGANISM: Artificial Sequence
<220> FEATURE:
<223> OTHER INFORMATION: Barcoding sequence

<400> SEQUENCE: 707 tactccgaa                                                                9

<210> SEQ ID NO 708
<211> LENGTH: 9
<212> TYPE: DNA
<213> ORGANISM: Artificial Sequence
<220> FEATURE:
<223> OTHER INFORMATION: Barcoding sequence

<400> SEQUENCE: 708
```

-continued atctccgaa 9

<210> SEQ ID NO 709
<211> LENGTH: 9
<212> TYPE: DNA
<213> ORGANISM: Artificial Sequence
<220> FEATURE:
<223> OTHER INFORMATION: Barcoding sequence

<400> SEQUENCE: 709 gattccgaa 9

<210> SEQ ID NO 710
<211> LENGTH: 9
<212> TYPE: DNA
<213> ORGANISM: Artificial Sequence
<220> FEATURE:
<223> OTHER INFORMATION: Barcoding sequence

<400> SEQUENCE: 710 tgttccgaa 9

<210> SEQ ID NO 711
<211> LENGTH: 9
<212> TYPE: DNA
<213> ORGANISM: Artificial Sequence
<220> FEATURE:
<223> OTHER INFORMATION: Barcoding sequence

<400> SEQUENCE: 711 acttccgaa 9

<210> SEQ ID NO 712
<211> LENGTH: 9
<212> TYPE: DNA
<213> ORGANISM: Artificial Sequence
<220> FEATURE:
<223> OTHER INFORMATION: Barcoding sequence

<400> SEQUENCE: 712 cgaatcgaa 9

<210> SEQ ID NO 713
<211> LENGTH: 9
<212> TYPE: DNA
<213> ORGANISM: Artificial Sequence
<220> FEATURE:
<223> OTHER INFORMATION: Barcoding sequence

<400> SEQUENCE: 713 gcaatcgaa 9

<210> SEQ ID NO 714
<211> LENGTH: 9
<212> TYPE: DNA
<213> ORGANISM: Artificial Sequence
<220> FEATURE:
<223> OTHER INFORMATION: Barcoding sequence

<400> SEQUENCE: 714 gagatcgaa 9

<210> SEQ ID NO 715
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 715 aggatcgaa                                                                           9

<210> SEQ ID NO 716
<211> LENGTH: 9
<212> TYPE: DNA
<213> ORGANISM: Artificial Sequence
<220> FEATURE:
<223> OTHER INFORMATION: Barcoding sequence

<400> SEQUENCE: 716 ctgatcgaa                                                                           9

<210> SEQ ID NO 717
<211> LENGTH: 9
<212> TYPE: DNA
<213> ORGANISM: Artificial Sequence
<220> FEATURE:
<223> OTHER INFORMATION: Barcoding sequence

<400> SEQUENCE: 717 cacatcgaa                                                                           9

<210> SEQ ID NO 718
<211> LENGTH: 9
<212> TYPE: DNA
<213> ORGANISM: Artificial Sequence
<220> FEATURE:
<223> OTHER INFORMATION: Barcoding sequence

<400> SEQUENCE: 718 tgcatcgaa                                                                           9

<210> SEQ ID NO 719
<211> LENGTH: 9
<212> TYPE: DNA
<213> ORGANISM: Artificial Sequence
<220> FEATURE:
<223> OTHER INFORMATION: Barcoding sequence

<400> SEQUENCE: 719 accatcgaa                                                                           9

<210> SEQ ID NO 720
<211> LENGTH: 9
<212> TYPE: DNA
<213> ORGANISM: Artificial Sequence
<220> FEATURE:
<223> OTHER INFORMATION: Barcoding sequence

<400> SEQUENCE: 720 gtcatcgaa                                                                           9

<210> SEQ ID NO 721
<211> LENGTH: 9
<212> TYPE: DNA
<213> ORGANISM: Artificial Sequence
<220> FEATURE:
<223> OTHER INFORMATION: Barcoding sequence

<400> SEQUENCE: 721 ggtatcgaa                                                                           9
```

<210> SEQ ID NO 722
<211> LENGTH: 9
<212> TYPE: DNA
<213> ORGANISM: Artificial Sequence
<220> FEATURE:
<223> OTHER INFORMATION: Barcoding sequence

<400> SEQUENCE: 722 cctatcgaa                                                                 9

<210> SEQ ID NO 723
<211> LENGTH: 9
<212> TYPE: DNA
<213> ORGANISM: Artificial Sequence
<220> FEATURE:
<223> OTHER INFORMATION: Barcoding sequence

<400> SEQUENCE: 723 gaagtcgaa                                                                 9

<210> SEQ ID NO 724
<211> LENGTH: 9
<212> TYPE: DNA
<213> ORGANISM: Artificial Sequence
<220> FEATURE:
<223> OTHER INFORMATION: Barcoding sequence

<400> SEQUENCE: 724 agagtcgaa                                                                 9

<210> SEQ ID NO 725
<211> LENGTH: 9
<212> TYPE: DNA
<213> ORGANISM: Artificial Sequence
<220> FEATURE:
<223> OTHER INFORMATION: Barcoding sequence

<400> SEQUENCE: 725 tcagtcgaa                                                                 9

<210> SEQ ID NO 726
<211> LENGTH: 9
<212> TYPE: DNA
<213> ORGANISM: Artificial Sequence
<220> FEATURE:
<223> OTHER INFORMATION: Barcoding sequence

<400> SEQUENCE: 726 ctagtcgaa                                                                 9

<210> SEQ ID NO 727
<211> LENGTH: 9
<212> TYPE: DNA
<213> ORGANISM: Artificial Sequence
<220> FEATURE:
<223> OTHER INFORMATION: Barcoding sequence

<400> SEQUENCE: 727 aaggtcgaa                                                                 9

<210> SEQ ID NO 728
<211> LENGTH: 9
<212> TYPE: DNA
<213> ORGANISM: Artificial Sequence
<220> FEATURE:
<223> OTHER INFORMATION: Barcoding sequence

```
<400> SEQUENCE: 728 ttggtcgaa                                                                9

<210> SEQ ID NO 729
<211> LENGTH: 9
<212> TYPE: DNA
<213> ORGANISM: Artificial Sequence
<220> FEATURE:
<223> OTHER INFORMATION: Barcoding sequence

<400> SEQUENCE: 729 tacgtcgaa                                                                9

<210> SEQ ID NO 730
<211> LENGTH: 9
<212> TYPE: DNA
<213> ORGANISM: Artificial Sequence
<220> FEATURE:
<223> OTHER INFORMATION: Barcoding sequence

<400> SEQUENCE: 730 atcgtcgaa                                                                9

<210> SEQ ID NO 731
<211> LENGTH: 9
<212> TYPE: DNA
<213> ORGANISM: Artificial Sequence
<220> FEATURE:
<223> OTHER INFORMATION: Barcoding sequence

<400> SEQUENCE: 731 catgtcgaa                                                                9

<210> SEQ ID NO 732
<211> LENGTH: 9
<212> TYPE: DNA
<213> ORGANISM: Artificial Sequence
<220> FEATURE:
<223> OTHER INFORMATION: Barcoding sequence

<400> SEQUENCE: 732 tgtgtcgaa                                                                9

<210> SEQ ID NO 733
<211> LENGTH: 9
<212> TYPE: DNA
<213> ORGANISM: Artificial Sequence
<220> FEATURE:
<223> OTHER INFORMATION: Barcoding sequence

<400> SEQUENCE: 733 actgtcgaa                                                                9

<210> SEQ ID NO 734
<211> LENGTH: 9
<212> TYPE: DNA
<213> ORGANISM: Artificial Sequence
<220> FEATURE:
<223> OTHER INFORMATION: Barcoding sequence

<400> SEQUENCE: 734 gttgtcgaa                                                                9

<210> SEQ ID NO 735
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 735 caactcgaa                                                                 9

<210> SEQ ID NO 736
<211> LENGTH: 9
<212> TYPE: DNA
<213> ORGANISM: Artificial Sequence
<220> FEATURE:
<223> OTHER INFORMATION: Barcoding sequence

<400> SEQUENCE: 736 tgactcgaa                                                                 9

<210> SEQ ID NO 737
<211> LENGTH: 9
<212> TYPE: DNA
<213> ORGANISM: Artificial Sequence
<220> FEATURE:
<223> OTHER INFORMATION: Barcoding sequence

<400> SEQUENCE: 737 acactcgaa                                                                 9

<210> SEQ ID NO 738
<211> LENGTH: 9
<212> TYPE: DNA
<213> ORGANISM: Artificial Sequence
<220> FEATURE:
<223> OTHER INFORMATION: Barcoding sequence

<400> SEQUENCE: 738 gtactcgaa                                                                 9

<210> SEQ ID NO 739
<211> LENGTH: 9
<212> TYPE: DNA
<213> ORGANISM: Artificial Sequence
<220> FEATURE:
<223> OTHER INFORMATION: Barcoding sequence

<400> SEQUENCE: 739 cggaagaac                                                                 9

<210> SEQ ID NO 740
<211> LENGTH: 9
<212> TYPE: DNA
<213> ORGANISM: Artificial Sequence
<220> FEATURE:
<223> OTHER INFORMATION: Barcoding sequence

<400> SEQUENCE: 740 gcgaagaac                                                                 9

<210> SEQ ID NO 741
<211> LENGTH: 9
<212> TYPE: DNA
<213> ORGANISM: Artificial Sequence
<220> FEATURE:
<223> OTHER INFORMATION: Barcoding sequence

<400> SEQUENCE: 741
``` ggcaagaac 9

<210> SEQ ID NO 742
<211> LENGTH: 9
<212> TYPE: DNA
<213> ORGANISM: Artificial Sequence
<220> FEATURE:
<223> OTHER INFORMATION: Barcoding sequence

<400> SEQUENCE: 742 ggagagaac 9

<210> SEQ ID NO 743
<211> LENGTH: 9
<212> TYPE: DNA
<213> ORGANISM: Artificial Sequence
<220> FEATURE:
<223> OTHER INFORMATION: Barcoding sequence

<400> SEQUENCE: 743 ccagagaac 9

<210> SEQ ID NO 744
<211> LENGTH: 9
<212> TYPE: DNA
<213> ORGANISM: Artificial Sequence
<220> FEATURE:
<223> OTHER INFORMATION: Barcoding sequence

<400> SEQUENCE: 744 gaggagaac 9

<210> SEQ ID NO 745
<211> LENGTH: 9
<212> TYPE: DNA
<213> ORGANISM: Artificial Sequence
<220> FEATURE:
<223> OTHER INFORMATION: Barcoding sequence

<400> SEQUENCE: 745 acggagaac 9

<210> SEQ ID NO 746
<211> LENGTH: 9
<212> TYPE: DNA
<213> ORGANISM: Artificial Sequence
<220> FEATURE:
<223> OTHER INFORMATION: Barcoding sequence

<400> SEQUENCE: 746 ctggagaac 9

<210> SEQ ID NO 747
<211> LENGTH: 9
<212> TYPE: DNA
<213> ORGANISM: Artificial Sequence
<220> FEATURE:
<223> OTHER INFORMATION: Barcoding sequence

<400> SEQUENCE: 747 cacgagaac 9

<210> SEQ ID NO 748
<211> LENGTH: 9
<212> TYPE: DNA

<213> ORGANISM: Artificial Sequence
<220> FEATURE:
<223> OTHER INFORMATION: Barcoding sequence

<400> SEQUENCE: 748 agcgagaac					9

<210> SEQ ID NO 749
<211> LENGTH: 9
<212> TYPE: DNA
<213> ORGANISM: Artificial Sequence
<220> FEATURE:
<223> OTHER INFORMATION: Barcoding sequence

<400> SEQUENCE: 749 tccgagaac					9

<210> SEQ ID NO 750
<211> LENGTH: 9
<212> TYPE: DNA
<213> ORGANISM: Artificial Sequence
<220> FEATURE:
<223> OTHER INFORMATION: Barcoding sequence

<400> SEQUENCE: 750 gtcgagaac					9

<210> SEQ ID NO 751
<211> LENGTH: 9
<212> TYPE: DNA
<213> ORGANISM: Artificial Sequence
<220> FEATURE:
<223> OTHER INFORMATION: Barcoding sequence

<400> SEQUENCE: 751 cgtgagaac					9

<210> SEQ ID NO 752
<211> LENGTH: 9
<212> TYPE: DNA
<213> ORGANISM: Artificial Sequence
<220> FEATURE:
<223> OTHER INFORMATION: Barcoding sequence

<400> SEQUENCE: 752 gctgagaac					9

<210> SEQ ID NO 753
<211> LENGTH: 9
<212> TYPE: DNA
<213> ORGANISM: Artificial Sequence
<220> FEATURE:
<223> OTHER INFORMATION: Barcoding sequence

<400> SEQUENCE: 753 cgacagaac					9

<210> SEQ ID NO 754
<211> LENGTH: 9
<212> TYPE: DNA
<213> ORGANISM: Artificial Sequence
<220> FEATURE:
<223> OTHER INFORMATION: Barcoding sequence

<400> SEQUENCE: 754 gcacagaac					9

```
<210> SEQ ID NO 755
<211> LENGTH: 9
<212> TYPE: DNA
<213> ORGANISM: Artificial Sequence
<220> FEATURE:
<223> OTHER INFORMATION: Barcoding sequence

<400> SEQUENCE: 755 cagcagaac                                                                  9

<210> SEQ ID NO 756
<211> LENGTH: 9
<212> TYPE: DNA
<213> ORGANISM: Artificial Sequence
<220> FEATURE:
<223> OTHER INFORMATION: Barcoding sequence

<400> SEQUENCE: 756 aggcagaac                                                                  9

<210> SEQ ID NO 757
<211> LENGTH: 9
<212> TYPE: DNA
<213> ORGANISM: Artificial Sequence
<220> FEATURE:
<223> OTHER INFORMATION: Barcoding sequence

<400> SEQUENCE: 757 tcgcagaac                                                                  9

<210> SEQ ID NO 758
<211> LENGTH: 9
<212> TYPE: DNA
<213> ORGANISM: Artificial Sequence
<220> FEATURE:
<223> OTHER INFORMATION: Barcoding sequence

<400> SEQUENCE: 758 gtgcagaac                                                                  9

<210> SEQ ID NO 759
<211> LENGTH: 9
<212> TYPE: DNA
<213> ORGANISM: Artificial Sequence
<220> FEATURE:
<223> OTHER INFORMATION: Barcoding sequence

<400> SEQUENCE: 759 gaccagaac                                                                  9

<210> SEQ ID NO 760
<211> LENGTH: 9
<212> TYPE: DNA
<213> ORGANISM: Artificial Sequence
<220> FEATURE:
<223> OTHER INFORMATION: Barcoding sequence

<400> SEQUENCE: 760 tgccagaac                                                                  9

<210> SEQ ID NO 761
<211> LENGTH: 9
<212> TYPE: DNA
<213> ORGANISM: Artificial Sequence
<220> FEATURE:
```

```
<223> OTHER INFORMATION: Barcoding sequence

<400> SEQUENCE: 761 ctccagaac                                                                9

<210> SEQ ID NO 762
<211> LENGTH: 9
<212> TYPE: DNA
<213> ORGANISM: Artificial Sequence
<220> FEATURE:
<223> OTHER INFORMATION: Barcoding sequence

<400> SEQUENCE: 762 ggtcagaac                                                                9

<210> SEQ ID NO 763
<211> LENGTH: 9
<212> TYPE: DNA
<213> ORGANISM: Artificial Sequence
<220> FEATURE:
<223> OTHER INFORMATION: Barcoding sequence

<400> SEQUENCE: 763 cctcagaac                                                                9

<210> SEQ ID NO 764
<211> LENGTH: 9
<212> TYPE: DNA
<213> ORGANISM: Artificial Sequence
<220> FEATURE:
<223> OTHER INFORMATION: Barcoding sequence

<400> SEQUENCE: 764 ccgtagaac                                                                9

<210> SEQ ID NO 765
<211> LENGTH: 9
<212> TYPE: DNA
<213> ORGANISM: Artificial Sequence
<220> FEATURE:
<223> OTHER INFORMATION: Barcoding sequence

<400> SEQUENCE: 765 cgctagaac                                                                9

<210> SEQ ID NO 766
<211> LENGTH: 9
<212> TYPE: DNA
<213> ORGANISM: Artificial Sequence
<220> FEATURE:
<223> OTHER INFORMATION: Barcoding sequence

<400> SEQUENCE: 766 gcctagaac                                                                9

<210> SEQ ID NO 767
<211> LENGTH: 9
<212> TYPE: DNA
<213> ORGANISM: Artificial Sequence
<220> FEATURE:
<223> OTHER INFORMATION: Barcoding sequence

<400> SEQUENCE: 767 ggaaggaac                                                                9
```

```
<210> SEQ ID NO 768
<211> LENGTH: 9
<212> TYPE: DNA
<213> ORGANISM: Artificial Sequence
<220> FEATURE:
<223> OTHER INFORMATION: Barcoding sequence

<400> SEQUENCE: 768 ccaaggaac                                                                 9

<210> SEQ ID NO 769
<211> LENGTH: 9
<212> TYPE: DNA
<213> ORGANISM: Artificial Sequence
<220> FEATURE:
<223> OTHER INFORMATION: Barcoding sequence

<400> SEQUENCE: 769 gagaggaac                                                                 9

<210> SEQ ID NO 770
<211> LENGTH: 9
<212> TYPE: DNA
<213> ORGANISM: Artificial Sequence
<220> FEATURE:
<223> OTHER INFORMATION: Barcoding sequence

<400> SEQUENCE: 770 aggaggaac                                                                 9

<210> SEQ ID NO 771
<211> LENGTH: 9
<212> TYPE: DNA
<213> ORGANISM: Artificial Sequence
<220> FEATURE:
<223> OTHER INFORMATION: Barcoding sequence

<400> SEQUENCE: 771 tcgaggaac                                                                 9

<210> SEQ ID NO 772
<211> LENGTH: 9
<212> TYPE: DNA
<213> ORGANISM: Artificial Sequence
<220> FEATURE:
<223> OTHER INFORMATION: Barcoding sequence

<400> SEQUENCE: 772 ctgaggaac                                                                 9

<210> SEQ ID NO 773
<211> LENGTH: 9
<212> TYPE: DNA
<213> ORGANISM: Artificial Sequence
<220> FEATURE:
<223> OTHER INFORMATION: Barcoding sequence

<400> SEQUENCE: 773 cacaggaac                                                                 9

<210> SEQ ID NO 774
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 774 tgcaggaac                                                              9

<210> SEQ ID NO 775
<211> LENGTH: 9
<212> TYPE: DNA
<213> ORGANISM: Artificial Sequence
<220> FEATURE:
<223> OTHER INFORMATION: Barcoding sequence

<400> SEQUENCE: 775 accaggaac                                                              9

<210> SEQ ID NO 776
<211> LENGTH: 9
<212> TYPE: DNA
<213> ORGANISM: Artificial Sequence
<220> FEATURE:
<223> OTHER INFORMATION: Barcoding sequence

<400> SEQUENCE: 776 gtcaggaac                                                              9

<210> SEQ ID NO 777
<211> LENGTH: 9
<212> TYPE: DNA
<213> ORGANISM: Artificial Sequence
<220> FEATURE:
<223> OTHER INFORMATION: Barcoding sequence

<400> SEQUENCE: 777 cgtaggaac                                                              9

<210> SEQ ID NO 778
<211> LENGTH: 9
<212> TYPE: DNA
<213> ORGANISM: Artificial Sequence
<220> FEATURE:
<223> OTHER INFORMATION: Barcoding sequence

<400> SEQUENCE: 778 gctaggaac                                                              9

<210> SEQ ID NO 779
<211> LENGTH: 9
<212> TYPE: DNA
<213> ORGANISM: Artificial Sequence
<220> FEATURE:
<223> OTHER INFORMATION: Barcoding sequence

<400> SEQUENCE: 779 gaacggaac                                                              9

<210> SEQ ID NO 780
<211> LENGTH: 9
<212> TYPE: DNA
<213> ORGANISM: Artificial Sequence
<220> FEATURE:
<223> OTHER INFORMATION: Barcoding sequence

<400> SEQUENCE: 780 agacggaac                                                              9

<210> SEQ ID NO 781
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 781 tcacggaac                                                                 9

<210> SEQ ID NO 782
<211> LENGTH: 9
<212> TYPE: DNA
<213> ORGANISM: Artificial Sequence
<220> FEATURE:
<223> OTHER INFORMATION: Barcoding sequence

<400> SEQUENCE: 782 ctacggaac                                                                 9

<210> SEQ ID NO 783
<211> LENGTH: 9
<212> TYPE: DNA
<213> ORGANISM: Artificial Sequence
<220> FEATURE:
<223> OTHER INFORMATION: Barcoding sequence

<400> SEQUENCE: 783 aagcggaac                                                                 9

<210> SEQ ID NO 784
<211> LENGTH: 9
<212> TYPE: DNA
<213> ORGANISM: Artificial Sequence
<220> FEATURE:
<223> OTHER INFORMATION: Barcoding sequence

<400> SEQUENCE: 784 ttgcggaac                                                                 9

<210> SEQ ID NO 785
<211> LENGTH: 9
<212> TYPE: DNA
<213> ORGANISM: Artificial Sequence
<220> FEATURE:
<223> OTHER INFORMATION: Barcoding sequence

<400> SEQUENCE: 785 taccggaac                                                                 9

<210> SEQ ID NO 786
<211> LENGTH: 9
<212> TYPE: DNA
<213> ORGANISM: Artificial Sequence
<220> FEATURE:
<223> OTHER INFORMATION: Barcoding sequence

<400> SEQUENCE: 786 atccggaac                                                                 9

<210> SEQ ID NO 787
<211> LENGTH: 9
<212> TYPE: DNA
<213> ORGANISM: Artificial Sequence
<220> FEATURE:
<223> OTHER INFORMATION: Barcoding sequence

<400> SEQUENCE: 787
``` catcggaac 9

<210> SEQ ID NO 788
<211> LENGTH: 9
<212> TYPE: DNA
<213> ORGANISM: Artificial Sequence
<220> FEATURE:
<223> OTHER INFORMATION: Barcoding sequence

<400> SEQUENCE: 788 tgtcggaac 9

<210> SEQ ID NO 789
<211> LENGTH: 9
<212> TYPE: DNA
<213> ORGANISM: Artificial Sequence
<220> FEATURE:
<223> OTHER INFORMATION: Barcoding sequence

<400> SEQUENCE: 789 actcggaac 9

<210> SEQ ID NO 790
<211> LENGTH: 9
<212> TYPE: DNA
<213> ORGANISM: Artificial Sequence
<220> FEATURE:
<223> OTHER INFORMATION: Barcoding sequence

<400> SEQUENCE: 790 gttcggaac 9

<210> SEQ ID NO 791
<211> LENGTH: 9
<212> TYPE: DNA
<213> ORGANISM: Artificial Sequence
<220> FEATURE:
<223> OTHER INFORMATION: Barcoding sequence

<400> SEQUENCE: 791 cgatggaac 9

<210> SEQ ID NO 792
<211> LENGTH: 9
<212> TYPE: DNA
<213> ORGANISM: Artificial Sequence
<220> FEATURE:
<223> OTHER INFORMATION: Barcoding sequence

<400> SEQUENCE: 792 gcatggaac 9

<210> SEQ ID NO 793
<211> LENGTH: 9
<212> TYPE: DNA
<213> ORGANISM: Artificial Sequence
<220> FEATURE:
<223> OTHER INFORMATION: Barcoding sequence

<400> SEQUENCE: 793 cagtggaac 9

<210> SEQ ID NO 794
<211> LENGTH: 9
<212> TYPE: DNA
<213> ORGANISM: Artificial Sequence
<220> FEATURE:
<223> OTHER INFORMATION: Barcoding sequence

<400> SEQUENCE: 794 tggtggaac                                                                                9

<210> SEQ ID NO 795
<211> LENGTH: 9
<212> TYPE: DNA
<213> ORGANISM: Artificial Sequence
<220> FEATURE:
<223> OTHER INFORMATION: Barcoding sequence

<400> SEQUENCE: 795 acgtggaac                                                                                9

<210> SEQ ID NO 796
<211> LENGTH: 9
<212> TYPE: DNA
<213> ORGANISM: Artificial Sequence
<220> FEATURE:
<223> OTHER INFORMATION: Barcoding sequence

<400> SEQUENCE: 796 gtgtggaac                                                                                9

<210> SEQ ID NO 797
<211> LENGTH: 9
<212> TYPE: DNA
<213> ORGANISM: Artificial Sequence
<220> FEATURE:
<223> OTHER INFORMATION: Barcoding sequence

<400> SEQUENCE: 797 gactggaac                                                                                9

<210> SEQ ID NO 798
<211> LENGTH: 9
<212> TYPE: DNA
<213> ORGANISM: Artificial Sequence
<220> FEATURE:
<223> OTHER INFORMATION: Barcoding sequence

<400> SEQUENCE: 798 agctggaac                                                                                9

<210> SEQ ID NO 799
<211> LENGTH: 9
<212> TYPE: DNA
<213> ORGANISM: Artificial Sequence
<220> FEATURE:
<223> OTHER INFORMATION: Barcoding sequence

<400> SEQUENCE: 799 tcctggaac                                                                                9

<210> SEQ ID NO 800
<211> LENGTH: 9
<212> TYPE: DNA
<213> ORGANISM: Artificial Sequence
<220> FEATURE:
<223> OTHER INFORMATION: Barcoding sequence

<400> SEQUENCE: 800 ctctggaac                                                                                9

```
<210> SEQ ID NO 801
<211> LENGTH: 9
<212> TYPE: DNA
<213> ORGANISM: Artificial Sequence
<220> FEATURE:
<223> OTHER INFORMATION: Barcoding sequence

<400> SEQUENCE: 801 ggttggaac                                                                  9

<210> SEQ ID NO 802
<211> LENGTH: 9
<212> TYPE: DNA
<213> ORGANISM: Artificial Sequence
<220> FEATURE:
<223> OTHER INFORMATION: Barcoding sequence

<400> SEQUENCE: 802 ccttggaac                                                                  9

<210> SEQ ID NO 803
<211> LENGTH: 9
<212> TYPE: DNA
<213> ORGANISM: Artificial Sequence
<220> FEATURE:
<223> OTHER INFORMATION: Barcoding sequence

<400> SEQUENCE: 803 cgaacgaac                                                                  9

<210> SEQ ID NO 804
<211> LENGTH: 9
<212> TYPE: DNA
<213> ORGANISM: Artificial Sequence
<220> FEATURE:
<223> OTHER INFORMATION: Barcoding sequence

<400> SEQUENCE: 804 gcaacgaac                                                                  9

<210> SEQ ID NO 805
<211> LENGTH: 9
<212> TYPE: DNA
<213> ORGANISM: Artificial Sequence
<220> FEATURE:
<223> OTHER INFORMATION: Barcoding sequence

<400> SEQUENCE: 805 cagacgaac                                                                  9

<210> SEQ ID NO 806
<211> LENGTH: 9
<212> TYPE: DNA
<213> ORGANISM: Artificial Sequence
<220> FEATURE:
<223> OTHER INFORMATION: Barcoding sequence

<400> SEQUENCE: 806 tggacgaac                                                                  9

<210> SEQ ID NO 807
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 807 acgacgaac                                                              9

<210> SEQ ID NO 808
<211> LENGTH: 9
<212> TYPE: DNA
<213> ORGANISM: Artificial Sequence
<220> FEATURE:
<223> OTHER INFORMATION: Barcoding sequence

<400> SEQUENCE: 808 gtgacgaac                                                              9

<210> SEQ ID NO 809
<211> LENGTH: 9
<212> TYPE: DNA
<213> ORGANISM: Artificial Sequence
<220> FEATURE:
<223> OTHER INFORMATION: Barcoding sequence

<400> SEQUENCE: 809 gacacgaac                                                              9

<210> SEQ ID NO 810
<211> LENGTH: 9
<212> TYPE: DNA
<213> ORGANISM: Artificial Sequence
<220> FEATURE:
<223> OTHER INFORMATION: Barcoding sequence

<400> SEQUENCE: 810 agcacgaac                                                              9

<210> SEQ ID NO 811
<211> LENGTH: 9
<212> TYPE: DNA
<213> ORGANISM: Artificial Sequence
<220> FEATURE:
<223> OTHER INFORMATION: Barcoding sequence

<400> SEQUENCE: 811 tccacgaac                                                              9

<210> SEQ ID NO 812
<211> LENGTH: 9
<212> TYPE: DNA
<213> ORGANISM: Artificial Sequence
<220> FEATURE:
<223> OTHER INFORMATION: Barcoding sequence

<400> SEQUENCE: 812 ctcacgaac                                                              9

<210> SEQ ID NO 813
<211> LENGTH: 9
<212> TYPE: DNA
<213> ORGANISM: Artificial Sequence
<220> FEATURE:
<223> OTHER INFORMATION: Barcoding sequence

<400> SEQUENCE: 813 ggtacgaac                                                              9

<210> SEQ ID NO 814
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 814 cctacgaac                                                                 9

<210> SEQ ID NO 815
<211> LENGTH: 9
<212> TYPE: DNA
<213> ORGANISM: Artificial Sequence
<220> FEATURE:
<223> OTHER INFORMATION: Barcoding sequence

<400> SEQUENCE: 815 gaagcgaac                                                                 9

<210> SEQ ID NO 816
<211> LENGTH: 9
<212> TYPE: DNA
<213> ORGANISM: Artificial Sequence
<220> FEATURE:
<223> OTHER INFORMATION: Barcoding sequence

<400> SEQUENCE: 816 agagcgaac                                                                 9

<210> SEQ ID NO 817
<211> LENGTH: 9
<212> TYPE: DNA
<213> ORGANISM: Artificial Sequence
<220> FEATURE:
<223> OTHER INFORMATION: Barcoding sequence

<400> SEQUENCE: 817 tcagcgaac                                                                 9

<210> SEQ ID NO 818
<211> LENGTH: 9
<212> TYPE: DNA
<213> ORGANISM: Artificial Sequence
<220> FEATURE:
<223> OTHER INFORMATION: Barcoding sequence

<400> SEQUENCE: 818 ctagcgaac                                                                 9

<210> SEQ ID NO 819
<211> LENGTH: 9
<212> TYPE: DNA
<213> ORGANISM: Artificial Sequence
<220> FEATURE:
<223> OTHER INFORMATION: Barcoding sequence

<400> SEQUENCE: 819 aaggcgaac                                                                 9

<210> SEQ ID NO 820
<211> LENGTH: 9
<212> TYPE: DNA
<213> ORGANISM: Artificial Sequence
<220> FEATURE:
<223> OTHER INFORMATION: Barcoding sequence

<400> SEQUENCE: 820
``` ttggcgaac                                                                    9

<210> SEQ ID NO 821
<211> LENGTH: 9
<212> TYPE: DNA
<213> ORGANISM: Artificial Sequence
<220> FEATURE:
<223> OTHER INFORMATION: Barcoding sequence

<400> SEQUENCE: 821 tacgcgaac                                                                    9

<210> SEQ ID NO 822
<211> LENGTH: 9
<212> TYPE: DNA
<213> ORGANISM: Artificial Sequence
<220> FEATURE:
<223> OTHER INFORMATION: Barcoding sequence

<400> SEQUENCE: 822 atcgcgaac                                                                    9

<210> SEQ ID NO 823
<211> LENGTH: 9
<212> TYPE: DNA
<213> ORGANISM: Artificial Sequence
<220> FEATURE:
<223> OTHER INFORMATION: Barcoding sequence

<400> SEQUENCE: 823 catgcgaac                                                                    9

<210> SEQ ID NO 824
<211> LENGTH: 9
<212> TYPE: DNA
<213> ORGANISM: Artificial Sequence
<220> FEATURE:
<223> OTHER INFORMATION: Barcoding sequence

<400> SEQUENCE: 824 tgtgcgaac                                                                    9

<210> SEQ ID NO 825
<211> LENGTH: 9
<212> TYPE: DNA
<213> ORGANISM: Artificial Sequence
<220> FEATURE:
<223> OTHER INFORMATION: Barcoding sequence

<400> SEQUENCE: 825 actgcgaac                                                                    9

<210> SEQ ID NO 826
<211> LENGTH: 9
<212> TYPE: DNA
<213> ORGANISM: Artificial Sequence
<220> FEATURE:
<223> OTHER INFORMATION: Barcoding sequence

<400> SEQUENCE: 826 gttgcgaac                                                                    9

<210> SEQ ID NO 827
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 827 caaccgaac                                                                  9

<210> SEQ ID NO 828
<211> LENGTH: 9
<212> TYPE: DNA
<213> ORGANISM: Artificial Sequence
<220> FEATURE:
<223> OTHER INFORMATION: Barcoding sequence

<400> SEQUENCE: 828 tgaccgaac                                                                  9

<210> SEQ ID NO 829
<211> LENGTH: 9
<212> TYPE: DNA
<213> ORGANISM: Artificial Sequence
<220> FEATURE:
<223> OTHER INFORMATION: Barcoding sequence

<400> SEQUENCE: 829 acaccgaac                                                                  9

<210> SEQ ID NO 830
<211> LENGTH: 9
<212> TYPE: DNA
<213> ORGANISM: Artificial Sequence
<220> FEATURE:
<223> OTHER INFORMATION: Barcoding sequence

<400> SEQUENCE: 830 gtaccgaac                                                                  9

<210> SEQ ID NO 831
<211> LENGTH: 9
<212> TYPE: DNA
<213> ORGANISM: Artificial Sequence
<220> FEATURE:
<223> OTHER INFORMATION: Barcoding sequence

<400> SEQUENCE: 831 tagccgaac                                                                  9

<210> SEQ ID NO 832
<211> LENGTH: 9
<212> TYPE: DNA
<213> ORGANISM: Artificial Sequence
<220> FEATURE:
<223> OTHER INFORMATION: Barcoding sequence

<400> SEQUENCE: 832 atgccgaac                                                                  9

<210> SEQ ID NO 833
<211> LENGTH: 9
<212> TYPE: DNA
<213> ORGANISM: Artificial Sequence
<220> FEATURE:
<223> OTHER INFORMATION: Barcoding sequence

<400> SEQUENCE: 833 gatccgaac                                                                  9
```

```
<210> SEQ ID NO 834
<211> LENGTH: 9
<212> TYPE: DNA
<213> ORGANISM: Artificial Sequence
<220> FEATURE:
<223> OTHER INFORMATION: Barcoding sequence

<400> SEQUENCE: 834 agtccgaac                                                                  9

<210> SEQ ID NO 835
<211> LENGTH: 9
<212> TYPE: DNA
<213> ORGANISM: Artificial Sequence
<220> FEATURE:
<223> OTHER INFORMATION: Barcoding sequence

<400> SEQUENCE: 835 tctccgaac                                                                  9

<210> SEQ ID NO 836
<211> LENGTH: 9
<212> TYPE: DNA
<213> ORGANISM: Artificial Sequence
<220> FEATURE:
<223> OTHER INFORMATION: Barcoding sequence

<400> SEQUENCE: 836 cttccgaac                                                                  9

<210> SEQ ID NO 837
<211> LENGTH: 9
<212> TYPE: DNA
<213> ORGANISM: Artificial Sequence
<220> FEATURE:
<223> OTHER INFORMATION: Barcoding sequence

<400> SEQUENCE: 837 ggatcgaac                                                                  9

<210> SEQ ID NO 838
<211> LENGTH: 9
<212> TYPE: DNA
<213> ORGANISM: Artificial Sequence
<220> FEATURE:
<223> OTHER INFORMATION: Barcoding sequence

<400> SEQUENCE: 838 ccatcgaac                                                                  9

<210> SEQ ID NO 839
<211> LENGTH: 9
<212> TYPE: DNA
<213> ORGANISM: Artificial Sequence
<220> FEATURE:
<223> OTHER INFORMATION: Barcoding sequence

<400> SEQUENCE: 839 gagtcgaac                                                                  9

<210> SEQ ID NO 840
<211> LENGTH: 9
<212> TYPE: DNA
<213> ORGANISM: Artificial Sequence
<220> FEATURE:
```

```
<223> OTHER INFORMATION: Barcoding sequence

<400> SEQUENCE: 840 aggtcgaac                                                              9

<210> SEQ ID NO 841
<211> LENGTH: 9
<212> TYPE: DNA
<213> ORGANISM: Artificial Sequence
<220> FEATURE:
<223> OTHER INFORMATION: Barcoding sequence

<400> SEQUENCE: 841 tcgtcgaac                                                              9

<210> SEQ ID NO 842
<211> LENGTH: 9
<212> TYPE: DNA
<213> ORGANISM: Artificial Sequence
<220> FEATURE:
<223> OTHER INFORMATION: Barcoding sequence

<400> SEQUENCE: 842 ctgtcgaac                                                              9

<210> SEQ ID NO 843
<211> LENGTH: 9
<212> TYPE: DNA
<213> ORGANISM: Artificial Sequence
<220> FEATURE:
<223> OTHER INFORMATION: Barcoding sequence

<400> SEQUENCE: 843 cactcgaac                                                              9

<210> SEQ ID NO 844
<211> LENGTH: 9
<212> TYPE: DNA
<213> ORGANISM: Artificial Sequence
<220> FEATURE:
<223> OTHER INFORMATION: Barcoding sequence

<400> SEQUENCE: 844 tgctcgaac                                                              9

<210> SEQ ID NO 845
<211> LENGTH: 9
<212> TYPE: DNA
<213> ORGANISM: Artificial Sequence
<220> FEATURE:
<223> OTHER INFORMATION: Barcoding sequence

<400> SEQUENCE: 845 acctcgaac                                                              9

<210> SEQ ID NO 846
<211> LENGTH: 9
<212> TYPE: DNA
<213> ORGANISM: Artificial Sequence
<220> FEATURE:
<223> OTHER INFORMATION: Barcoding sequence

<400> SEQUENCE: 846 gtctcgaac                                                              9
```

```
<210> SEQ ID NO 847
<211> LENGTH: 9
<212> TYPE: DNA
<213> ORGANISM: Artificial Sequence
<220> FEATURE:
<223> OTHER INFORMATION: Barcoding sequence

<400> SEQUENCE: 847 cgttcgaac                                                                  9

<210> SEQ ID NO 848
<211> LENGTH: 9
<212> TYPE: DNA
<213> ORGANISM: Artificial Sequence
<220> FEATURE:
<223> OTHER INFORMATION: Barcoding sequence

<400> SEQUENCE: 848 gcttcgaac                                                                  9

<210> SEQ ID NO 849
<211> LENGTH: 9
<212> TYPE: DNA
<213> ORGANISM: Artificial Sequence
<220> FEATURE:
<223> OTHER INFORMATION: Barcoding sequence

<400> SEQUENCE: 849 ccgatgaac                                                                  9

<210> SEQ ID NO 850
<211> LENGTH: 9
<212> TYPE: DNA
<213> ORGANISM: Artificial Sequence
<220> FEATURE:
<223> OTHER INFORMATION: Barcoding sequence

<400> SEQUENCE: 850 cgcatgaac                                                                  9

<210> SEQ ID NO 851
<211> LENGTH: 9
<212> TYPE: DNA
<213> ORGANISM: Artificial Sequence
<220> FEATURE:
<223> OTHER INFORMATION: Barcoding sequence

<400> SEQUENCE: 851 gccatgaac                                                                  9

<210> SEQ ID NO 852
<211> LENGTH: 9
<212> TYPE: DNA
<213> ORGANISM: Artificial Sequence
<220> FEATURE:
<223> OTHER INFORMATION: Barcoding sequence

<400> SEQUENCE: 852 cgagtgaac                                                                  9

<210> SEQ ID NO 853
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 853 gcagtgaac                                                            9

<210> SEQ ID NO 854
<211> LENGTH: 9
<212> TYPE: DNA
<213> ORGANISM: Artificial Sequence
<220> FEATURE:
<223> OTHER INFORMATION: Barcoding sequence

<400> SEQUENCE: 854 caggtgaac                                                            9

<210> SEQ ID NO 855
<211> LENGTH: 9
<212> TYPE: DNA
<213> ORGANISM: Artificial Sequence
<220> FEATURE:
<223> OTHER INFORMATION: Barcoding sequence

<400> SEQUENCE: 855 tcggtgaac                                                            9

<210> SEQ ID NO 856
<211> LENGTH: 9
<212> TYPE: DNA
<213> ORGANISM: Artificial Sequence
<220> FEATURE:
<223> OTHER INFORMATION: Barcoding sequence

<400> SEQUENCE: 856 gtggtgaac                                                            9

<210> SEQ ID NO 857
<211> LENGTH: 9
<212> TYPE: DNA
<213> ORGANISM: Artificial Sequence
<220> FEATURE:
<223> OTHER INFORMATION: Barcoding sequence

<400> SEQUENCE: 857 gacgtgaac                                                            9

<210> SEQ ID NO 858
<211> LENGTH: 9
<212> TYPE: DNA
<213> ORGANISM: Artificial Sequence
<220> FEATURE:
<223> OTHER INFORMATION: Barcoding sequence

<400> SEQUENCE: 858 tgcgtgaac                                                            9

<210> SEQ ID NO 859
<211> LENGTH: 9
<212> TYPE: DNA
<213> ORGANISM: Artificial Sequence
<220> FEATURE:
<223> OTHER INFORMATION: Barcoding sequence

<400> SEQUENCE: 859 accgtgaac                                                            9

<210> SEQ ID NO 860
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 860 ctcgtgaac                                                               9

<210> SEQ ID NO 861
<211> LENGTH: 9
<212> TYPE: DNA
<213> ORGANISM: Artificial Sequence
<220> FEATURE:
<223> OTHER INFORMATION: Barcoding sequence

<400> SEQUENCE: 861 ggtgtgaac                                                               9

<210> SEQ ID NO 862
<211> LENGTH: 9
<212> TYPE: DNA
<213> ORGANISM: Artificial Sequence
<220> FEATURE:
<223> OTHER INFORMATION: Barcoding sequence

<400> SEQUENCE: 862 cctgtgaac                                                               9

<210> SEQ ID NO 863
<211> LENGTH: 9
<212> TYPE: DNA
<213> ORGANISM: Artificial Sequence
<220> FEATURE:
<223> OTHER INFORMATION: Barcoding sequence

<400> SEQUENCE: 863 ggactgaac                                                               9

<210> SEQ ID NO 864
<211> LENGTH: 9
<212> TYPE: DNA
<213> ORGANISM: Artificial Sequence
<220> FEATURE:
<223> OTHER INFORMATION: Barcoding sequence

<400> SEQUENCE: 864 ccactgaac                                                               9

<210> SEQ ID NO 865
<211> LENGTH: 9
<212> TYPE: DNA
<213> ORGANISM: Artificial Sequence
<220> FEATURE:
<223> OTHER INFORMATION: Barcoding sequence

<400> SEQUENCE: 865 gagctgaac                                                               9

<210> SEQ ID NO 866
<211> LENGTH: 9
<212> TYPE: DNA
<213> ORGANISM: Artificial Sequence
<220> FEATURE:
<223> OTHER INFORMATION: Barcoding sequence

<400> SEQUENCE: 866
``` tggctgaac                                                                          9

<210> SEQ ID NO 867
<211> LENGTH: 9
<212> TYPE: DNA
<213> ORGANISM: Artificial Sequence
<220> FEATURE:
<223> OTHER INFORMATION: Barcoding sequence

<400> SEQUENCE: 867 acgctgaac                                                                          9

<210> SEQ ID NO 868
<211> LENGTH: 9
<212> TYPE: DNA
<213> ORGANISM: Artificial Sequence
<220> FEATURE:
<223> OTHER INFORMATION: Barcoding sequence

<400> SEQUENCE: 868 ctgctgaac                                                                          9

<210> SEQ ID NO 869
<211> LENGTH: 9
<212> TYPE: DNA
<213> ORGANISM: Artificial Sequence
<220> FEATURE:
<223> OTHER INFORMATION: Barcoding sequence

<400> SEQUENCE: 869 cacctgaac                                                                          9

<210> SEQ ID NO 870
<211> LENGTH: 9
<212> TYPE: DNA
<213> ORGANISM: Artificial Sequence
<220> FEATURE:
<223> OTHER INFORMATION: Barcoding sequence

<400> SEQUENCE: 870 agcctgaac                                                                          9

<210> SEQ ID NO 871
<211> LENGTH: 9
<212> TYPE: DNA
<213> ORGANISM: Artificial Sequence
<220> FEATURE:
<223> OTHER INFORMATION: Barcoding sequence

<400> SEQUENCE: 871 gtcctgaac                                                                          9

<210> SEQ ID NO 872
<211> LENGTH: 9
<212> TYPE: DNA
<213> ORGANISM: Artificial Sequence
<220> FEATURE:
<223> OTHER INFORMATION: Barcoding sequence

<400> SEQUENCE: 872 cgtctgaac                                                                          9

<210> SEQ ID NO 873
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 873 gctctgaac                                                                      9

<210> SEQ ID NO 874
<211> LENGTH: 9
<212> TYPE: DNA
<213> ORGANISM: Artificial Sequence
<220> FEATURE:
<223> OTHER INFORMATION: Barcoding sequence

<400> SEQUENCE: 874 cggttgaac                                                                      9

<210> SEQ ID NO 875
<211> LENGTH: 9
<212> TYPE: DNA
<213> ORGANISM: Artificial Sequence
<220> FEATURE:
<223> OTHER INFORMATION: Barcoding sequence

<400> SEQUENCE: 875 gcgttgaac                                                                      9

<210> SEQ ID NO 876
<211> LENGTH: 9
<212> TYPE: DNA
<213> ORGANISM: Artificial Sequence
<220> FEATURE:
<223> OTHER INFORMATION: Barcoding sequence

<400> SEQUENCE: 876 ggcttgaac                                                                      9

<210> SEQ ID NO 877
<211> LENGTH: 9
<212> TYPE: DNA
<213> ORGANISM: Artificial Sequence
<220> FEATURE:
<223> OTHER INFORMATION: Barcoding sequence

<400> SEQUENCE: 877 ccgaacaac                                                                      9

<210> SEQ ID NO 878
<211> LENGTH: 9
<212> TYPE: DNA
<213> ORGANISM: Artificial Sequence
<220> FEATURE:
<223> OTHER INFORMATION: Barcoding sequence

<400> SEQUENCE: 878 cgcaacaac                                                                      9

<210> SEQ ID NO 879
<211> LENGTH: 9
<212> TYPE: DNA
<213> ORGANISM: Artificial Sequence
<220> FEATURE:
<223> OTHER INFORMATION: Barcoding sequence

<400> SEQUENCE: 879 gccaacaac                                                                      9
```

```
<210> SEQ ID NO 880
<211> LENGTH: 9
<212> TYPE: DNA
<213> ORGANISM: Artificial Sequence
<220> FEATURE:
<223> OTHER INFORMATION: Barcoding sequence

<400> SEQUENCE: 880 cgagacaac                                                                 9

<210> SEQ ID NO 881
<211> LENGTH: 9
<212> TYPE: DNA
<213> ORGANISM: Artificial Sequence
<220> FEATURE:
<223> OTHER INFORMATION: Barcoding sequence

<400> SEQUENCE: 881 gcagacaac                                                                 9

<210> SEQ ID NO 882
<211> LENGTH: 9
<212> TYPE: DNA
<213> ORGANISM: Artificial Sequence
<220> FEATURE:
<223> OTHER INFORMATION: Barcoding sequence

<400> SEQUENCE: 882 caggacaac                                                                 9

<210> SEQ ID NO 883
<211> LENGTH: 9
<212> TYPE: DNA
<213> ORGANISM: Artificial Sequence
<220> FEATURE:
<223> OTHER INFORMATION: Barcoding sequence

<400> SEQUENCE: 883 tcggacaac                                                                 9

<210> SEQ ID NO 884
<211> LENGTH: 9
<212> TYPE: DNA
<213> ORGANISM: Artificial Sequence
<220> FEATURE:
<223> OTHER INFORMATION: Barcoding sequence

<400> SEQUENCE: 884 gtggacaac                                                                 9

<210> SEQ ID NO 885
<211> LENGTH: 9
<212> TYPE: DNA
<213> ORGANISM: Artificial Sequence
<220> FEATURE:
<223> OTHER INFORMATION: Barcoding sequence

<400> SEQUENCE: 885 gacgacaac                                                                 9

<210> SEQ ID NO 886
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 886 tgcgacaac                                                          9

<210> SEQ ID NO 887
<211> LENGTH: 9
<212> TYPE: DNA
<213> ORGANISM: Artificial Sequence
<220> FEATURE:
<223> OTHER INFORMATION: Barcoding sequence

<400> SEQUENCE: 887 accgacaac                                                          9

<210> SEQ ID NO 888
<211> LENGTH: 9
<212> TYPE: DNA
<213> ORGANISM: Artificial Sequence
<220> FEATURE:
<223> OTHER INFORMATION: Barcoding sequence

<400> SEQUENCE: 888 ctcgacaac                                                          9

<210> SEQ ID NO 889
<211> LENGTH: 9
<212> TYPE: DNA
<213> ORGANISM: Artificial Sequence
<220> FEATURE:
<223> OTHER INFORMATION: Barcoding sequence

<400> SEQUENCE: 889 ggtgacaac                                                          9

<210> SEQ ID NO 890
<211> LENGTH: 9
<212> TYPE: DNA
<213> ORGANISM: Artificial Sequence
<220> FEATURE:
<223> OTHER INFORMATION: Barcoding sequence

<400> SEQUENCE: 890 cctgacaac                                                          9

<210> SEQ ID NO 891
<211> LENGTH: 9
<212> TYPE: DNA
<213> ORGANISM: Artificial Sequence
<220> FEATURE:
<223> OTHER INFORMATION: Barcoding sequence

<400> SEQUENCE: 891 ggacacaac                                                          9

<210> SEQ ID NO 892
<211> LENGTH: 9
<212> TYPE: DNA
<213> ORGANISM: Artificial Sequence
<220> FEATURE:
<223> OTHER INFORMATION: Barcoding sequence

<400> SEQUENCE: 892 ccacacaac                                                          9

<210> SEQ ID NO 893
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 893 gagcacaac                                                                9

<210> SEQ ID NO 894
<211> LENGTH: 9
<212> TYPE: DNA
<213> ORGANISM: Artificial Sequence
<220> FEATURE:
<223> OTHER INFORMATION: Barcoding sequence

<400> SEQUENCE: 894 tggcacaac                                                                9

<210> SEQ ID NO 895
<211> LENGTH: 9
<212> TYPE: DNA
<213> ORGANISM: Artificial Sequence
<220> FEATURE:
<223> OTHER INFORMATION: Barcoding sequence

<400> SEQUENCE: 895 acgcacaac                                                                9

<210> SEQ ID NO 896
<211> LENGTH: 9
<212> TYPE: DNA
<213> ORGANISM: Artificial Sequence
<220> FEATURE:
<223> OTHER INFORMATION: Barcoding sequence

<400> SEQUENCE: 896 ctgcacaac                                                                9

<210> SEQ ID NO 897
<211> LENGTH: 9
<212> TYPE: DNA
<213> ORGANISM: Artificial Sequence
<220> FEATURE:
<223> OTHER INFORMATION: Barcoding sequence

<400> SEQUENCE: 897 caccacaac                                                                9

<210> SEQ ID NO 898
<211> LENGTH: 9
<212> TYPE: DNA
<213> ORGANISM: Artificial Sequence
<220> FEATURE:
<223> OTHER INFORMATION: Barcoding sequence

<400> SEQUENCE: 898 agccacaac                                                                9

<210> SEQ ID NO 899
<211> LENGTH: 9
<212> TYPE: DNA
<213> ORGANISM: Artificial Sequence
<220> FEATURE:
<223> OTHER INFORMATION: Barcoding sequence

<400> SEQUENCE: 899
``` gtccacaac                                                                9

<210> SEQ ID NO 900
<211> LENGTH: 9
<212> TYPE: DNA
<213> ORGANISM: Artificial Sequence
<220> FEATURE:
<223> OTHER INFORMATION: Barcoding sequence

<400> SEQUENCE: 900 cgtcacaac                                                                9

<210> SEQ ID NO 901
<211> LENGTH: 9
<212> TYPE: DNA
<213> ORGANISM: Artificial Sequence
<220> FEATURE:
<223> OTHER INFORMATION: Barcoding sequence

<400> SEQUENCE: 901 gctcacaac                                                                9

<210> SEQ ID NO 902
<211> LENGTH: 9
<212> TYPE: DNA
<213> ORGANISM: Artificial Sequence
<220> FEATURE:
<223> OTHER INFORMATION: Barcoding sequence

<400> SEQUENCE: 902 cggtacaac                                                                9

<210> SEQ ID NO 903
<211> LENGTH: 9
<212> TYPE: DNA
<213> ORGANISM: Artificial Sequence
<220> FEATURE:
<223> OTHER INFORMATION: Barcoding sequence

<400> SEQUENCE: 903 gcgtacaac                                                                9

<210> SEQ ID NO 904
<211> LENGTH: 9
<212> TYPE: DNA
<213> ORGANISM: Artificial Sequence
<220> FEATURE:
<223> OTHER INFORMATION: Barcoding sequence

<400> SEQUENCE: 904 ggctacaac                                                                9

<210> SEQ ID NO 905
<211> LENGTH: 9
<212> TYPE: DNA
<213> ORGANISM: Artificial Sequence
<220> FEATURE:
<223> OTHER INFORMATION: Barcoding sequence

<400> SEQUENCE: 905 cgaagcaac                                                                9

<210> SEQ ID NO 906
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 906 gcaagcaac                                                                9

<210> SEQ ID NO 907
<211> LENGTH: 9
<212> TYPE: DNA
<213> ORGANISM: Artificial Sequence
<220> FEATURE:
<223> OTHER INFORMATION: Barcoding sequence

<400> SEQUENCE: 907 cagagcaac                                                                9

<210> SEQ ID NO 908
<211> LENGTH: 9
<212> TYPE: DNA
<213> ORGANISM: Artificial Sequence
<220> FEATURE:
<223> OTHER INFORMATION: Barcoding sequence

<400> SEQUENCE: 908 tggagcaac                                                                9

<210> SEQ ID NO 909
<211> LENGTH: 9
<212> TYPE: DNA
<213> ORGANISM: Artificial Sequence
<220> FEATURE:
<223> OTHER INFORMATION: Barcoding sequence

<400> SEQUENCE: 909 acgagcaac                                                                9

<210> SEQ ID NO 910
<211> LENGTH: 9
<212> TYPE: DNA
<213> ORGANISM: Artificial Sequence
<220> FEATURE:
<223> OTHER INFORMATION: Barcoding sequence

<400> SEQUENCE: 910 gtgagcaac                                                                9

<210> SEQ ID NO 911
<211> LENGTH: 9
<212> TYPE: DNA
<213> ORGANISM: Artificial Sequence
<220> FEATURE:
<223> OTHER INFORMATION: Barcoding sequence

<400> SEQUENCE: 911 gacagcaac                                                                9

<210> SEQ ID NO 912
<211> LENGTH: 9
<212> TYPE: DNA
<213> ORGANISM: Artificial Sequence
<220> FEATURE:
<223> OTHER INFORMATION: Barcoding sequence

<400> SEQUENCE: 912 agcagcaac                                                                9
```

```
<210> SEQ ID NO 913
<211> LENGTH: 9
<212> TYPE: DNA
<213> ORGANISM: Artificial Sequence
<220> FEATURE:
<223> OTHER INFORMATION: Barcoding sequence

<400> SEQUENCE: 913 tccagcaac                                                                 9

<210> SEQ ID NO 914
<211> LENGTH: 9
<212> TYPE: DNA
<213> ORGANISM: Artificial Sequence
<220> FEATURE:
<223> OTHER INFORMATION: Barcoding sequence

<400> SEQUENCE: 914 ctcagcaac                                                                 9

<210> SEQ ID NO 915
<211> LENGTH: 9
<212> TYPE: DNA
<213> ORGANISM: Artificial Sequence
<220> FEATURE:
<223> OTHER INFORMATION: Barcoding sequence

<400> SEQUENCE: 915 ggtagcaac                                                                 9

<210> SEQ ID NO 916
<211> LENGTH: 9
<212> TYPE: DNA
<213> ORGANISM: Artificial Sequence
<220> FEATURE:
<223> OTHER INFORMATION: Barcoding sequence

<400> SEQUENCE: 916 cctagcaac                                                                 9

<210> SEQ ID NO 917
<211> LENGTH: 9
<212> TYPE: DNA
<213> ORGANISM: Artificial Sequence
<220> FEATURE:
<223> OTHER INFORMATION: Barcoding sequence

<400> SEQUENCE: 917 gaaggcaac                                                                 9

<210> SEQ ID NO 918
<211> LENGTH: 9
<212> TYPE: DNA
<213> ORGANISM: Artificial Sequence
<220> FEATURE:
<223> OTHER INFORMATION: Barcoding sequence

<400> SEQUENCE: 918 agaggcaac                                                                 9

<210> SEQ ID NO 919
<211> LENGTH: 9
<212> TYPE: DNA
<213> ORGANISM: Artificial Sequence
<220> FEATURE:
```

```
<223> OTHER INFORMATION: Barcoding sequence

<400> SEQUENCE: 919 tcaggcaac                                                                9

<210> SEQ ID NO 920
<211> LENGTH: 9
<212> TYPE: DNA
<213> ORGANISM: Artificial Sequence
<220> FEATURE:
<223> OTHER INFORMATION: Barcoding sequence

<400> SEQUENCE: 920 ctaggcaac                                                                9

<210> SEQ ID NO 921
<211> LENGTH: 9
<212> TYPE: DNA
<213> ORGANISM: Artificial Sequence
<220> FEATURE:
<223> OTHER INFORMATION: Barcoding sequence

<400> SEQUENCE: 921 aacggcaac                                                                9

<210> SEQ ID NO 922
<211> LENGTH: 9
<212> TYPE: DNA
<213> ORGANISM: Artificial Sequence
<220> FEATURE:
<223> OTHER INFORMATION: Barcoding sequence

<400> SEQUENCE: 922 ttcggcaac                                                                9

<210> SEQ ID NO 923
<211> LENGTH: 9
<212> TYPE: DNA
<213> ORGANISM: Artificial Sequence
<220> FEATURE:
<223> OTHER INFORMATION: Barcoding sequence

<400> SEQUENCE: 923 catggcaac                                                                9

<210> SEQ ID NO 924
<211> LENGTH: 9
<212> TYPE: DNA
<213> ORGANISM: Artificial Sequence
<220> FEATURE:
<223> OTHER INFORMATION: Barcoding sequence

<400> SEQUENCE: 924 tgtggcaac                                                                9

<210> SEQ ID NO 925
<211> LENGTH: 9
<212> TYPE: DNA
<213> ORGANISM: Artificial Sequence
<220> FEATURE:
<223> OTHER INFORMATION: Barcoding sequence

<400> SEQUENCE: 925 actggcaac                                                                9
```

<210> SEQ ID NO 926
<211> LENGTH: 9
<212> TYPE: DNA
<213> ORGANISM: Artificial Sequence
<220> FEATURE:
<223> OTHER INFORMATION: Barcoding sequence

<400> SEQUENCE: 926 gttggcaac                                                                9

<210> SEQ ID NO 927
<211> LENGTH: 9
<212> TYPE: DNA
<213> ORGANISM: Artificial Sequence
<220> FEATURE:
<223> OTHER INFORMATION: Barcoding sequence

<400> SEQUENCE: 927 caacgcaac                                                                9

<210> SEQ ID NO 928
<211> LENGTH: 9
<212> TYPE: DNA
<213> ORGANISM: Artificial Sequence
<220> FEATURE:
<223> OTHER INFORMATION: Barcoding sequence

<400> SEQUENCE: 928 tgacgcaac                                                                9

<210> SEQ ID NO 929
<211> LENGTH: 9
<212> TYPE: DNA
<213> ORGANISM: Artificial Sequence
<220> FEATURE:
<223> OTHER INFORMATION: Barcoding sequence

<400> SEQUENCE: 929 acacgcaac                                                                9

<210> SEQ ID NO 930
<211> LENGTH: 9
<212> TYPE: DNA
<213> ORGANISM: Artificial Sequence
<220> FEATURE:
<223> OTHER INFORMATION: Barcoding sequence

<400> SEQUENCE: 930 gtacgcaac                                                                9

<210> SEQ ID NO 931
<211> LENGTH: 9
<212> TYPE: DNA
<213> ORGANISM: Artificial Sequence
<220> FEATURE:
<223> OTHER INFORMATION: Barcoding sequence

<400> SEQUENCE: 931 tagcgcaac                                                                9

<210> SEQ ID NO 932
<211> LENGTH: 9
<212> TYPE: DNA
<213> ORGANISM: Artificial Sequence
<220> FEATURE:
<223> OTHER INFORMATION: Barcoding sequence

```
<400> SEQUENCE: 932 atgcgcaac                                                              9

<210> SEQ ID NO 933
<211> LENGTH: 9
<212> TYPE: DNA
<213> ORGANISM: Artificial Sequence
<220> FEATURE:
<223> OTHER INFORMATION: Barcoding sequence

<400> SEQUENCE: 933 gatcgcaac                                                              9

<210> SEQ ID NO 934
<211> LENGTH: 9
<212> TYPE: DNA
<213> ORGANISM: Artificial Sequence
<220> FEATURE:
<223> OTHER INFORMATION: Barcoding sequence

<400> SEQUENCE: 934 agtcgcaac                                                              9

<210> SEQ ID NO 935
<211> LENGTH: 9
<212> TYPE: DNA
<213> ORGANISM: Artificial Sequence
<220> FEATURE:
<223> OTHER INFORMATION: Barcoding sequence

<400> SEQUENCE: 935 tctcgcaac                                                              9

<210> SEQ ID NO 936
<211> LENGTH: 9
<212> TYPE: DNA
<213> ORGANISM: Artificial Sequence
<220> FEATURE:
<223> OTHER INFORMATION: Barcoding sequence

<400> SEQUENCE: 936 cttcgcaac                                                              9

<210> SEQ ID NO 937
<211> LENGTH: 9
<212> TYPE: DNA
<213> ORGANISM: Artificial Sequence
<220> FEATURE:
<223> OTHER INFORMATION: Barcoding sequence

<400> SEQUENCE: 937 ggatgcaac                                                              9

<210> SEQ ID NO 938
<211> LENGTH: 9
<212> TYPE: DNA
<213> ORGANISM: Artificial Sequence
<220> FEATURE:
<223> OTHER INFORMATION: Barcoding sequence

<400> SEQUENCE: 938 ccatgcaac                                                              9

<210> SEQ ID NO 939
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 939 gagtgcaac                                                                 9

<210> SEQ ID NO 940
<211> LENGTH: 9
<212> TYPE: DNA
<213> ORGANISM: Artificial Sequence
<220> FEATURE:
<223> OTHER INFORMATION: Barcoding sequence

<400> SEQUENCE: 940 aggtgcaac                                                                 9

<210> SEQ ID NO 941
<211> LENGTH: 9
<212> TYPE: DNA
<213> ORGANISM: Artificial Sequence
<220> FEATURE:
<223> OTHER INFORMATION: Barcoding sequence

<400> SEQUENCE: 941 tcgtgcaac                                                                 9

<210> SEQ ID NO 942
<211> LENGTH: 9
<212> TYPE: DNA
<213> ORGANISM: Artificial Sequence
<220> FEATURE:
<223> OTHER INFORMATION: Barcoding sequence

<400> SEQUENCE: 942 ctgtgcaac                                                                 9

<210> SEQ ID NO 943
<211> LENGTH: 9
<212> TYPE: DNA
<213> ORGANISM: Artificial Sequence
<220> FEATURE:
<223> OTHER INFORMATION: Barcoding sequence

<400> SEQUENCE: 943 cactgcaac                                                                 9

<210> SEQ ID NO 944
<211> LENGTH: 9
<212> TYPE: DNA
<213> ORGANISM: Artificial Sequence
<220> FEATURE:
<223> OTHER INFORMATION: Barcoding sequence

<400> SEQUENCE: 944 tgctgcaac                                                                 9

<210> SEQ ID NO 945
<211> LENGTH: 9
<212> TYPE: DNA
<213> ORGANISM: Artificial Sequence
<220> FEATURE:
<223> OTHER INFORMATION: Barcoding sequence

<400> SEQUENCE: 945
``` acctgcaac 9

<210> SEQ ID NO 946
<211> LENGTH: 9
<212> TYPE: DNA
<213> ORGANISM: Artificial Sequence
<220> FEATURE:
<223> OTHER INFORMATION: Barcoding sequence

<400> SEQUENCE: 946 gtctgcaac 9

<210> SEQ ID NO 947
<211> LENGTH: 9
<212> TYPE: DNA
<213> ORGANISM: Artificial Sequence
<220> FEATURE:
<223> OTHER INFORMATION: Barcoding sequence

<400> SEQUENCE: 947 cgttgcaac 9

<210> SEQ ID NO 948
<211> LENGTH: 9
<212> TYPE: DNA
<213> ORGANISM: Artificial Sequence
<220> FEATURE:
<223> OTHER INFORMATION: Barcoding sequence

<400> SEQUENCE: 948 gcttgcaac 9

<210> SEQ ID NO 949
<211> LENGTH: 9
<212> TYPE: DNA
<213> ORGANISM: Artificial Sequence
<220> FEATURE:
<223> OTHER INFORMATION: Barcoding sequence

<400> SEQUENCE: 949 ggaaccaac 9

<210> SEQ ID NO 950
<211> LENGTH: 9
<212> TYPE: DNA
<213> ORGANISM: Artificial Sequence
<220> FEATURE:
<223> OTHER INFORMATION: Barcoding sequence

<400> SEQUENCE: 950 ccaaccaac 9

<210> SEQ ID NO 951
<211> LENGTH: 9
<212> TYPE: DNA
<213> ORGANISM: Artificial Sequence
<220> FEATURE:
<223> OTHER INFORMATION: Barcoding sequence

<400> SEQUENCE: 951 gagaccaac 9

<210> SEQ ID NO 952
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 952 aggaccaac                                                                9

<210> SEQ ID NO 953
<211> LENGTH: 9
<212> TYPE: DNA
<213> ORGANISM: Artificial Sequence
<220> FEATURE:
<223> OTHER INFORMATION: Barcoding sequence

<400> SEQUENCE: 953 tcgaccaac                                                                9

<210> SEQ ID NO 954
<211> LENGTH: 9
<212> TYPE: DNA
<213> ORGANISM: Artificial Sequence
<220> FEATURE:
<223> OTHER INFORMATION: Barcoding sequence

<400> SEQUENCE: 954 ctgaccaac                                                                9

<210> SEQ ID NO 955
<211> LENGTH: 9
<212> TYPE: DNA
<213> ORGANISM: Artificial Sequence
<220> FEATURE:
<223> OTHER INFORMATION: Barcoding sequence

<400> SEQUENCE: 955 cacaccaac                                                                9

<210> SEQ ID NO 956
<211> LENGTH: 9
<212> TYPE: DNA
<213> ORGANISM: Artificial Sequence
<220> FEATURE:
<223> OTHER INFORMATION: Barcoding sequence

<400> SEQUENCE: 956 tgcaccaac                                                                9

<210> SEQ ID NO 957
<211> LENGTH: 9
<212> TYPE: DNA
<213> ORGANISM: Artificial Sequence
<220> FEATURE:
<223> OTHER INFORMATION: Barcoding sequence

<400> SEQUENCE: 957 accaccaac                                                                9

<210> SEQ ID NO 958
<211> LENGTH: 9
<212> TYPE: DNA
<213> ORGANISM: Artificial Sequence
<220> FEATURE:
<223> OTHER INFORMATION: Barcoding sequence

<400> SEQUENCE: 958 gtcaccaac                                                                9
```

```
<210> SEQ ID NO 959
<211> LENGTH: 9
<212> TYPE: DNA
<213> ORGANISM: Artificial Sequence
<220> FEATURE:
<223> OTHER INFORMATION: Barcoding sequence

<400> SEQUENCE: 959 cgtaccaac                                                                 9

<210> SEQ ID NO 960
<211> LENGTH: 9
<212> TYPE: DNA
<213> ORGANISM: Artificial Sequence
<220> FEATURE:
<223> OTHER INFORMATION: Barcoding sequence

<400> SEQUENCE: 960 gctaccaac                                                                 9

<210> SEQ ID NO 961
<211> LENGTH: 9
<212> TYPE: DNA
<213> ORGANISM: Artificial Sequence
<220> FEATURE:
<223> OTHER INFORMATION: Barcoding sequence

<400> SEQUENCE: 961 caagccaac                                                                 9

<210> SEQ ID NO 962
<211> LENGTH: 9
<212> TYPE: DNA
<213> ORGANISM: Artificial Sequence
<220> FEATURE:
<223> OTHER INFORMATION: Barcoding sequence

<400> SEQUENCE: 962 tgagccaac                                                                 9

<210> SEQ ID NO 963
<211> LENGTH: 9
<212> TYPE: DNA
<213> ORGANISM: Artificial Sequence
<220> FEATURE:
<223> OTHER INFORMATION: Barcoding sequence

<400> SEQUENCE: 963 acagccaac                                                                 9

<210> SEQ ID NO 964
<211> LENGTH: 9
<212> TYPE: DNA
<213> ORGANISM: Artificial Sequence
<220> FEATURE:
<223> OTHER INFORMATION: Barcoding sequence

<400> SEQUENCE: 964 gtagccaac                                                                 9

<210> SEQ ID NO 965
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 965 taggccaac                                                          9

<210> SEQ ID NO 966
<211> LENGTH: 9
<212> TYPE: DNA
<213> ORGANISM: Artificial Sequence
<220> FEATURE:
<223> OTHER INFORMATION: Barcoding sequence

<400> SEQUENCE: 966 atggccaac                                                          9

<210> SEQ ID NO 967
<211> LENGTH: 9
<212> TYPE: DNA
<213> ORGANISM: Artificial Sequence
<220> FEATURE:
<223> OTHER INFORMATION: Barcoding sequence

<400> SEQUENCE: 967 gatgccaac                                                          9

<210> SEQ ID NO 968
<211> LENGTH: 9
<212> TYPE: DNA
<213> ORGANISM: Artificial Sequence
<220> FEATURE:
<223> OTHER INFORMATION: Barcoding sequence

<400> SEQUENCE: 968 agtgccaac                                                          9

<210> SEQ ID NO 969
<211> LENGTH: 9
<212> TYPE: DNA
<213> ORGANISM: Artificial Sequence
<220> FEATURE:
<223> OTHER INFORMATION: Barcoding sequence

<400> SEQUENCE: 969 tctgccaac                                                          9

<210> SEQ ID NO 970
<211> LENGTH: 9
<212> TYPE: DNA
<213> ORGANISM: Artificial Sequence
<220> FEATURE:
<223> OTHER INFORMATION: Barcoding sequence

<400> SEQUENCE: 970 cttgccaac                                                          9

<210> SEQ ID NO 971
<211> LENGTH: 9
<212> TYPE: DNA
<213> ORGANISM: Artificial Sequence
<220> FEATURE:
<223> OTHER INFORMATION: Barcoding sequence

<400> SEQUENCE: 971 cgatccaac                                                          9

<210> SEQ ID NO 972
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 972 gcatccaac                                                                 9

<210> SEQ ID NO 973
<211> LENGTH: 9
<212> TYPE: DNA
<213> ORGANISM: Artificial Sequence
<220> FEATURE:
<223> OTHER INFORMATION: Barcoding sequence

<400> SEQUENCE: 973 cagtccaac                                                                 9

<210> SEQ ID NO 974
<211> LENGTH: 9
<212> TYPE: DNA
<213> ORGANISM: Artificial Sequence
<220> FEATURE:
<223> OTHER INFORMATION: Barcoding sequence

<400> SEQUENCE: 974 tggtccaac                                                                 9

<210> SEQ ID NO 975
<211> LENGTH: 9
<212> TYPE: DNA
<213> ORGANISM: Artificial Sequence
<220> FEATURE:
<223> OTHER INFORMATION: Barcoding sequence

<400> SEQUENCE: 975 acgtccaac                                                                 9

<210> SEQ ID NO 976
<211> LENGTH: 9
<212> TYPE: DNA
<213> ORGANISM: Artificial Sequence
<220> FEATURE:
<223> OTHER INFORMATION: Barcoding sequence

<400> SEQUENCE: 976 gtgtccaac                                                                 9

<210> SEQ ID NO 977
<211> LENGTH: 9
<212> TYPE: DNA
<213> ORGANISM: Artificial Sequence
<220> FEATURE:
<223> OTHER INFORMATION: Barcoding sequence

<400> SEQUENCE: 977 gactccaac                                                                 9

<210> SEQ ID NO 978
<211> LENGTH: 9
<212> TYPE: DNA
<213> ORGANISM: Artificial Sequence
<220> FEATURE:
<223> OTHER INFORMATION: Barcoding sequence

<400> SEQUENCE: 978
``` agctccaac                                                              9

<210> SEQ ID NO 979
<211> LENGTH: 9
<212> TYPE: DNA
<213> ORGANISM: Artificial Sequence
<220> FEATURE:
<223> OTHER INFORMATION: Barcoding sequence

<400> SEQUENCE: 979 tcctccaac                                                              9

<210> SEQ ID NO 980
<211> LENGTH: 9
<212> TYPE: DNA
<213> ORGANISM: Artificial Sequence
<220> FEATURE:
<223> OTHER INFORMATION: Barcoding sequence

<400> SEQUENCE: 980 ctctccaac                                                              9

<210> SEQ ID NO 981
<211> LENGTH: 9
<212> TYPE: DNA
<213> ORGANISM: Artificial Sequence
<220> FEATURE:
<223> OTHER INFORMATION: Barcoding sequence

<400> SEQUENCE: 981 ggttccaac                                                              9

<210> SEQ ID NO 982
<211> LENGTH: 9
<212> TYPE: DNA
<213> ORGANISM: Artificial Sequence
<220> FEATURE:
<223> OTHER INFORMATION: Barcoding sequence

<400> SEQUENCE: 982 ccttccaac                                                              9

<210> SEQ ID NO 983
<211> LENGTH: 9
<212> TYPE: DNA
<213> ORGANISM: Artificial Sequence
<220> FEATURE:
<223> OTHER INFORMATION: Barcoding sequence

<400> SEQUENCE: 983 cggatcaac                                                              9

<210> SEQ ID NO 984
<211> LENGTH: 9
<212> TYPE: DNA
<213> ORGANISM: Artificial Sequence
<220> FEATURE:
<223> OTHER INFORMATION: Barcoding sequence

<400> SEQUENCE: 984 gcgatcaac                                                              9

<210> SEQ ID NO 985
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 985 ggcatcaac                                                                  9

<210> SEQ ID NO 986
<211> LENGTH: 9
<212> TYPE: DNA
<213> ORGANISM: Artificial Sequence
<220> FEATURE:
<223> OTHER INFORMATION: Barcoding sequence

<400> SEQUENCE: 986 ggagtcaac                                                                  9

<210> SEQ ID NO 987
<211> LENGTH: 9
<212> TYPE: DNA
<213> ORGANISM: Artificial Sequence
<220> FEATURE:
<223> OTHER INFORMATION: Barcoding sequence

<400> SEQUENCE: 987 ccagtcaac                                                                  9

<210> SEQ ID NO 988
<211> LENGTH: 9
<212> TYPE: DNA
<213> ORGANISM: Artificial Sequence
<220> FEATURE:
<223> OTHER INFORMATION: Barcoding sequence

<400> SEQUENCE: 988 gaggtcaac                                                                  9

<210> SEQ ID NO 989
<211> LENGTH: 9
<212> TYPE: DNA
<213> ORGANISM: Artificial Sequence
<220> FEATURE:
<223> OTHER INFORMATION: Barcoding sequence

<400> SEQUENCE: 989 acggtcaac                                                                  9

<210> SEQ ID NO 990
<211> LENGTH: 9
<212> TYPE: DNA
<213> ORGANISM: Artificial Sequence
<220> FEATURE:
<223> OTHER INFORMATION: Barcoding sequence

<400> SEQUENCE: 990 ctggtcaac                                                                  9

<210> SEQ ID NO 991
<211> LENGTH: 9
<212> TYPE: DNA
<213> ORGANISM: Artificial Sequence
<220> FEATURE:
<223> OTHER INFORMATION: Barcoding sequence

<400> SEQUENCE: 991 cacgtcaac                                                                  9
```

```
<210> SEQ ID NO 992
<211> LENGTH: 9
<212> TYPE: DNA
<213> ORGANISM: Artificial Sequence
<220> FEATURE:
<223> OTHER INFORMATION: Barcoding sequence

<400> SEQUENCE: 992 agcgtcaac                                                                9

<210> SEQ ID NO 993
<211> LENGTH: 9
<212> TYPE: DNA
<213> ORGANISM: Artificial Sequence
<220> FEATURE:
<223> OTHER INFORMATION: Barcoding sequence

<400> SEQUENCE: 993 tccgtcaac                                                                9

<210> SEQ ID NO 994
<211> LENGTH: 9
<212> TYPE: DNA
<213> ORGANISM: Artificial Sequence
<220> FEATURE:
<223> OTHER INFORMATION: Barcoding sequence

<400> SEQUENCE: 994 gtcgtcaac                                                                9

<210> SEQ ID NO 995
<211> LENGTH: 9
<212> TYPE: DNA
<213> ORGANISM: Artificial Sequence
<220> FEATURE:
<223> OTHER INFORMATION: Barcoding sequence

<400> SEQUENCE: 995 cgtgtcaac                                                                9

<210> SEQ ID NO 996
<211> LENGTH: 9
<212> TYPE: DNA
<213> ORGANISM: Artificial Sequence
<220> FEATURE:
<223> OTHER INFORMATION: Barcoding sequence

<400> SEQUENCE: 996 gctgtcaac                                                                9

<210> SEQ ID NO 997
<211> LENGTH: 9
<212> TYPE: DNA
<213> ORGANISM: Artificial Sequence
<220> FEATURE:
<223> OTHER INFORMATION: Barcoding sequence

<400> SEQUENCE: 997 cgactcaac                                                                9

<210> SEQ ID NO 998
<211> LENGTH: 9
<212> TYPE: DNA
<213> ORGANISM: Artificial Sequence
<220> FEATURE:
```

<223> OTHER INFORMATION: Barcoding sequence

<400> SEQUENCE: 998 gcactcaac                                                                    9

<210> SEQ ID NO 999
<211> LENGTH: 9
<212> TYPE: DNA
<213> ORGANISM: Artificial Sequence
<220> FEATURE:
<223> OTHER INFORMATION: Barcoding sequence

<400> SEQUENCE: 999 cagctcaac                                                                    9

<210> SEQ ID NO 1000
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1000 aggctcaac                                                                    9

<210> SEQ ID NO 1001
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1001 tcgctcaac                                                                    9

<210> SEQ ID NO 1002
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1002 gtgctcaac                                                                    9

<210> SEQ ID NO 1003
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1003 gacctcaac                                                                    9

<210> SEQ ID NO 1004
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1004 tgcctcaac                                                                    9

-continued

```
<210> SEQ ID NO 1005
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1005 ctcctcaac                                                                  9

<210> SEQ ID NO 1006
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1006 ggtctcaac                                                                  9

<210> SEQ ID NO 1007
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1007 cctctcaac                                                                  9

<210> SEQ ID NO 1008
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1008 ccgttcaac                                                                  9

<210> SEQ ID NO 1009
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1009 cgcttcaac                                                                  9

<210> SEQ ID NO 1010
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1010 gccttcaac                                                                  9

<210> SEQ ID NO 1011
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 1011 gcggataac                                                             9

<210> SEQ ID NO 1012
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1012 ggcgataac                                                             9

<210> SEQ ID NO 1013
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1013 cggcataac                                                             9

<210> SEQ ID NO 1014
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1014 cggagtaac                                                             9

<210> SEQ ID NO 1015
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1015 gcgagtaac                                                             9

<210> SEQ ID NO 1016
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1016 ggcagtaac                                                             9

<210> SEQ ID NO 1017
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1017 ggaggtaac                                                             9

<210> SEQ ID NO 1018
<211> LENGTH: 9
```

-continued

```
<212> TYPE: DNA
<213> ORGANISM: Artificial Sequence
<220> FEATURE:
<223> OTHER INFORMATION: Barcoding sequence

<400> SEQUENCE: 1018 ccaggtaac                                                              9

<210> SEQ ID NO 1019
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1019 gacggtaac                                                              9

<210> SEQ ID NO 1020
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1020 agcggtaac                                                              9

<210> SEQ ID NO 1021
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1021 tccggtaac                                                              9

<210> SEQ ID NO 1022
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1022 ctcggtaac                                                              9

<210> SEQ ID NO 1023
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1023 cgtggtaac                                                              9

<210> SEQ ID NO 1024
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1024
``` gctggtaac                                                                 9

<210> SEQ ID NO 1025
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1025 cgacgtaac                                                                 9

<210> SEQ ID NO 1026
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1026 gcacgtaac                                                                 9

<210> SEQ ID NO 1027
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1027 gagcgtaac                                                                 9

<210> SEQ ID NO 1028
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1028 aggcgtaac                                                                 9

<210> SEQ ID NO 1029
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1029 tcgcgtaac                                                                 9

<210> SEQ ID NO 1030
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1030 ctgcgtaac                                                                 9

<210> SEQ ID NO 1031
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 1031 caccgtaac                                                                      9

<210> SEQ ID NO 1032
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1032 tgccgtaac                                                                      9

<210> SEQ ID NO 1033
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1033 gtccgtaac                                                                      9

<210> SEQ ID NO 1034
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1034 ggtcgtaac                                                                      9

<210> SEQ ID NO 1035
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1035 cctcgtaac                                                                      9

<210> SEQ ID NO 1036
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1036 ccgtgtaac                                                                      9

<210> SEQ ID NO 1037
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1037 cgctgtaac                                                                      9
```

```
<210> SEQ ID NO 1038
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1038 gcctgtaac                                                                 9

<210> SEQ ID NO 1039
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1039 ccgactaac                                                                 9

<210> SEQ ID NO 1040
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1040 cgcactaac                                                                 9

<210> SEQ ID NO 1041
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1041 gccactaac                                                                 9

<210> SEQ ID NO 1042
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1042 cgagctaac                                                                 9

<210> SEQ ID NO 1043
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1043 gcagctaac                                                                 9

<210> SEQ ID NO 1044
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 1044 gaggctaac                                                               9

<210> SEQ ID NO 1045
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1045 acggctaac                                                               9

<210> SEQ ID NO 1046
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1046 ctggctaac                                                               9

<210> SEQ ID NO 1047
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1047 cacgctaac                                                               9

<210> SEQ ID NO 1048
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1048 tgcgctaac                                                               9

<210> SEQ ID NO 1049
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1049 gtcgctaac                                                               9

<210> SEQ ID NO 1050
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1050 ggtgctaac                                                               9

<210> SEQ ID NO 1051
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1051 cctgctaac                                                                 9

<210> SEQ ID NO 1052
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1052 ggacctaac                                                                 9

<210> SEQ ID NO 1053
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1053 ccacctaac                                                                 9

<210> SEQ ID NO 1054
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1054 cagcctaac                                                                 9

<210> SEQ ID NO 1055
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1055 tggcctaac                                                                 9

<210> SEQ ID NO 1056
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1056 gtgcctaac                                                                 9

<210> SEQ ID NO 1057
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1057
``` cgtcctaac                                                                9

<210> SEQ ID NO 1058
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1058 gctcctaac                                                                9

<210> SEQ ID NO 1059
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1059 cggtctaac                                                                9

<210> SEQ ID NO 1060
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1060 gcgtctaac                                                                9

<210> SEQ ID NO 1061
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1061 ggctctaac                                                                9

<210> SEQ ID NO 1062
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1062 ccggttaac                                                                9

<210> SEQ ID NO 1063
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1063 cgcgttaac                                                                9

<210> SEQ ID NO 1064
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 1064 gccgttaac                                                                9

<210> SEQ ID NO 1065
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1065 gcgcttaac                                                                9

<210> SEQ ID NO 1066
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1066 ggccttaac                                                                9

<210> SEQ ID NO 1067
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1067 ggagaagac                                                                9

<210> SEQ ID NO 1068
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1068 ccagaagac                                                                9

<210> SEQ ID NO 1069
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1069 gaggaagac                                                                9

<210> SEQ ID NO 1070
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1070 acggaagac                                                                9
```

```
<210> SEQ ID NO 1071
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1071 ctggaagac                                                                   9

<210> SEQ ID NO 1072
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1072 cacgaagac                                                                   9

<210> SEQ ID NO 1073
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1073 agcgaagac                                                                   9

<210> SEQ ID NO 1074
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1074 tccgaagac                                                                   9

<210> SEQ ID NO 1075
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1075 gtcgaagac                                                                   9

<210> SEQ ID NO 1076
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1076 cgtgaagac                                                                   9

<210> SEQ ID NO 1077
<211> LENGTH: 9
<212> TYPE: DNA
<213> ORGANISM: Artificial Sequence
<220> FEATURE:
```

```
<223> OTHER INFORMATION: Barcoding sequence

<400> SEQUENCE: 1077 gctgaagac                                                                        9

<210> SEQ ID NO 1078
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1078 cgacaagac                                                                        9

<210> SEQ ID NO 1079
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1079 gcacaagac                                                                        9

<210> SEQ ID NO 1080
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1080 cagcaagac                                                                        9

<210> SEQ ID NO 1081
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1081 aggcaagac                                                                        9

<210> SEQ ID NO 1082
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1082 tcgcaagac                                                                        9

<210> SEQ ID NO 1083
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1083 gtgcaagac                                                                        9
```

```
<210> SEQ ID NO 1084
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1084 gaccaagac                                                                9

<210> SEQ ID NO 1085
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1085 tgccaagac                                                                9

<210> SEQ ID NO 1086
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1086 ctccaagac                                                                9

<210> SEQ ID NO 1087
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1087 ggtcaagac                                                                9

<210> SEQ ID NO 1088
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1088 cctcaagac                                                                9

<210> SEQ ID NO 1089
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1089 cggtaagac                                                                9

<210> SEQ ID NO 1090
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 1090 gcgtaagac                                                               9

<210> SEQ ID NO 1091
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1091 ggctaagac                                                               9

<210> SEQ ID NO 1092
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1092 ggaagagac                                                               9

<210> SEQ ID NO 1093
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1093 ccaagagac                                                               9

<210> SEQ ID NO 1094
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1094 gagagagac                                                               9

<210> SEQ ID NO 1095
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1095 aggagagac                                                               9

<210> SEQ ID NO 1096
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1096 tcgagagac                                                               9

<210> SEQ ID NO 1097
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 1097 ctgagagac                                                                 9

<210> SEQ ID NO 1098
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1098 cacagagac                                                                 9

<210> SEQ ID NO 1099
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1099 tgcagagac                                                                 9

<210> SEQ ID NO 1100
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1100 accagagac                                                                 9

<210> SEQ ID NO 1101
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1101 gtcagagac                                                                 9

<210> SEQ ID NO 1102
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1102 cgtagagac                                                                 9

<210> SEQ ID NO 1103
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1103
```

```
gctagagac                                                              9

<210> SEQ ID NO 1104
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1104 gaaggagac                                                              9

<210> SEQ ID NO 1105
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1105 agaggagac                                                              9

<210> SEQ ID NO 1106
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1106 tcaggagac                                                              9

<210> SEQ ID NO 1107
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1107 ctaggagac                                                              9

<210> SEQ ID NO 1108
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1108 aacggagac                                                              9

<210> SEQ ID NO 1109
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1109 ttcggagac                                                              9

<210> SEQ ID NO 1110
<211> LENGTH: 9
<212> TYPE: DNA
<213> ORGANISM: Artificial Sequence
```

```
<220> FEATURE:
<223> OTHER INFORMATION: Barcoding sequence

<400> SEQUENCE: 1110 catggagac                                                                 9

<210> SEQ ID NO 1111
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1111 tgtggagac                                                                 9

<210> SEQ ID NO 1112
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1112 actggagac                                                                 9

<210> SEQ ID NO 1113
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1113 gttggagac                                                                 9

<210> SEQ ID NO 1114
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1114 caacgagac                                                                 9

<210> SEQ ID NO 1115
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1115 tgacgagac                                                                 9

<210> SEQ ID NO 1116
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1116 acacgagac                                                                 9
```

<210> SEQ ID NO 1117
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1117 gtacgagac                                                                 9

<210> SEQ ID NO 1118
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1118 aagcgagac                                                                 9

<210> SEQ ID NO 1119
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1119 ttgcgagac                                                                 9

<210> SEQ ID NO 1120
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1120 taccgagac                                                                 9

<210> SEQ ID NO 1121
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1121 atccgagac                                                                 9

<210> SEQ ID NO 1122
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1122 gatcgagac                                                                 9

<210> SEQ ID NO 1123
<211> LENGTH: 9
<212> TYPE: DNA
<213> ORGANISM: Artificial Sequence
<220> FEATURE:
<223> OTHER INFORMATION: Barcoding sequence

```
<400> SEQUENCE: 1123 agtcgagac                                                              9

<210> SEQ ID NO 1124
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1124 cttcgagac                                                              9

<210> SEQ ID NO 1125
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1125 cgatgagac                                                              9

<210> SEQ ID NO 1126
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1126 gcatgagac                                                              9

<210> SEQ ID NO 1127
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1127 cagtgagac                                                              9

<210> SEQ ID NO 1128
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1128 tggtgagac                                                              9

<210> SEQ ID NO 1129
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1129 acgtgagac                                                              9

<210> SEQ ID NO 1130
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1130 gtgtgagac                                                                 9

<210> SEQ ID NO 1131
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1131 gactgagac                                                                 9

<210> SEQ ID NO 1132
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1132 agctgagac                                                                 9

<210> SEQ ID NO 1133
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1133 tcctgagac                                                                 9

<210> SEQ ID NO 1134
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1134 ctctgagac                                                                 9

<210> SEQ ID NO 1135
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1135 ggttgagac                                                                 9

<210> SEQ ID NO 1136
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1136
``` ccttgagac 9

<210> SEQ ID NO 1137
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1137 cgaacagac 9

<210> SEQ ID NO 1138
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1138 gcaacagac 9

<210> SEQ ID NO 1139
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1139 cagacagac 9

<210> SEQ ID NO 1140
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1140 tggacagac 9

<210> SEQ ID NO 1141
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1141 acgacagac 9

<210> SEQ ID NO 1142
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1142 gtgacagac 9

<210> SEQ ID NO 1143
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 1143 gacacagac                                                              9

<210> SEQ ID NO 1144
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1144 agcacagac                                                              9

<210> SEQ ID NO 1145
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1145 tccacagac                                                              9

<210> SEQ ID NO 1146
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1146 ctcacagac                                                              9

<210> SEQ ID NO 1147
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1147 ggtacagac                                                              9

<210> SEQ ID NO 1148
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1148 cctacagac                                                              9

<210> SEQ ID NO 1149
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1149 cacgaa                                                                 6
```

```
<210> SEQ ID NO 1150
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1150 taaggc                                                                    6

<210> SEQ ID NO 1151
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1151 tgatgg                                                                    6

<210> SEQ ID NO 1152
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1152 tggcat                                                                    6

<210> SEQ ID NO 1153
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1153 ccagaa                                                                    6

<210> SEQ ID NO 1154
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1154 atccga                                                                    6

<210> SEQ ID NO 1155
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1155 cgaaca                                                                    6

<210> SEQ ID NO 1156
<211> LENGTH: 6
<212> TYPE: DNA
<213> ORGANISM: Artificial Sequence
<220> FEATURE:
```

<223> OTHER INFORMATION: Barcoding sequence

<400> SEQUENCE: 1156 catgag                                                                    6

<210> SEQ ID NO 1157
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1157 taggtg                                                                    6

<210> SEQ ID NO 1158
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1158 catagc                                                                    6

<210> SEQ ID NO 1159
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1159 ccacat                                                                    6

<210> SEQ ID NO 1160
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1160 accaca                                                                    6

<210> SEQ ID NO 1161
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1161 gatacc                                                                    6

<210> SEQ ID NO 1162
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1162 cagaac                                                                    6

```
<210> SEQ ID NO 1163
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1163 ccacta                                                                  6

<210> SEQ ID NO 1164
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1164 cagtag                                                                  6

<210> SEQ ID NO 1165
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1165 acaagc                                                                  6

<210> SEQ ID NO 1166
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1166 tcatgc                                                                  6

<210> SEQ ID NO 1167
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1167 atcacc                                                                  6

<210> SEQ ID NO 1168
<211> LENGTH: 6
<212> TYPE: DNA
<213> ORGANISM: Artificial Sequence
<220> FEATURE:
<223> OTHER INFORMATION: Barcoding sequence

<400> SEQUENCE: 1168 gactag                                                                  6

<210> SEQ ID NO 1169
<211> LENGTH: 6
<212> TYPE: DNA
<213> ORGANISM: Artificial Sequence
<220> FEATURE:
<223> OTHER INFORMATION: Barcoding sequence
```

```
<400> SEQUENCE: 1169 cttcga                                                              6

<210> SEQ ID NO 1170
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1170 cggaagaat                                                           9

<210> SEQ ID NO 1171
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1171 gcgaagaat                                                           9

<210> SEQ ID NO 1172
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1172 ggcaagaat                                                           9

<210> SEQ ID NO 1173
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1173 ggagagaat                                                           9

<210> SEQ ID NO 1174
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1174 ccagagaat                                                           9

<210> SEQ ID NO 1175
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1175 gaggagaat                                                           9

<210> SEQ ID NO 1176
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 1176 acggagaat                                                                 9

<210> SEQ ID NO 1177
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1177 ctggagaat                                                                 9

<210> SEQ ID NO 1178
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1178 cacgagaat                                                                 9

<210> SEQ ID NO 1179
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1179 agcgagaat                                                                 9

<210> SEQ ID NO 1180
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1180 tccgagaat                                                                 9

<210> SEQ ID NO 1181
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1181 gtcgagaat                                                                 9

<210> SEQ ID NO 1182
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1182
```

-continued cgtgagaat                                                                          9

<210> SEQ ID NO 1183
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1183 gctgagaat                                                                          9

<210> SEQ ID NO 1184
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1184 cgacagaat                                                                          9

<210> SEQ ID NO 1185
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1185 gcacagaat                                                                          9

<210> SEQ ID NO 1186
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1186 cagcagaat                                                                          9

<210> SEQ ID NO 1187
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1187 aggcagaat                                                                          9

<210> SEQ ID NO 1188
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1188 tcgcagaat                                                                          9

<210> SEQ ID NO 1189
<211> LENGTH: 9
<212> TYPE: DNA
<213> ORGANISM: Artificial Sequence

```
<220> FEATURE:
<223> OTHER INFORMATION: Barcoding sequence

<400> SEQUENCE: 1189 gtgcagaat                                                              9

<210> SEQ ID NO 1190
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1190 gaccagaat                                                              9

<210> SEQ ID NO 1191
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1191 tgccagaat                                                              9

<210> SEQ ID NO 1192
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1192 ctccagaat                                                              9

<210> SEQ ID NO 1193
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1193 ggtcagaat                                                              9

<210> SEQ ID NO 1194
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1194 cctcagaat                                                              9

<210> SEQ ID NO 1195
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1195 ccgtagaat                                                              9
```

<210> SEQ ID NO 1196
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1196 cgctagaat                                                                  9

<210> SEQ ID NO 1197
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1197 gcctagaat                                                                  9

<210> SEQ ID NO 1198
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1198 ggaaggaat                                                                  9

<210> SEQ ID NO 1199
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1199 ccaaggaat                                                                  9

<210> SEQ ID NO 1200
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1200 gagaggaat                                                                  9

<210> SEQ ID NO 1201
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1201 aggaggaat                                                                  9

<210> SEQ ID NO 1202
<211> LENGTH: 9
<212> TYPE: DNA
<213> ORGANISM: Artificial Sequence
<220> FEATURE:
<223> OTHER INFORMATION: Barcoding sequence

```
<400> SEQUENCE: 1202 tcgaggaat                                                                      9

<210> SEQ ID NO 1203
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1203 ctgaggaat                                                                      9

<210> SEQ ID NO 1204
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1204 cacaggaat                                                                      9

<210> SEQ ID NO 1205
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1205 tgcaggaat                                                                      9

<210> SEQ ID NO 1206
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1206 accaggaat                                                                      9

<210> SEQ ID NO 1207
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1207 gtcaggaat                                                                      9

<210> SEQ ID NO 1208
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1208 cgtaggaat                                                                      9

<210> SEQ ID NO 1209
```

```
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1209 gctaggaat                                                                  9

<210> SEQ ID NO 1210
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1210 gaacggaat                                                                  9

<210> SEQ ID NO 1211
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1211 agacggaat                                                                  9

<210> SEQ ID NO 1212
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1212 tcacggaat                                                                  9

<210> SEQ ID NO 1213
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1213 ctacggaat                                                                  9

<210> SEQ ID NO 1214
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1214 aagcggaat                                                                  9

<210> SEQ ID NO 1215
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1215
``` ttgcggaat                                                              9

<210> SEQ ID NO 1216
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1216 taccggaat                                                              9

<210> SEQ ID NO 1217
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1217 atccggaat                                                              9

<210> SEQ ID NO 1218
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1218 catcggaat                                                              9

<210> SEQ ID NO 1219
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1219 tgtcggaat                                                              9

<210> SEQ ID NO 1220
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1220 actcggaat                                                              9

<210> SEQ ID NO 1221
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1221 gttcggaat                                                              9

<210> SEQ ID NO 1222
<211> LENGTH: 9
<212> TYPE: DNA

```
<213> ORGANISM: Artificial Sequence
<220> FEATURE:
<223> OTHER INFORMATION: Barcoding sequence

<400> SEQUENCE: 1222 cgatggaat                                                                  9

<210> SEQ ID NO 1223
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1223 gcatggaat                                                                  9

<210> SEQ ID NO 1224
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1224 cagtggaat                                                                  9

<210> SEQ ID NO 1225
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1225 tggtggaat                                                                  9

<210> SEQ ID NO 1226
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1226 acgtggaat                                                                  9

<210> SEQ ID NO 1227
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1227 gtgtggaat                                                                  9

<210> SEQ ID NO 1228
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1228 gactggaat                                                                  9
```

```
<210> SEQ ID NO 1229
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1229 agctggaat                                                                 9

<210> SEQ ID NO 1230
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1230 tcctggaat                                                                 9

<210> SEQ ID NO 1231
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1231 ctctggaat                                                                 9

<210> SEQ ID NO 1232
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1232 ggttggaat                                                                 9

<210> SEQ ID NO 1233
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1233 ccttggaat                                                                 9

<210> SEQ ID NO 1234
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1234 cgaacgaat                                                                 9

<210> SEQ ID NO 1235
<211> LENGTH: 9
<212> TYPE: DNA
<213> ORGANISM: Artificial Sequence
<220> FEATURE:
```

-continued

<223> OTHER INFORMATION: Barcoding sequence

<400> SEQUENCE: 1235 gcaacgaat                                                                                       9

<210> SEQ ID NO 1236
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1236 cagacgaat                                                                                       9

<210> SEQ ID NO 1237
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1237 tggacgaat                                                                                       9

<210> SEQ ID NO 1238
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1238 acgacgaat                                                                                       9

<210> SEQ ID NO 1239
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1239 gtgacgaat                                                                                       9

<210> SEQ ID NO 1240
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1240 gacacgaat                                                                                       9

<210> SEQ ID NO 1241
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1241 agcacgaat                                                                                       9

```
<210> SEQ ID NO 1242
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1242 tccacgaat                                                                  9

<210> SEQ ID NO 1243
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1243 ctcacgaat                                                                  9

<210> SEQ ID NO 1244
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1244 tagctcgaa                                                                  9

<210> SEQ ID NO 1245
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1245 atgctcgaa                                                                  9

<210> SEQ ID NO 1246
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1246 aacctcgaa                                                                  9

<210> SEQ ID NO 1247
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1247 ttcctcgaa                                                                  9

<210> SEQ ID NO 1248
<211> LENGTH: 9
<212> TYPE: DNA
<213> ORGANISM: Artificial Sequence
<220> FEATURE:
<223> OTHER INFORMATION: Barcoding sequence
```

```
<400> SEQUENCE: 1248 gatctcgaa                                                                 9

<210> SEQ ID NO 1249
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1249 agtctcgaa                                                                 9

<210> SEQ ID NO 1250
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1250 tctctcgaa                                                                 9

<210> SEQ ID NO 1251
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1251 cttctcgaa                                                                 9

<210> SEQ ID NO 1252
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1252 ggattcgaa                                                                 9

<210> SEQ ID NO 1253
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1253 ccattcgaa                                                                 9

<210> SEQ ID NO 1254
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1254 cagttcgaa                                                                 9

<210> SEQ ID NO 1255
<211> LENGTH: 9
```

```
<212> TYPE: DNA
<213> ORGANISM: Artificial Sequence
<220> FEATURE:
<223> OTHER INFORMATION: Barcoding sequence

<400> SEQUENCE: 1255 tggttcgaa                                                                  9

<210> SEQ ID NO 1256
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1256 acgttcgaa                                                                  9

<210> SEQ ID NO 1257
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1257 gtgttcgaa                                                                  9

<210> SEQ ID NO 1258
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1258 gacttcgaa                                                                  9

<210> SEQ ID NO 1259
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1259 agcttcgaa                                                                  9

<210> SEQ ID NO 1260
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1260 caagcagac                                                                  9

<210> SEQ ID NO 1261
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1261
``` tgagcagac                                                                         9

<210> SEQ ID NO 1262
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1262 acagcagac                                                                         9

<210> SEQ ID NO 1263
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1263 gtagcagac                                                                         9

<210> SEQ ID NO 1264
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1264 aaggcagac                                                                         9

<210> SEQ ID NO 1265
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1265 ttggcagac                                                                         9

<210> SEQ ID NO 1266
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1266 tacgcagac                                                                         9

<210> SEQ ID NO 1267
<211> LENGTH: 9
<212> TYPE: DNA
<213> ORGANISM: Artificial Sequence
<220> FEATURE:
<223> OTHER INFORMATION: Barcoding sequence

<400> SEQUENCE: 1267 atcgcagac                                                                         9

<210> SEQ ID NO 1268
<211> LENGTH: 22
<212> TYPE: DNA
<213> ORGANISM: artificial sequence

```
<220> FEATURE:
<223> OTHER INFORMATION: Profiling 1

<400> SEQUENCE: 1268
ttctagagcg gccgcttcga gc                                              22

<210> SEQ ID NO 1269
<211> LENGTH: 22
<212> TYPE: DNA
<213> ORGANISM: artificial sequence
<220> FEATURE:
<223> OTHER INFORMATION: Profiling 2

<400> SEQUENCE: 1269
cgctgatctc acgccgtggt ga                                              22

<210> SEQ ID NO 1270
<211> LENGTH: 22
<212> TYPE: DNA
<213> ORGANISM: artificial sequence
<220> FEATURE:
<223> OTHER INFORMATION: Tailing

<400> SEQUENCE: 1270
agttccgcgt acgtacggcg tc                                              22
```

SYSTEMS AND METHODS TO ASSESS RNA STABILITY

CROSS-REFERENCE TO RELATED APPLICATIONS

The current application claims priority to U.S. Provisional Patent Application No. 63/051,269, filed Jul. 13, 2020, U.S. Provisional Patent Application No. 63/165,662, filed Mar. 24, 2021, U.S. Provisional Patent Application No. 63/072,669, filed Aug. 31, 2020, and International Application PCT/US2021/040027, filed Jul. 1, 2021; the disclosures of which are hereby incorporated by reference in their entireties.

FIELD OF THE DISCLOSURE

The present invention relates to ribonucleic acid (RNA). More specifically, the present invention relates to RNA molecules with enhanced stability and translation and assessment thereof, and further relates to systems and methods to enhance RNA stability and translation.

INCORPORATION OF SEQUENCE LISTING

This application hereby incorporates by reference the material of the electronic Sequence Listing filed concurrently herewith. The material in the electronic Sequence Listing is submitted as a text (.txt) file entitled "06754PCT_Seq_List_ST25.txt" created on Aug. 23, 2021, which has a file size of approximately 240 KB, and is herein incorporated by reference in its entirety.

BACKGROUND OF THE DISCLOSURE

There are multiple problems with prior methodologies of effecting protein expression. For example, introduced DNA can integrate into host cell genomic DNA at some frequency, resulting in alterations and/or damage to the host cell genomic DNA. Alternatively, the heterologous deoxyribonucleic acid (DNA) introduced into a cell can be inherited by daughter cells (whether or not the heterologous DNA has integrated into the chromosome) or by offspring.

In addition, assuming proper delivery and no damage or integration into the host genome, there are multiple steps which must occur before the encoded protein is made. Once inside the cell, DNA must be transported into the nucleus where it is transcribed into RNA. The RNA transcribed from DNA must then enter the cytoplasm where it is translated into protein. Not only do the multiple processing steps from administered DNA to protein create lag times before the generation of the functional protein, each step represents an opportunity for error and damage to the cell. Further, it is known to be difficult to obtain DNA expression in cells as DNA frequently enters a cell but is not expressed or not expressed at reasonable rates or concentrations. This can be a particular problem when DNA is introduced into primary cells or modified cell lines.

Attempts have been made to use RNA and messenger RNA (mRNA) as therapeutic agents. However, RNA is generally unstable and highly susceptible to degradation.

SUMMARY OF THE DISCLOSURE

This summary is meant to provide examples and is not intended to be limiting of the scope of the invention in any way. For example, any feature included in an example of this summary is not required by the claims, unless the claims explicitly recite the feature. Also, the features described can be combined in a variety of ways. Various features and steps as described elsewhere in this disclosure can be included in the examples summarized here.

In one embodiment, a method to determine RNA stability includes obtaining a pool of RNA molecules, where each RNA molecule is uniquely encoded with a barcoding sequence and each barcoding sequence is flanked by at least one profiling sequence, treating the pool of RNA molecules under an experimental condition, and isolating the pool of RNA molecules at a specified timepoint to generate a fraction of RNA molecules showing stability under the experimental condition for the specified timepoint.

In a further embodiment, the method further includes sequencing the barcode sequence of each RNA molecule in the fraction to identify the presence of each RNA molecule in the fraction of RNA molecules.

In another embodiment, the method further includes stability of the RNA molecules associated with each barcode sequence in the fraction by identifying the prevalence of each barcode in the fraction.

In a still further embodiment, the treating step includes transfecting the pool of RNA molecules into a collection of cells.

In still another embodiment, the cells are selected from mammalian cells, yeast cells, bacteria cells, and plant cells.

In a yet further embodiment, the treating step includes adding the pool of RNA molecules to a cell lysate.

In yet another embodiment, the treatment condition is selected from temperature, pH, presence of certain molecules, presence of certain ions, concentration of certain molecules, concentration of certain ions, irradiation, buffer type, and buffer concentration.

In a further embodiment again, the method further includes size selecting for full-length RNA molecules.

In another embodiment again, size selecting includes one or more of agarose gel electrophoresis, polyacrylamide gel electrophoresis, and capillary electrophoresis.

In a further additional embodiment, size selecting includes treating the RNA molecules with a 5'-3' nuclease that is inhibited by the presence of a 5' cap moiety.

In a still further additional embodiment, size selecting includes performing reverse transcription PCR to amplify full-length RNA molecules.

In another additional embodiment, the isolating step further includes isolating the pool of RNA molecules at a second specified timepoint to generate a second fraction of RNA molecules showing stability under the experimental condition for the specified timepoint.

In a still yet further embodiment, a method to identify a degradation site within an RNA molecule includes obtaining a pool of RNA molecules, wherein the RNA molecules encode for a sequence of interest, treating the pool of RNA molecules under an experimental condition to degrade the RNA molecules in the pool of RNA molecules, isolating the pool of RNA molecules at a specified timepoint, ligating an adapter to one end of the degraded RNA molecules in the pool of RNA molecules, and sequencing the ligated and degraded RNA molecules in the pool of RNA molecules to identify the degradation locations in the pool of RNA molecules.

In still yet another embodiment, the adapter is ligated to the 5' end of the degraded RNA molecules.

In a still further embodiment again, the treatment condition is selected from temperature, pH, presence of certain molecules, presence of certain ions, concentration of certain molecules, concentration of certain ions, irradiation, buffer type, and buffer concentration.

In still another embodiment again, the pool of RNA molecules includes a plurality of sequences of interest, wherein each sequence of interest is uniquely encoded with a barcoding sequence and each barcoding sequence is flanked by at least one profiling sequence.

The foregoing and other objects, features, and advantages of the disclosed technology will become more apparent from the following detailed description, which proceeds with reference to the accompanying figures.

BRIEF DESCRIPTION OF THE DRAWINGS

FIG. 2 illustrates a generalized structure of RNA molecules in accordance with various embodiments of the invention.

FIG. 8A illustrates a full view of the heatmap and column and row labels; while FIG. 8B illustrates an enlarged view of the heatmap; FIG. 8C illustrates the row labels; and FIG. 8D illustrates the column labels.

DETAILED DESCRIPTION OF THE DISCLOSURE

Turning now to the drawings, systems and methods to quantify RNA stability and uses thereof are provided. Many embodiments provide RNA molecules, including messenger RNA (mRNA), that allow for an assessment of in vitro and/or in vivo stability. Further embodiments provide methods and systems to assess such stability as well as provide single base resolution of degradation products.

In vivo and in vitro stability are two independent problems for RNA. In vivo stability can depend on untranslated sequences at 3'-ends of mRNAs, structures and sequences that signal decay, process that identify premature stop codons, RNA elements recognized by cellular endonucleases and exonucleases, and ribosome-dependent decay processes. (See, e.g., Koh, W. S., Porter, J. R. & Batchelor, E. Tuning of mRNA stability through altering 3'-UTR sequences generates distinct output expression in a synthetic circuit driven by p53 oscillations. Sci Rep 9, 5976 (2019). doi: 10.1038/s41598-019-42509-y; Park E, Maquat L E. Staufen-mediated mRNA decay. Wiley Interdiscip Rev RNA. 2013 July-August; 4(4):423-35. doi: 10.1002/wrna.1168. Epub 2013 May 16. PMID: 23681777; PMCID: PMC3711692; Brogna, S., Wen, J. Nonsense-mediated mRNA decay (NMD) mechanisms. Nat Struct Mol Biol 16, 107-113 (2009). doi: 10.1038/nsmb.1550; Blandine C. Mercier, Emmanuel Labaronne, David Cluet, Alicia Bicknell, Antoine Corbin, Laura Guiguettaz, Fabien Aube, Laurent Modolo, Didier Auboeuf, Melissa J. Moore, Emiliano P. Ricci bioRxiv 2020.10.16.341222; doi: 10.1101/2020.10.16.341222; the disclosures of which are hereby incorporated by reference in their entireties.) RNA degradation in aqueous buffers can occur in much longer time scales, but this can accelerate in the presence of magnesium ($Mg^{2+}$) or in high pH. (See e.g., Hannah K. Wayment-Steele, Do Soon Kim, Christian A. Choe, John J. Nicol, Roger Wellington-Oguri, R. Andres Parra Sperberg, Po-Ssu Huang, Eterna Participants, Rhiju Das bioRxiv 2020.08.22.262931; doi: 10.1101/2020.08.22.262931; the disclosure of which is hereby incorporated by reference in its entirety.) Common strategies to stabilize mRNAs for in vivo stability (including appending long poly adenosine stretches; >100 As) can actually destabilize RNAs in vitro by adding additional locations for possible hydrolysis. Additionally, embedded structured segments, which are expected to stabilize RNAs against in-line hydrolysis have been shown to decrease stability of mRNAs inside human cells through a process termed structure-mediated RNA decay (SRD), involving cellular factors UPF1 and G3BP1. (See e.g., Fischer, Joseph W. et al. Molecular Cell, Volume 78, Issue 1, 70-84.e6; the disclosure of which is hereby incorporated by reference in its entirety.)

Figure 1:
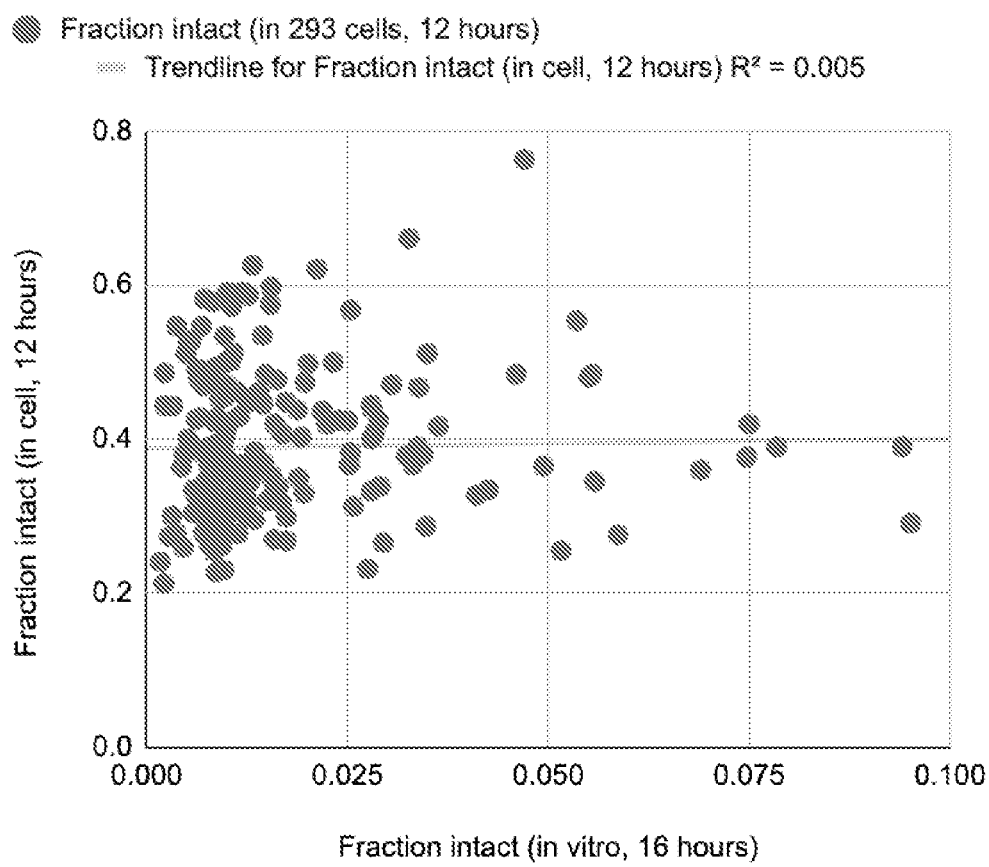
FIG. 1 illustrates exemplary results of in vitro versus in vivo RNA stability in accordance with various embodiments.

Exemplary data showing the no correlation between in vitro and in vivo stability is illustrated in FIG. 1. Specifically, FIG. 1 illustrates data from an empirical study of an mRNA library coding for nanoluciferase show that decay rates in human cells exhibit no correlation with in vitro decay rates. The in cell and in vitro stability possess an $r^2$ value of 0.0005, indicating no correlation. Such measurements were carried out using a library of 233 mRNAs of varying lengths (507-1215 nucleotides) and sequences. The measurements involve a reverse-transcription based assay to count RNAs remaining after degradation times, with strong reproducibility in ranking mRNA stabilities between time points or in replicates. In-cell measurements involved mRNAs transfected into human 293 cells. In vitro measurements were carried out under hydrolysis conditions (10 mM $MgCl_2$, 50 mM Na-CHES, pH 10.0, 24° C.) that accelerate hydrolysis by ~100× compared to neutral buffers without $Mg^{2+}$.

To be effective, nucleic acid-based therapeutics, including (but not limited to) mRNA vaccines, should be stable both in vitro and in vivo to be effective for both storage and efficacy. Thus, many embodiments describe an RNA design to allow for in vivo and/or in vitro screening as well as methods to assess in vivo and/or in vitro stability.

RNA Molecules and Design

Turning to FIG. 2, an exemplary structure for an embodiment of an RNA molecules in accordance with various is illustrated. Certain embodiments of an RNA molecule possess a 5' cap moiety. Some embodiments utilize a 7-methyl guanosine triphosphate as the cap moiety, but various additional cap sequences are known in the art for a 5' cap moiety. Additional embodiments possess a cap-proximal sequence for an mRNA located at the 5' end of the mRNA. Various cap sequences are known in the art for a 5' cap-proximal sequence. Certain embodiments use a small triplet, such as GGG as the cap-proximal sequence.

Additional embodiments of an RNA molecule possess a 5' untranslated region (5'UTR) sequence and/or a 3'UTR sequence. Certain embodiments place the 5'UTR near the 5' end of the RNA molecule, while the 3'UTR is located near the 3' end of the molecule. In some embodiments, the 5'UTR is located at the 3' end of the cap, while additional embodiments place the 5'UTR directly at the 5' end without a cap sequence. Similarly, a 3'UTR can be placed at the 3' end of a molecule, while additional embodiments may have a tailing sequence placed 3' of the 3'UTR. Certain embodiments select a 5'UTR and/or a 3'UTR for a variety of factors to increase stability and/or translation based on an innate sequence, while others select a 5'UTR and/or a 3'UTR for that may pose improved translation and/or stability based on a particular coding sequence of interest. Many possible 5'UTRs and 3'UTRs are known in the art, which are used in various embodiments.

Many embodiments of an RNA molecule possess a coding sequence, or CDS, located 3' from the 5'UTR, and 5' of the 3'UTR. In many embodiments, the CDS begins (e.g., at its 3' end) is with a start codon (e.g., the canonical AUG and/or any other codon shown to begin translation). In many embodiments, the a CDS terminates (e.g., at its 3' end) with a stop codon. In various embodiments the stop codon is a canonical stop codon (e.g., UAG, UAA, UGA), while further embodiments comprise noncanonical stop codons or sequences shown to terminate translation. Certain embodiments comprise more than one stop codon in the CDS.

The coding sequence is a designed sequence of interest to encode a protein or peptide of interest. In certain embodiments, the coding sequence encodes an epitope or other antigen to induce an immune response, thus allowing creation of a vaccine. In various embodiments, the protein or peptide of interest is used as a therapeutic directly, such that the protein or peptide of interest replaces or supplements a dysfunctional protein or peptide. In some embodiments, the protein or peptide of interest corrects for dysfunction of another protein or peptide. While protein coding sequences are described in the context of this exemplary embodiment, additional embodiments possess sequences for non-coding RNAs, such as RNAs that guide genome editing and/or coat chromatin. Various embodiments possess a CDS encoding a reporter gene; for example, nanoluciferase (SEQ ID NO: 1), green fluorescence protein, or any other reporter gene of interest.

Additional embodiments of an RNA molecule include a barcode to identify particular molecules based on unique sequences. Many barcode schemes are known in the art and range from 2 to 12 or more nucleotides. In many embodiments, the barcodes are 6-9 nucleotides in length. Certain embodiments select one or more barcodes from SEQ ID NOs: 2-1267.

To read barcodes, an RNA molecule can include one or more profiling sequences that can be used by PCR primers or sequencing primers to amplify and/or sequence the barcode region. In some embodiments profiling sequences are located at the 5' and/or 3' end of a barcode. In many embodiments, profiling sequences flank the barcode. In various embodiments profiling sequences are selected from profiling sequence 1 (SEQ ID NO: 1268) and profiling sequence 2 (SEQ ID NO: 1269).

As noted above, some embodiments of an RNA molecule possess a tailing sequence located at the 3' end of a molecule. In various embodiments the tailing sequence is used to add a poly-A tail or other structural sequence to an RNA molecule. In some embodiments, the tailing sequence is selected as SEQ ID NO: 1270.

Structures, such as those described above in regard to FIG. 2 allow for modular and combinatorial testing of various 5'UTRs, ORFs, and 3'UTRs.

Methods of Assessing In Vivo RNA Stability

Figure 3:
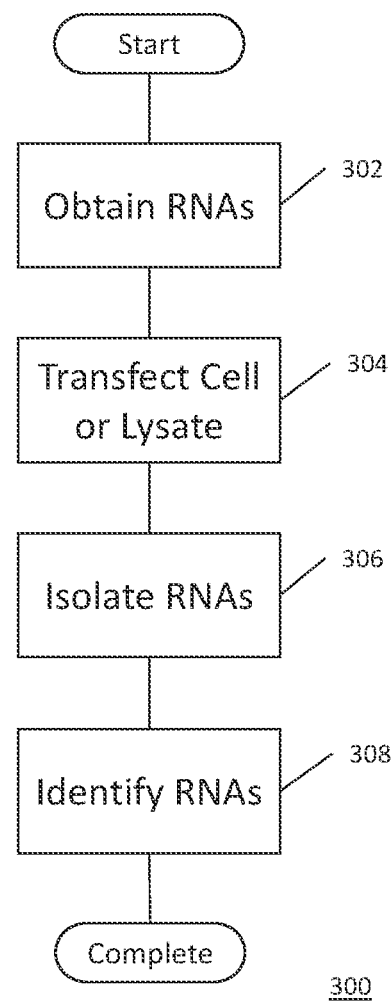
FIG. 3 illustrates a method to screen RNAs for increased in vivo stability in accordance with various embodiments of the invention.

Certain embodiments assess the stability of RNA molecules, including stability within in vivo and in vitro environments. An exemplary embodiment of a method 300 to assess stability is illustrated in FIG. 3. In method 300, RNA is obtained at 302. In certain embodiments, RNA molecules are generated via in vitro transcription. Additionally, certain embodiments generate an RNA transcript and/or further modify an RNA transcript to be ready for translation (e.g., including a 5' cap and/or a 3' polyA tail). In various embodiments, PCR is used to amplify one or more RNA molecules, including amplification of a template library. Additional embodiments assess amplicon quality via electrophoresis, including gel (agarose and/or polyacrylamide) and/or capillary electrophoresis (e.g., ABI 3700 and/or Agilent Bioanalyzer). Further embodiments transcribe these DNA amplicons to RNA using a DNA-dependent RNA polymerase. Certain embodiments perform the in vitro transcription using commercial kits, including Thermo's T7 MEGAScript. Various embodiments modify the RNA transcripts with a 5' cap and/or polyA tail. These modifications can be accomplished using kits, such as the Cellscript kit. Additional cleanups can be accomplished at various stages (e.g., after PCR, after transcription, and/or after modification), using columns or reagents, such as Thermo's MEGAClear columns. And, quality of the transcribed and/or modified RNAs can be accomplished via electrophoresis, including gel and capillary electrophoresis. In various embodiments, the RNA is provided as a pool of RNA sequences, where each unique RNA sequence comprises a unique barcode, such as described herein. In certain embodiments, the RNA molecules within the pool are approximately the same length.

Various embodiments transfect RNA transcripts into cells or add the transcripts to a cellular lysate at 304. In certain embodiments, transfection occurs on cultured cells or tissue, including mammalian cells, while other embodiments use yeast, bacteria, or plant cells. Some specific embodiments transfect HEK293T cells. Various embodiments incubate the transfected cells to allow for translation of the RNAs. Incubation can last between 1 hour and several days (e.g., 7-10 days) at temperatures and/or conditions to encourage cellular growth and translation. Culture media can include antibiotics or other selective reagents to prevent growth of non-transfected cells and/or contamination. Certain embodiments utilize a cellular lysate as a proxy of in vivo stress on RNA. In such embodiments, cultured cells are lysed via a known method, such as sonication, hydrodynamic stress, or any other method to generate cellular lysate. Then, the RNAs are added to the lysate and allowed to react for a period of time, such as between 1 hour and several days (e.g., 7-10 days) and at temperatures commensurate with the operating temperature for the RNA (e.g., average body temperature, 37° C.).

At 306, certain embodiments isolate RNAs based on in-cell stability. In various embodiments, RNAs are isolated from transfected cells, while some embodiments isolate the RNAs from a cellular lysate. Certain embodiments isolate RNA from transfected cells at various time points (e.g., after 1 hour, 2 hours, 3 hours, 6 hours, 12 hours, 24 hours, etc.) to create time-based fractions of RNAs. Additionally, isolated RNA molecules can be cleaned up via known procedures or kits, including isolation protocols, kits, columns, or any other know method for isolating RNA from cells or a lysate.

Various embodiments identify the RNAs based on their barcodes at 308. As noted above in relation to FIG. 2, many embodiments of RNA molecules contain a barcode sequence (e.g., SEQ ID NOs: 2-1267). The profiling sequences flanking the barcodes (e.g., SEQ ID NOs: 1268-1269) can be used to amplify the barcode or can be used as sequencing primers for barcoding reads of the RNA molecules of certain embodiments. Further embodiments utilize hybridization probes, quantitative PCR (qPCR), or any other known method with or without pooling strategies to identify which RNAs are present in timepoint based fractions.

Determination of In Vitro RNA Stability

Figure 4A:
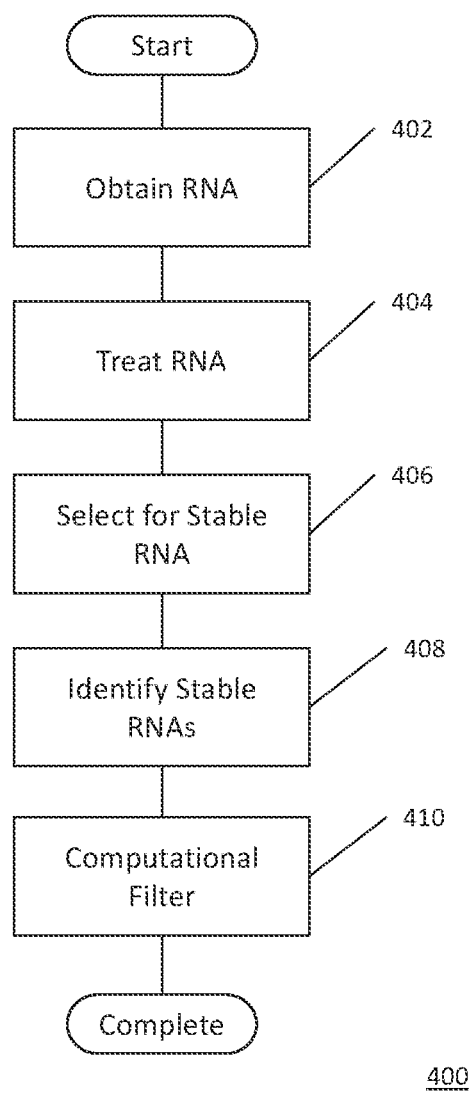
FIG. 4A illustrates a method to screen RNAs for increased in vitro stability in accordance with various embodiments of the invention.

An additional challenge for RNA therapeutics, including vaccines, include the stability in storage, such as between manufacture and actual treatment or delivery to an individual. Such stability is referred to as in vitro stability, as it emphasizes stability in non-biological environments, such as in vials, syringes, or other method of storage. Various embodiments provide a method to measure in vitro stability of RNAs. Turning to FIG. 4A, a method to determine in vitro RNA stability of RNA 400 in accordance with various embodiments is illustrated. Within method 400, RNA is obtained at 402. Obtaining RNA at 402 can be accomplished via many methods, including such steps as described in regard to method 300 (FIG. 3), including the obtention of a pool of RNA molecules, where each unique RNA sequence is identifiable by a unique barcode.

At 404 of many embodiments, the RNA pool is treated or subjected to an experimental condition. The experimental conditions include any condition that may cause degradation of an RNA molecule in a storage situation, including (but not limited to) temperature, pH, presence of certain molecules and/or ions, concentration of certain molecules and/or ions, irradiation, time, buffer type, buffer concentration, and/or any other condition that can affect RNA stability. Such conditions are meant to reproduce actual conditions that can induce one or more hydrolytic events within the RNA molecules. A hydrolytic event, in accordance with various embodiments, causes a break within the RNA molecule, resulting in a broken or incomplete RNA molecule. Incomplete or broken RNA molecules may be insufficient for use as a therapeutic, thus limiting the efficacy of the molecule.

Further embodiments further select for stable RNAs in the pool at 406. In some embodiments, the selection occurs by size selecting for full length RNAs, such as through electrophoresis, including (but not limited to) agarose gel electrophoresis, polyacrylamide electrophoresis, and capillary electrophoresis. However, additional embodiments perform a nuclease digestion reaction that is selective for damaged or degraded RNA. In certain digestion reactions, the nuclease is a 5'-3' nuclease that is inhibited by the presence of a 5' cap moiety—XRN1 is a non-limiting example of nuclease fitting this description. Being inhibited by a 5'cap prevents any stable or undamaged RNA molecules from being digested, thus causing damaged RNA to be eliminated from the pool.

Some embodiments select for stable RNAs by performing reverse transcription PCR (RT-PCR) to amplify full length RNAs into complimentary DNA (cDNA). By creating cDNAs, downstream amplifications can utilize DNA-dependent polymerases to create sequencing libraries or other molecules for analysis. Such embodiments select for full length RNAs rather than RNAs that may have been hydrolyzed but may still be of sufficient length that electrophoresis or other methods do not remove them.

At 408, stable RNAs are identified. In various embodiments, the undigested or gel-extracted RNAs are sequenced using the barcode to identify the particular molecules that are stable. In many embodiments, cDNAs created in 406 are utilized as templates to create a sequencing library to avoid the amplification of RNAs that may be near full length.

Figure 4B:
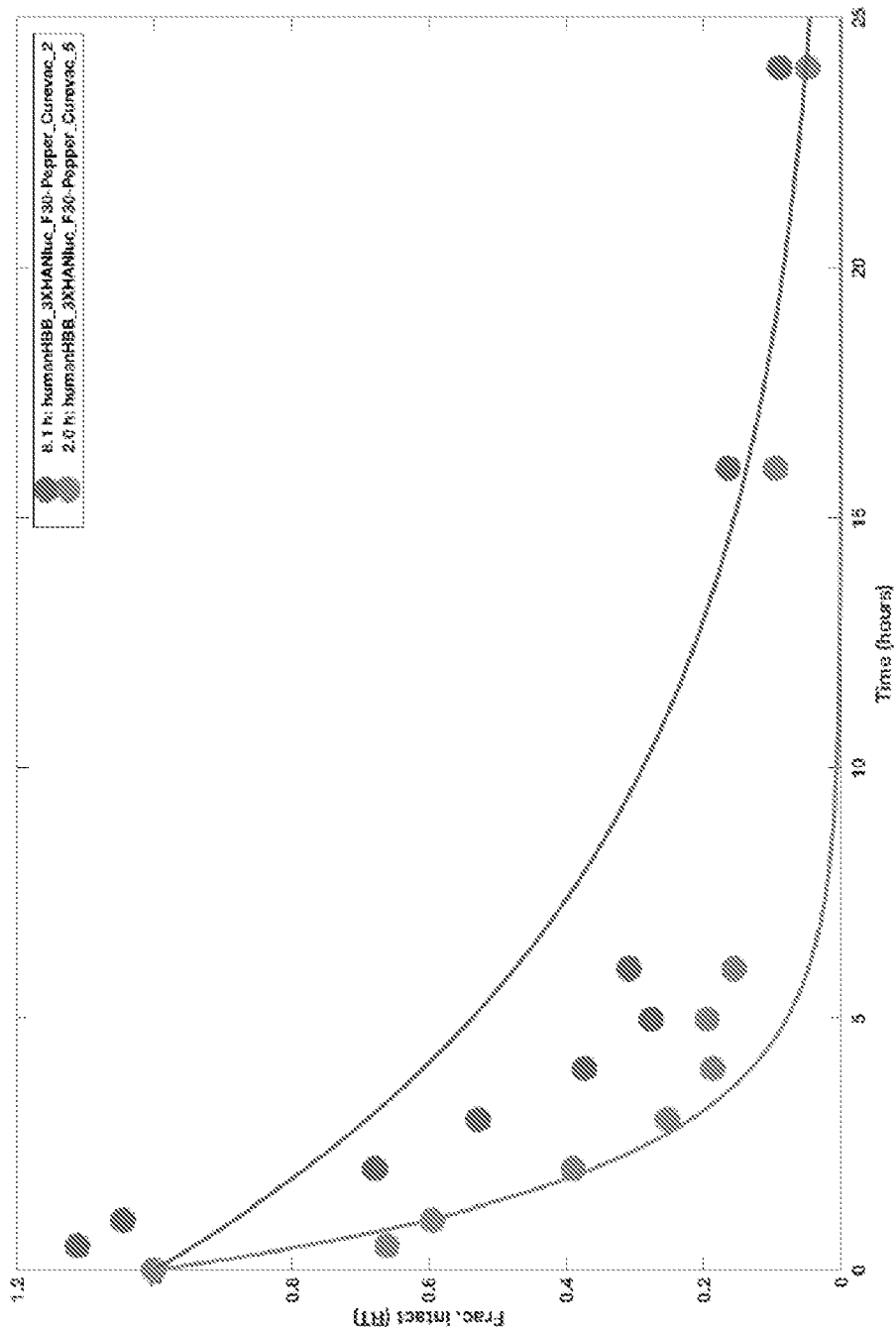
FIG. 4B illustrates an exemplary degradation curve in accordance with various embodiments of the invention.

Further embodiments integrate a computational filter 410 to remove artifacts from sequencing or other reactions that appear to show anomalous stability. For example, longer experimental conditions are generally expected to cause increased degradation. However, as illustrated in FIG. 4B, some exemplary RNA molecules show an anomalous persistence after extended times. To compensate for such artifacts, certain embodiments add a computational filter for RNA molecules in a pool. In many of such embodiments, the filter constructs a single-exponential curve for RNA molecules in a pool based on stability at various time points (e.g., 1 hour, 2 hours, 3, hours, 4 hours, 6 hours, 8 hours, etc.). For each RNA molecule, a difference between experimental fraction intact at the 24-hour time point (corresponding to >10 half-lives) and the expected intact fraction is calculated. If the residual fraction is greater than a particular threshold (e.g., 0.05), the RNA data is ignored.

Figure 5:
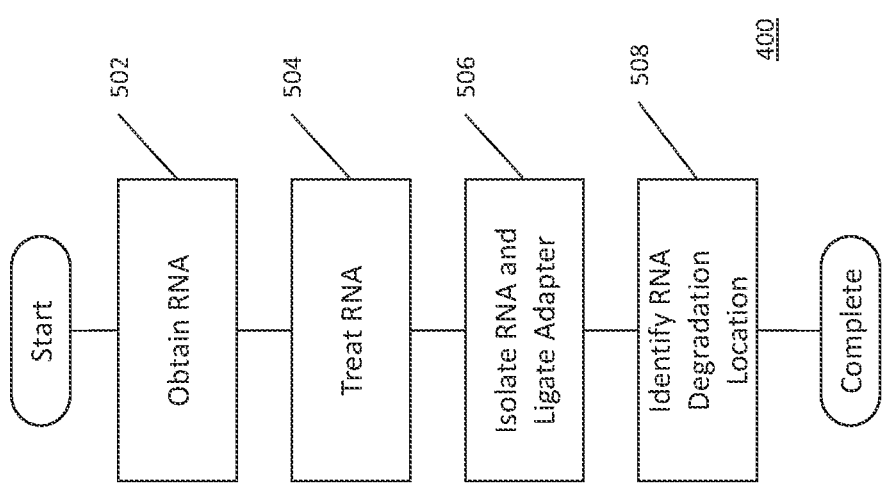
FIG. 5 illustrates a method to identify single nucleotide resolution of degradation in accordance with various embodiments of the invention.

Turning to FIG. 5, additional embodiments include method 500 to identify single nucleotide resolution of RNA degradation. Such embodiments couple inline probing with sequencing to identify specific locations of hydrolysis in an RNA molecule. In method 500 of various embodiments, RNA is obtained at 502. Obtaining RNA at 502 can be accomplished via many methods, including such steps as described in regard to method 300 (FIG. 3), including the obtention of a pool of RNA molecules, where each unique RNA sequence is identifiable by a unique barcode.

In many embodiments, the RNA is treated at 504. In many embodiments, treatment is similar to 404 of method 400 or 304 of method 300. Such treatments can include variations in time, temperature, pH, buffer components, etc. Treatment in accordance with various embodiments is utilized to induce one or more hydrolytic or degradation events within one or more RNA molecules.

At 506, various embodiments isolate RNA from the treatment and ligate an adapter to the 5' end of the molecules within the sample. The purpose of the 5' ligation is to preserve the 3' barcode comprised within RNA molecules of various embodiments. Various embodiments further utilize additional enzymes and reagents, such as kinases, ligases, ATP, buffers, etc. to ligate an adapter to the 5' end of RNAs and RNA fragments after treatment at 504. In various embodiments, the adapter possesses a sequencing primer and/or provides for a polymerase amplification. By ligating the adapter to the 5' end of a molecule, the 5' position of the hydrolysis is preserved by the adapter for downstream analysis.

At 508, the degradation location of the RNA is identified. In many embodiments, the RNA is sequenced to identify the specific base remaining intact. Certain embodiments include building sequencing libraries or other intermediate steps to sequence RNAs, as applicable to a particular sequencing platform (e.g., Illumina, PacBio, IonTorrent, etc.).

Identifying RNAs Having Enhanced Stability and/or Translatability

Figure 6:
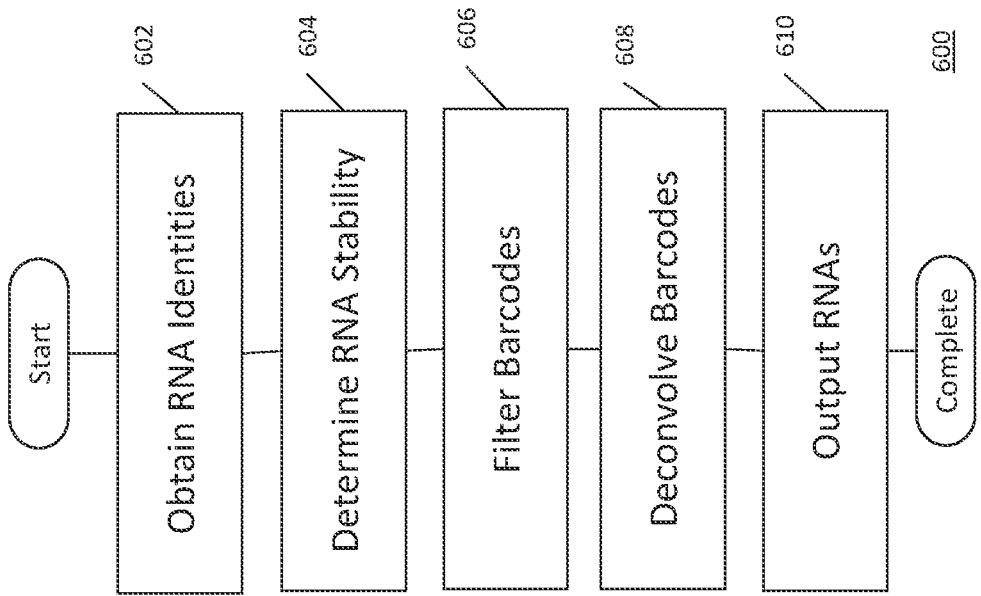
FIG. 6 illustrates a method to identify RNAs possessing increased in vivo and/or in vitro stability in accordance with various embodiments of the invention.

Turning to FIG. 6, various embodiments identify RNA molecules possessing increased stability (in vivo and/or in vitro) in method 600. At 602, many embodiments obtain identities of RNAs present in various fractions of stability (e.g., RNAs assessed via methods 300 or 400). In various embodiments, these identities include the barcode or barcodes that identify each of the RNA molecules in a fraction and a read count of each barcode in each fraction.

At 604, various embodiments determine the stability of each RNA by identifying prevalence of each barcode in each fraction. Certain embodiments perform statistical analyses to relative prevalence of the barcode in each fraction. The presence of RNAs in fractions correlating to longer times, indicate increased stability of that particular RNA. It should be noted that barcodes with higher stability (e.g., stable for at least 7 hours) will also show stability at shorter time points (e.g., 1 hour, 2 hours, 3 hours, etc.) As such, the absence of a barcode at a particular time point (as opposed to the presence of the barcode) may be of more importance for stability analysis.

Some embodiments filter RNA molecules based on particular characteristics at 606. Particular characteristics may be specific cutoffs or minimum levels of stability or translatability of a particular barcode. For example, certain embodiments omit barcodes that have limited in vitro stability as compared to in vivo stability or vice versa.

Various embodiments deconvolve the barcodes at 608, where deconvolution involves correlating the specific RNA sequence or sequence name is produced based on the barcode sequence.

Additional embodiments output results visualizing the stability and/or translatability of particular RNA molecules. Some embodiments produce heatmaps, dot plots, or other graphs or charts to visualize in vivo and/or in vitro stability of a particular RNA.

EXEMPLARY EMBODIMENTS

Although the following embodiments provide details on certain embodiments of the inventions, it should be understood that these are only exemplary in nature, and are not intended to limit the scope of the invention.

Example 1

Selection of Full-Length RNA Molecules to Assess Stability

Background: The natural experimental steps to select for full-length RNAs, based on literature precedent, involve (1) ribonuclease digestion to digest degraded RNAs and leave behind intact RNAs, as happens in living cells, or (2) electrophoresis to isolate the intact RNAs. Neither of these methods work, as illustrated by the following embodiment.

Methods: An inline hydrolysis event in RNA results in two fragments. The first fragment ends in a 2'-3' cyclic phosphate, and the other fragment begins with a 5' hydroxyl. Initially focusing on the use of the 5'-to-3' exonuclease Xrn1 to digest the second classes of fragments would result in elimination of any RNA that has a hydrolysis event 5' to a barcode residing in the 3' end of RNA molecules. Xrn1 acts 5'-to-3' on RNAs that have a 5' phosphate but not the initial 5' hydroxyl left by inline hydrolysis. Thus, in preparation for an Xrn1 digestion, T4 polynucleotide kinase and ATP were used to 5'-phosphorylate degradation products.

Polyacrylamide gel electrophoresis (PAGE) and RT-PCR were also tried as an attempt to isolate or "clean up" full-length RNA molecules. RT-PCR utilized primers to capture the full-length molecules, while PAGE performed RT-PCR on only barcode regions to identify remnant RNA molecules.

Figure 7:
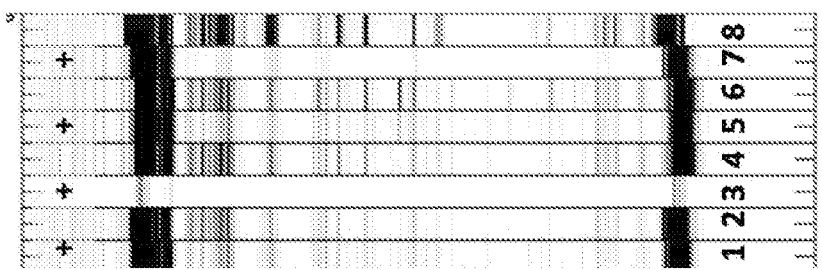
FIG. 7 illustrates exemplary data analyzing full length RNAs present after 22 hours of in vitro testing in accordance with various embodiments of the invention.

Results: FIG. 7 shows capillary electrophoresis analyzed with HiTRACE software of cDNA reverse transcribed from the P4-P6-2HP RNA that has been subject to different buffer conditions for 22 hours, including highly degrading conditions involving high pH and MgCl2. T4PNK +Xrn1 treatment 'cleans up' degradation products for this RNA. The bands that appear when RNA was incubated at high pH (e.g., lanes 5,7) are hydrolyzed RNAs. The bands disappear when the RNA is then treated with T4 PNK and Xrn1, showing that the enzymatic treatment is able to 'clean up' the degraded RNA, and leave behind full-length RNA (the dark band at the bottom of the electropherograms).

Figure 8A:
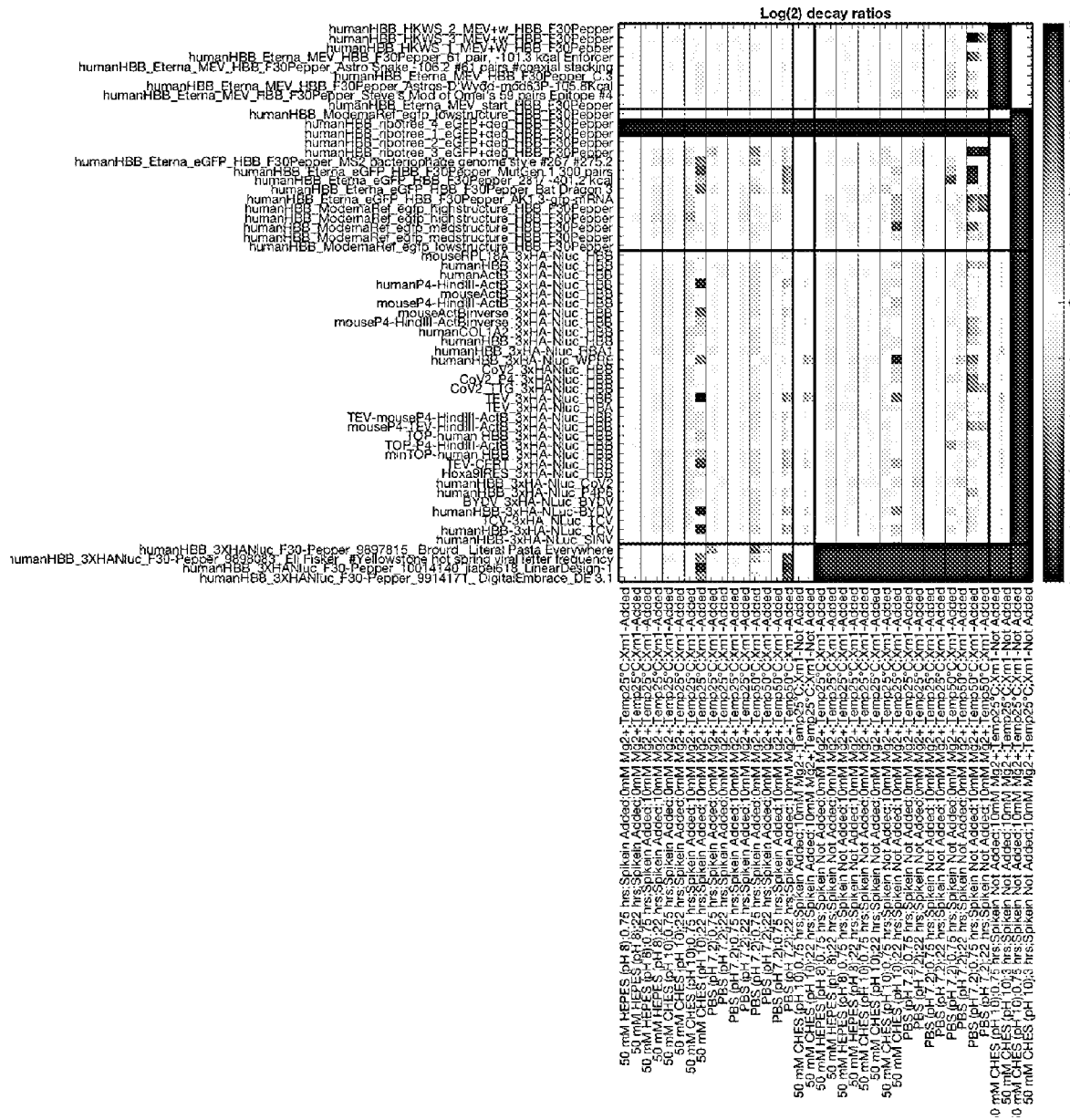
FIGS. 8A-8D illustrates exemplary data of a heatmap showing RNA dropout after 22 hours of in vitro testing in accordance with various embodiments of the invention. Specifically.
Figure 8B:
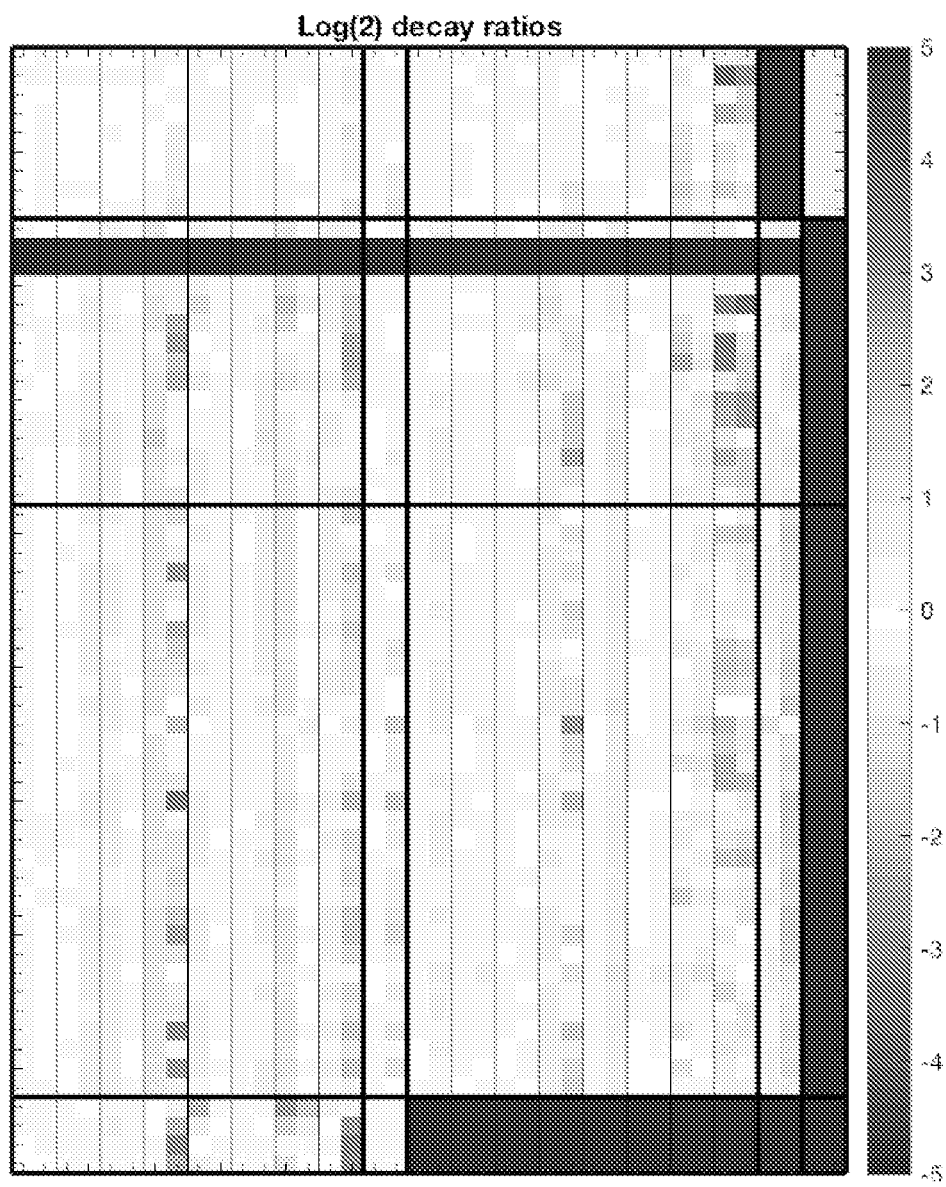
Figure 8C:
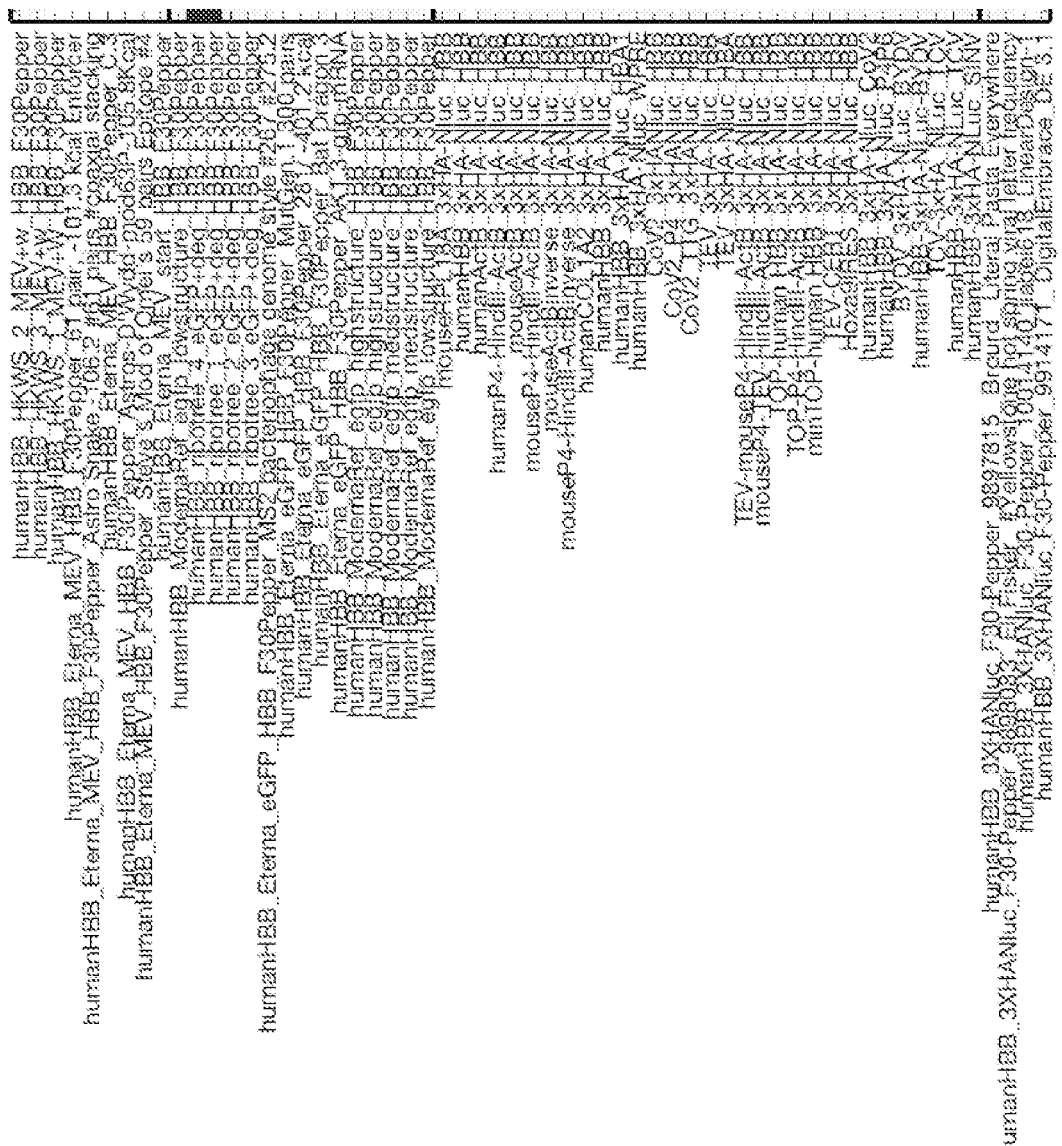
Figure 8D:
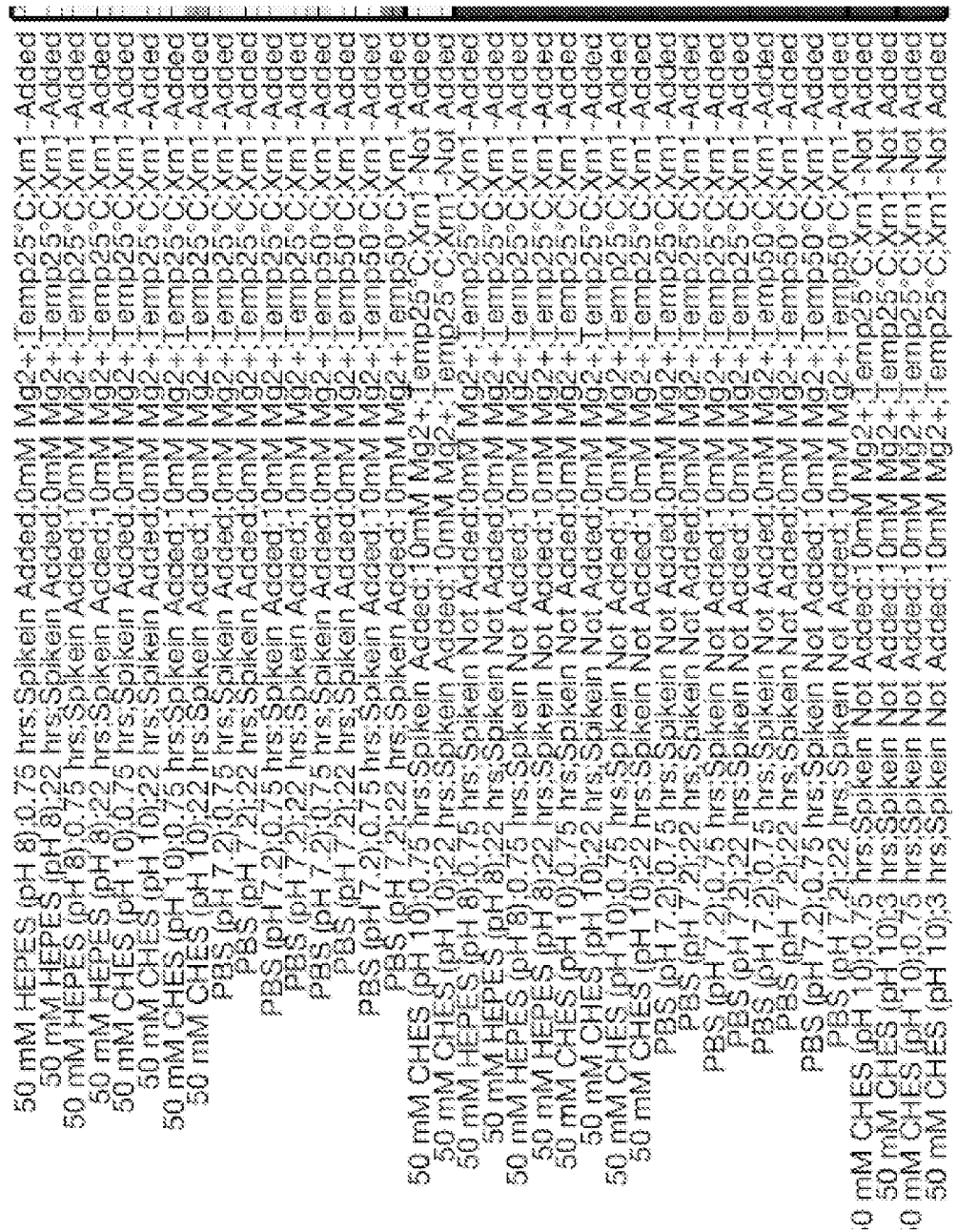

However, paradoxical results were observed when the same T4 PNK +Xrn1 was used to destroy hydrolytic degradation products of a library of >50 RNAs that had been 'aged' in different buffers, including a high pH (CHES, pH 10.0) condition expected to produce severe degradation. A single RT-PCR was used to select just the 'barcode' region of the RNAs. Counts of those RNAs were compared to a spike-in control that was not degraded; normalization of these numbers to samples that were not subjected to degradation. FIGS. 8A-8D illustrate a heatmap showing RNAs dropping out after degradation for 22 hours, but only by 2-4 fold. Specifically, FIG. 8A illustrates a full view of the heatmap and column and row labels; while FIG. 8B illustrates an enlarged view of the heatmap; FIG. 8C illustrates the row labels; and FIG. 8D illustrates the column labels. It was expected that >99% of the RNAs would be gone by that point based on one-by-one characterization of these RNAs. In addition, IT expected that RNAs with different 3' UTRs would give similar degradation rates, but instead it was observed that variation of the apparent degradation rate depending on 3' UTR identity (compare strength of blue pixels in TEV_3xHA-NLuc-HBA to TEV_3xHA-NLuc-HBB row in FIGS. 8A-8D).

The observations in FIGS. 8A-8D suggest that Xrn1 digestion might be incomplete depending on the RNA sequence; it is indeed known that some RNA sequences and structures block Xrn1. If any degraded RNA can survive the Xrn1 treatment, it can get amplified by RT-PCR.

Conclusions: Certain RNA molecules show anomalous degradation patterns after cleanup. However, such anomalies are removed by an additional RT-PCR step that selects for full-length molecules, rather than relying on degradation to filter out hydrolysis products.

Example 2

Computation Filter for Artifacts

Background: Certain RNAs still showed full-length appearance after sequencing. Such RNAs could be due to mis-priming during RT-PCR (e.g., Example 1). Many of the artifacts occurred in the GC-rich RNAs, which are known to be prone to mispriming in PCR reactions. Indeed, for some of these RNAs, use of different primer pairs resulted in data where the fraction intact did drop to 0 at long timepoints, supporting the hypothesis that these RNAs were susceptible to RT-PCR artifacts that depend on primer pairs. In addition, some of these anomalous RNAs were characterized using one-by-one synthesis, degradation, and capillary electrophoresis, and discovered that they were completely degraded by 10 hours, as expected, with no detectable fraction intact after that timepoint.

Methods: To generate a computation filter, data for each RNA was fit to single-exponential curves, then for each RNA, the difference between the experimental fraction intact at 24 hours (corresponding to >10 half-lives) was calculated, and the fraction intact expected at that time point based on the single-exponential fit. If this 'residual' was greater than 0.05, the RNA data was not considered for further analysis.

DOCTRINE OF EQUIVALENTS

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the foregoing examples and descriptions of various preferred embodiments of the present invention are merely illustrative of the invention as a whole, and that variations in the components or steps of the present invention may be made within the spirit and scope of the invention. Accordingly, the present invention is not limited to the specific embodiments described herein, but, rather, is defined by the scope of the appended claims.

The invention claimed is:

1. A method to determine RNA stability, comprising:
obtaining a pool of RNA molecules comprising a plurality of RNA sequences,
wherein each RNA molecule in the pool of RNA molecules comprises a 5' untranslated region (5'UTR), a coding sequence, a 3' untranslated region (3'UTR), a barcoding sequence, and at least one profiling sequence,
wherein the coding sequence is located 3' of the 5'UTR and 5' of the 3'UTR,
wherein the barcoding sequence is adjacent to the at least one profiling sequence and located 3' of the coding sequence and 5' of the 3'UTR,
wherein each RNA sequence differs from at least one other RNA sequence by varying at least one of the 5'UTR, the coding sequence, and the 3'UTR, and
wherein the barcoding sequence uniquely identifies a combination of the 5'UTR, coding sequence, and 3'UTR in each RNA;
treating the pool of RNA molecules under an experimental condition, wherein the experimental condition is selected from: transfection of the pool of RNA molecules into a collection of cells or addition of the pool of RNA molecules to a cell lysate;
isolating a first fraction of RNA molecules from the pool of RNA molecules at a first specified timepoint, wherein the first fraction of RNA molecules shows stability under the experimental condition at the specified timepoint;
isolating a second fraction of RNA molecules from the pool of RNA molecules at a second specified timepoint, wherein the second fraction of RNA molecules shows stability under the experimental condition the second specified timepoint;
sequencing the barcode sequence of each RNA molecule in the first fraction of RNA molecules and the second fraction of RNA molecules to identify a count of each RNA sequence in the first fraction of RNA molecules and each RNA sequence in the second fraction of RNA molecules; and
quantitatively determining stability of the RNA sequences associated with each barcode sequence based on the count of each RNA sequence in the first fraction of RNA molecules and the second fraction of RNA molecules as compared to a spike-in control, wherein a spike-in control is a non-degraded RNA molecule.

2. The method of claim 1, wherein the experimental condition is transfection of the pool of RNA molecules into a collection of cells.

3. The method of claim 2, wherein the cells are selected from mammalian cells, yeast cells, bacteria cells, and plant cells.

4. The method of claim 1, wherein the experimental condition is addition of the pool of RNA molecules to a cell lysate.

5. The method of claim 1, further comprising size selecting for full-length RNA molecules.

6. The method of claim 5, wherein size selecting comprises one or more of agarose gel electrophoresis, polyacrylamide gel electrophoresis, and capillary electrophoresis.

7. The method of claim 5, wherein size selecting comprises performing reverse transcription PCR to amplify full-length RNA molecules.

8. The method of claim 1, further comprising:
isolating a third fraction of RNA molecules from the pool of RNA molecules at a third specified timepoint, wherein the third fraction of RNA molecules shows stability under the experimental condition the third specified timepoint;
wherein sequencing the barcode sequence of each RNA molecule further comprises sequencing the barcode sequence of each RNA molecule in the third fraction of RNA molecules to identify a count of each RNA sequence in the third set of RNA molecules; and wherein quantitatively determining stability of the RNA is based on the count of each RNA sequence in the first fraction of RNA molecules, the second fraction of RNA molecules, and the third fraction of RNA molecules as compared to a spike-in control, wherein a spike-in control is a non-degraded RNA molecule.

9. The method of claim 1, further comprising generating a distribution for each RNA molecule based on the prevalence of each RNA molecule in each fraction.

10. The method of claim 1, wherein the barcoding sequence is selected from SEQ ID NOs: 2-1267.

11. The method of claim 1, wherein the profiling sequence is selected from SEQ ID NOs: 1268-1269.

12. A method to determine RNA stability, comprising:
obtaining a pool of RNA molecules comprising a plurality of RNA sequences,
  wherein each RNA molecule in the pool of RNA molecules comprises a 5' untranslated region (5'UTR), a coding sequence, a 3' untranslated region (3'UTR), a barcoding sequence, and at least one profiling sequence,
  wherein the coding sequence is located 3' of the 5'UTR and 5' of the 3'UTR,
  wherein the barcoding sequence is adjacent to the at least one profiling sequence and located 3' of the coding sequence and 5' of the 3'UTR,
  wherein each RNA sequence differs from at least one other RNA sequence by varying at least one of the 5'UTR, the coding sequence, and the 3'UTR, and
  wherein the barcoding sequence uniquely identifies a combination of the 5'UTR, coding sequence, and 3'UTR in each RNA;
treating the pool of RNA molecules under an experimental condition, wherein the experimental condition is selected from: temperature, pH, presence of certain molecules, presence of certain ions, concentration of certain molecules, concentration of certain ions, irradiation, buffer type, and buffer concentration;
isolating a first fraction of RNA molecules from the pool of RNA molecules at a first timepoint, wherein the first fraction of RNA molecules shows stability under the experimental condition at the first timepoint;
isolating a second fraction of RNA molecules from the pool of RNA molecules at a second timepoint, wherein the second fraction of RNA molecules shows stability under the experimental condition at the second timepoint;
sequencing the barcode sequence of each RNA molecule in the first fraction of RNA molecules and the second fraction of RNA molecules to identify a count of each RNA sequence in the first fraction of RNA molecules and each RNA sequence in the second fraction of RNA molecules; and
quantitatively determining stability of the RNA sequences associated with each barcode sequence based on the count of each RNA sequence in the first fraction of RNA molecules and the second fraction of RNA molecules as compared to a spike-in control, wherein a spike-in control is a non-degraded RNA molecule.

13. The method of claim 12, further comprising size selecting for full-length RNA molecules.

14. The method of claim 13, wherein size selecting comprises one or more of agarose gel electrophoresis, polyacrylamide gel electrophoresis, and capillary electrophoresis.

15. The method of claim 13, wherein size selecting comprises performing reverse transcription PCR to amplify full-length RNA molecules.

16. The method of claim 12, further comprising:
isolating a third fraction of RNA molecules from the pool of RNA molecules at a third timepoint, wherein the third fraction of RNA molecules shows stability under the experimental condition the third timepoint;
wherein sequencing the barcode sequence of each RNA molecule further comprises sequencing the barcode sequence of each RNA molecule in the third fraction of RNA molecules to identify a count of each RNA sequence in the third set of RNA molecules; and
wherein quantitatively determining stability of the RNA molecules is based on the count of each RNA sequence in the first fraction of RNA molecules, the second fraction of RNA molecules, and the third fraction of RNA molecules as compared to a spike-in control, wherein a spike-in control is a non-degraded RNA molecule.

17. The method of claim 12, further comprising generating a distribution for each RNA molecule based on the prevalence of each RNA molecule in each fraction.

18. The method of claim 12, wherein the barcoding sequence is selected from SEQ ID NOs: 2-1267.

19. The method of claim 12, wherein the profiling sequence is selected from SEQ ID NOs: 1268-1269.

* * * * *